(12) United States Patent
Thorne et al.

(10) Patent No.: US 12,246,049 B2
(45) Date of Patent: *Mar. 11, 2025

(54) ONCOLYTIC VIRUSES TARGETING STAT3

(71) Applicant: UNIVERSITY OF PITTSBURGH—OF THE COMMONWEALTH SYSTEM OF HIGHER EDUCATION, Pittsburgh, PA (US)

(72) Inventors: Stephen Howard Thorne, Pittsburgh, PA (US); Daniel J. Byrd, Pittsburgh, PA (US)

(73) Assignee: UNIVERSITY OF PITTSBURGH - OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/452,307

(22) Filed: Aug. 18, 2023

(65) Prior Publication Data

US 2024/0016865 A1  Jan. 18, 2024

Related U.S. Application Data

(60) Division of application No. 17/574,691, filed on Jan. 13, 2022, now abandoned, and a division of application No. 17/574,763, filed on Jan. 13, 2022, now abandoned, said application No. 17/574,691 is a division of application No. 16/252,338, filed on Jan. 18, 2019, now Pat. No. 11,253,559, said application No. 17/574,763 is a division of application No. 16/252,338, filed on Jan. 18, 2019, now Pat. No. 11,253,559, which is a continuation of application No. PCT/US2017/042910, filed on Jul. 19, 2017.

(60) Provisional application No. 62/364,095, filed on Jul. 19, 2016.

(51) Int. Cl.

| A61K 35/768 | (2015.01) |
|---|---|
| A61K 9/00 | (2006.01) |
| A61P 35/00 | (2006.01) |
| C07K 14/07 | (2006.01) |
| C07K 14/16 | (2006.01) |
| C07K 14/47 | (2006.01) |
| C12N 9/10 | (2006.01) |
| C12N 9/16 | (2006.01) |
| C12N 15/62 | (2006.01) |
| C07K 16/28 | (2006.01) |

(52) U.S. Cl.
CPC .......... *A61K 35/768* (2013.01); *A61K 9/0019* (2013.01); *A61P 35/00* (2018.01); *C07K 14/07* (2013.01); *C07K 14/16* (2013.01); *C07K 14/4702* (2013.01); *C12N 9/104* (2013.01); *C12N 9/16* (2013.01); *C12N 15/625* (2013.01); *C12Y 301/03048* (2013.01); *C07K 16/2827* (2013.01); *C12N 2710/24132* (2013.01); *C12N 2710/24143* (2013.01)

(58) Field of Classification Search
None
See application file for complete search history.

(56) References Cited

U.S. PATENT DOCUMENTS

| 5,399,363 A | 3/1995 | Liversidge et al. |
|---|---|---|
| 5,543,158 A | 8/1996 | Gref et al. |
| 5,641,515 A | 6/1997 | Ramtoola |
| 6,506,559 B1 | 1/2003 | Fire et al. |
| 6,573,099 B2 | 6/2003 | Graham |
| 2003/0083249 A1 | 5/2003 | Brown et al. |
| 2004/0248787 A1 | 12/2004 | Naito et al. |
| 2007/0213288 A1 | 9/2007 | Haura et al. |
| 2013/0202577 A1 | 8/2013 | Tiganis et al. |
| 2016/0060311 A1 | 3/2016 | Jo et al. |
| 2016/0152678 A1 | 6/2016 | Bancel et al. |

FOREIGN PATENT DOCUMENTS

| CN | 101381742 A | 3/2009 |
|---|---|---|
| CN | 102796709 A | 11/2012 |
| CN | 103614416 B | 9/2016 |
| JP | 2016-512199 A | 4/2016 |
| WO | WO 1999/032619 A1 | 7/1999 |
| WO | WO 00/34468 A2 | 6/2000 |
| WO | WO 2001/036646 A1 | 5/2001 |
| WO | WO 2001/068836 A2 | 9/2001 |
| WO | WO 01/79555 A2 | 10/2001 |
| WO | WO 02/20032 A1 | 3/2002 |
| WO | WO 02/42489 A1 | 5/2002 |
| WO | WO 2004/016735 A2 | 2/2004 |
| WO | WO 2004/108955 A1 | 12/2004 |
| WO | WO 2008/150814 A2 | 12/2008 |

(Continued)

OTHER PUBLICATIONS

U.S. Appl. No. 16/252,338 (U.S. Pat. No. 11,253,559), filed Jan. 18, 2019 (Feb. 22, 2022).

(Continued)

*Primary Examiner* — Nicole Kinsey White
(74) *Attorney, Agent, or Firm* — Baker Botts L.L.P

(57) ABSTRACT

This disclosure relates to modified viruses, e.g., oncolytic vaccinia viruses, which have been modified to contain an exogenous nucleic acid that expresses a protein that modulates STAT3 activity. It is based, at least in part, on the discovery that vaccinia viruses modified to contain nucleic acid encoding PIAS3 and that express PIAS3 or a fragment thereof can inhibit STAT3 activity and enhance the anti-cancer activity of the vaccinia virus. Accordingly, this disclosure provides for oncolytic vaccinia viruses and methods of using them in the treatment of cancers.

20 Claims, 9 Drawing Sheets
Specification includes a Sequence Listing.

(56) References Cited

FOREIGN PATENT DOCUMENTS

| WO | WO 2011/066578 A1 | 6/2011 |
|---|---|---|
| WO | WO 2011/098806 A1 | 8/2011 |
| WO | WO 2011/110359 A1 | 9/2011 |
| WO | WO 2014/185973 A2 | 11/2014 |
| WO | WO 2015/027163 A1 | 2/2015 |
| WO | WO 2015/184061 A2 | 12/2015 |

OTHER PUBLICATIONS

U.S. Appl. No. 17/574,691 (US 2022/0133824), filed Jan. 13, 2022 (May 5, 2022).
U.S. Appl. No. 17/574,763 (US 2022/0133825), filed Jan. 13, 2022 (May 5, 2022).
U.S. Appl. No. 17/574,763, filed May 19, 2023 Non-Final Office Action.
U.S. Appl. No. 17/574,691, filed May 18, 2023 Non-Final Office Action.
U.S. Appl. No. 16/252,338, filed Jan. 13, 2022 Issue Fee Payment.
U.S. Appl. No. 16/252,338, filed Oct. 14, 2021 Notice of Allowance.
U.S. Appl. No. 16/252,338, filed Sep. 9, 2021 Response to Non-Final Office Action.
U.S. Appl. No. 16/252,338, filed May 17, 2021 Non-Final Office Action.
U.S. Appl. No. 16/252,338, filed Apr. 6, 2021 Response to Final Office Action.
U.S. Appl. No. 16/252,338, filed Jan. 14, 2021 Final Office Action.
U.S. Appl. No. 16/252,338, filed Sep. 23, 2020 Response to Non-Final Office Action.
U.S. Appl. No. 16/252,338, filed Jun. 23, 2020 Non-Final Office Action.
U.S. Appl. No. 16/252,338, filed Apr. 10, 2020 Response to Restriction Requirement.
U.S. Appl. No. 16/252,338, filed Feb. 19, 2020 Restriction Requirement.
Alcami et al., "A Soluble Receptor for Interleukin-1β Encoded by Vaccinia Virus: A Novel Mechanism of Virus Modulation of the Host Response to Infection," Cell 71:153-167 (1992).
Altschul et al., "Gapped BLAST and PSI-BLAST: a new generation of protein database search programs," Nucleic Acids Res., 25(17):3389-3402 (1997).
Anonymous: "Combining STAT3-Silencing and Oncolytic Vaccinia Virus to Enhance Anti-Tumor Therapeutic Activity," Project Information—1F32CA199981-01A1, (Mar. 7, 2016).
Borrelli et al., Molecules, 23:295 (2018).
Bu et al., "GRIM-19 inhibits the STAT3 signaling pathway and sensitizes gastric cancer cells to radiation," Gene 512:198-205 (2013).
Byrd, "Combining STAT3-silencing and oncolytic vaccinia virus to enhance anti-tumor therapeutic activity," Project Information—1F32CA 199981-01A1, NIH RePORTER, https://reporter.nih.gov/project-details/9123078#details (2016).
Carpenter et al., "STAT3 Target Genes Relevant to Human Cancers," Cancers, 6:897-925 (2014).
Chartier et al., "Efficient Generation of Recombinant Adenovirus Vectors by Homologous Recombination in *Escherichia coli*,", J. Virol 70(7):4805-4810 (1996).
Colamonici et al., "Vaccinia Virus B18R Gene Encodes a Type I Interferon-binding Protein That Blocks Interferon a Transmembrane Signaling," J. Biol. Chem. 270(27):15974-15978 (1995).
Duval et al., "The 'PINIT' motif, of a newly identified conserved domain of the PIAS protein family, is essential for nuclear retention of PIAS3L," FEBS Letters 554:111-118 (2003).
Fahy et al., "Vaccinia virus protein C16 acts intracellularly to modulate the host response and promote virulence," J. Gen. Virol. 89:2377-2387 (2008).
Furtek et al., "Strategies and Approaches of Targeting STAT3 for Cancer Treatment," ACS Chem. Biol. 11:308-318 (2016).
GenBank Accession No. AY890963, Jan. 5, 2005 (2 pgs.).
Hernandez-Gea et al., "Oncolytic immunotherapeutic virus in HCC: Can it compete with molecular therapies?" Journal of Hepatology, 59:882-884 (2013).
International Search Report mailed Mar. 6, 2018 in International Application No. PCT/US17/42910.
Kajiwara et al., "Cell penetrating peptide," Journal of Japanese Pharmacology 141:220-221 (2013) [with English machine translation].
Karlin et al., "Applications and statistics for multiple high-scoring segments in molecular sequences," PNAS USA, 90:5873-5877 (1993).
Kirn et al., "Targeted and armed oncolytic poxviruses: a novel multi-mechanistic therapeutic class for cancer," Nat Rev Cancer 9:64-71 (2009).
Lv et al., "Oncolytic vaccine virus harbouring the IL-24 gene suppresses the growth of lung cancer by inducing apoptosis," Biochemical and Biophysical Research Communications 476:21-28 (2016).
Mahony et al., "SOCS3 revisited: a broad regulator of disease, now ready for therapeutic use?" Cell. Mol. Life Sci. 73:3323-3336 (2016).
Mautsa et al., "The PINIT domain of PIAS3: structure-function analysis of its interaction with STAT3," Journal of Molecular Recognition 24:795-803 (2011).
Ogata et al., "Overexpression of PIAS3 Suppresses Cell Growth, Restores the Drug Sensitivity of Human Lung Cancer Cells in Association with PI3-K/Akt Inactivation," Neoplasia 8(10):817-825 (2006).
Paul et al., "Tumor gene therapy by MVA-mediated expression of T-cell-stimulating antibodies," Cancer Gene Ther. 9:470-477 (2002).
Sampath et al., "Crosstalk between Immune Cell and Oncolytic Vaccinia Therapy Enhances Tumor Trafficking and Antitumor Effects," Mol. Ther., 21(3):620-628 (2013).
Shields et al., "TCPTP Regulates SFK and STAT3 Signaling and Is Lost in Triple-Negative Breast Cancers," Mol. Cell Biol., 33(3):557-570 (2013).
Siveen et al., "Targeting the STAT3 signaling pathway in cancer: Role of synthetic and natural inhibitors," Biochimica et Biophysica Acta 1845:136-154 (2014).
Starr et al., "A family of cytokine-inducible inhibitors of signalling," Nature, 387:917-921 (1997).
Supplementary Partial European Search Report dated Feb. 18, 2020 in Application No. EP 17831813.
Symons et al., "Vaccinia Virus Encodes a Soluble Type I Interferon Receptor of Novel Structure and Broad Species Specificity," Cell 81:551-560 (1995).
Thorne et al., "Rational strain selection and engineering creates a broad-spectrum, systematically effective oncolytic poxvirus, JX-963," The Journal of Clinical Investigation, 117(11):3350-3358 (2007).
Yagil et al., Trends in Immunology, 31(5):199-204 (2010).
Yue et al., "Targeting STAT3 in cancer: how successful are we?" Expert Opin. Investig. Drugs 18(1):45-56 (2009).

SEQUENCE LISTING

```
Sequence total quantity: 43
SEQ ID NO: 1           moltype = AA  length = 628
FEATURE                Location/Qualifiers
source                 1..628
                       mol_type = protein
                       organism = Homo sapiens
SEQUENCE: 1
MAELGELKHM VMSFRVSELQ VLLGFAGRNK SGRKHELLAK ALHLLKSSCA PSVQMKIKEL  60
YRRRFPRKTL GPSDLSLLSL PPGTSPVGSP GPLAPIPPTL LAPGTLLGPK REVDMHPPLP 120
QPVHPDVTMK PLPFYEVYGE LIRPTTLAST SSQRFEEAHF TFALTPQQVQ QILTSREVLP 180
GAKCDYTIQV QLRFCLCETS CPQEDYFPPN LFVKVNGKLC PLPGYLPPTK NGAEPKRPSR 240
PINITPLARL SATVPNTIVV NWSSEFGRNY SLSVYLVRQL TAGTLLQKLR AKGIRNPDHS 300
RALIKEKLTA DPDSEVATTS LRVSLMCPLG KMRLTVPCRA LTCAHLQSFD AALYLQMNEK 360
KPTWTCPVCD KKAPYESLII DGLFMEILSS CSDCDEIQFM EDGSWCPMKP KKEASEVCPP 420
PGYGLDGLQY SPVQGGDPSE NKKKVEVIDL TIESSSDEED LPPTKKHCSV TSAAIPALPG 480
SKGVLTSGHQ PSSVLRSPAM GTLGGDFLSS LPLHEYPPAF PLGADIQGLD LFSFLQTESQ 540
HYGPSVITSL DEQDALGHFF QYRGTPSHFL GPLAPTLGSS HCSATPAPPP GRVSSIVAPG 600
GALREGHGGP LPSGPSLTGC RSDIISLD                                   628
```

```
SEQ ID NO: 2               moltype = AA   length = 184
FEATURE                    Location/Qualifiers
source                     1..184
                           mol_type = protein
                           organism = Homo sapiens
SEQUENCE: 2
PFYEVYGELI RPTTLASTSS QRFEEAHFTF ALTPQQVQQI LTSREVLPGA KCDYTIQVQL   60
RFCLCETSCP QEDYFPPNLF VKVNGKLCPL PGYLPPTKNG AEPKRPSRPI NITPLARLSA  120
TVPNTIVVNW SSEFGRNYSL SVYLVRQLTA GTLLQKLRAK GIRNPDHSRA LIKEKLTADP  180
DSEV                                                               184

SEQ ID NO: 3               moltype = AA   length = 46
FEATURE                    Location/Qualifiers
source                     1..46
                           mol_type = protein
                           organism = Homo sapiens
SEQUENCE: 3
LPFYEVYGEL IRPTTLASTS SQRFEEAHFT FALTPQQVQQ ILTSRE                   46

SEQ ID NO: 4               moltype = AA   length = 51
FEATURE                    Location/Qualifiers
source                     1..51
                           mol_type = protein
                           organism = Homo sapiens
SEQUENCE: 4
DVTMKPLPFY EVYGELIRPT TLASTSSQRF EEAHFTFALT PQQVQQILTS R             51

SEQ ID NO: 5               moltype = AA   length = 188
FEATURE                    Location/Qualifiers
source                     1..188
                           mol_type = protein
                           organism = Homo sapiens
SEQUENCE: 5
MKPLPFYEVY GELIRPTTLA STSSQRFEEA HFTFALTPQQ VQQILTSREV LPGAKCDYTI   60
QVQLRFCLCE TSCPQEDYFP PNLFVKVNGK LCPLPGYLPP TKNGAEPKRP SRPINITPLA  120
RLSATVPNTI VVNWSSEFGR NYSLSVYLVR QLTAGTLLQK LRAKGIRNPD HSRALIKEKL  180
TADPDSEV                                                           188

SEQ ID NO: 6               moltype = AA   length = 628
FEATURE                    Location/Qualifiers
source                     1..628
                           mol_type = protein
                           organism = Mus musculus
SEQUENCE: 6
MAELGELKHM VMSFRVSELQ VLLGFAGRNK SGRKHELLAK ALHLLKSSCA PSVQMKIKEL   60
YRRRFPRKTL GPSDLSLLSL PPGTSPVGSP GPLAPIPPTL LTPGTLLGPK REVDMHPPLP  120
QPVHPDVTMK PLPFYEVYGE LIRPTTLAST SSQRFEEAHF TFALTPQQLQ QILTSREVLP  180
GAKCDYTIQV QLRFCLCETS CPQEDYFPPN LFVKVNGKLC PLPGYLPPTK NGAEPKRPSR  240
PINITPLARL SATVPNTIVV NWSSEFGRNY SLSVYLVRQL TAGTLLQKLR AKGIRNPDHS  300
RALIKEKLTA DPDSEVATTS LRVSLMCPLG KMRLTVPCRA LTCAHLSFDA AALYLQMNEK  360
KPTWTCPVCD KKAPYESLII DGLFMEILNS CSDCDEIQFM EDGSWCPMKP KKEASEVCPP  420
PGYGLDGLQY SAVQEGIQPE SKKRVEVIDL TIESSSDEED LPPTKKHCPV TSAAIPALPG  480
SKGALTSGHQ PSSVLRSPAM GTLGSDFLSS LPLHEYPPAF PLGADIQGLD LFSFLQTESQ  540
HYGPSVITSL DEQDTLGHFF QYRGTPSHFL GPLAPTLGSS HRSSTPAPPP GRVSSIVAPG  600
SSLREGHGGP LPSGPSLTGC RSDVISLD                                    628

SEQ ID NO: 7               moltype = AA   length = 628
FEATURE                    Location/Qualifiers
source                     1..628
                           mol_type = protein
                           organism = Rattus norvegicus
SEQUENCE: 7
MAELGELKHM VMSFRVSELQ VLLGFAGRNK SGRKHELLAK ALHLLKSSCA PSVQMKIKEL   60
YRRRFPRKTL GPSDLSLLSL PPGTSPVGSP SPLASIPPTL LTPGTLLGPK REVDMHPPLP  120
QPVHPDVTMK PLPFYEVYGE LIRPTTLAST SSQRFEEAHF TFALTPQQLQ QILTSREVLP  180
GAKCDYTIQV QLRFCLCETS CPQEDYFPPN LFVKVNGKLC PLPGYLPPTK NGAEPKRPSR  240
PINITPLARL SATVPNTIVV NWSSEFGRNY SLSVYLVRQL TAGTLLQKLR AKGIRNPDHS  300
RALIKEKLTA DPDSEVATTS LRVSLMCPLG KMRLTVPCRA LTCAHLSFDA AALYLQMNEK  360
KPTWTCPVCD KKAPYESLII DGLFMEILNS CSDCDEIQFM EDGSWCPMKP KKEASEVCPP  420
PGYGLDGLQY SPVQEGNQSE NKKRVEVIDL TIESSSDEED LPPTKKHCPV TSAAIPALPG  480
SKGALTSGHQ PSSVLRSPAM GTLGSDFLSS LPLHEYPPAF PLGADIQGLD LFSFLQTESQ  540
HYSPSVITSL DEQDTLGHFF QFRGTPPHFL GPLAPTLGSS HRSATPAPAP GRVSSIVAPG  600
SSLREGHGGP LPSGPSLTGC RSDVISLD                                    628

SEQ ID NO: 8               moltype = DNA   length = 1887
FEATURE                    Location/Qualifiers
source                     1..1887
                           mol_type = other DNA
                           organism = Homo sapiens
```

```
SEQUENCE: 8
atggcggagc tgggcgaatt aaagcacatg gtgatgagtt tccgggtgtc tgagctccag    60
gtgcttcttg gctttgctgg ccggaacaag agtggacgga agcacgagct cctgccaag   120
gctctgcacc tcctgaagtc cagctgtgcc cctagtgtcc agatgaagat caaagagctt   180
taccgacgac gctttcccg gaagaccctg gggccctctg atctctccct tctctctttg    240
cccctggca cctctcctgt aggctcccct ggtcctctag ctcccattcc cccaacgctg    300
ttggcccctg gcaccctgct gggcccaag cgtgaggtgg acatgcaccc ccctctgccc    360
cagcctgtgc accctgatgt caccatgaaa ccattgccct tctatgaagt ctatggggag   420
ctcatccggc ccaccaccct tgcatccact tctagccagc ggtttgagga agcgcacttt   480
acctttgccc tcacacccca gcaagtgcag cagattctta catccagaga ggttctgcca   540
ggagccaaat gtgattatac catacaggtg cagctaaggt tctgtctctg tgagaccagc   600
tgcccccagg aagattattt tccccccaac ctctttgtca aggtcaatgg gaaactgtgc   660
cccctgccgg gttaccttcc cccaaccaag aatgggggcg agcccaagag gcccagccgc   720
cccatcaaca tcacacccct ggctcgactc tcagcgactc cattgtggtc                780
aattggtcat ctgagttcgg acggaattac tccttgtctg tgtacctggt gaggcagttg   840
actgcaggaa cccttctaca aaaactcaga gcaaagggta tccggaaccc agaccactcg   900
cgggcactga tcaaggagaa attgactgct gaccctgaca gtgaggtggc cactacaagt   960
ctccgggtgt cactcatgtg cccgctaggg aagatgcgcc tgactgtccc ttgtcgtgcc  1020
ctcacctgcg cccacctgca gagcttcgat gctgcccttt atctacagat gaatgagaag  1080
aagcctacat ggacatgtcc tgtgtgtgac aagaaggctc cctatgaatc tcttatcatt  1140
gatggtttat ttatggagat tcttagttcc tgttcagatt gtgatgagat ccaattcatg  1200
gaagatggat cctggtgccc aatgaaaccc aagaaggagg catctgaggt ttgcccccg   1260
ccagggtatg gctgatgg cctccagtac agcccagtcc aggggggaga tccatcagag   1320
aataagaaga aggtcgaagt tattgacttg acaatagaaa gctcatcaga tgaggaggat   1380
ctgcccccta ccaagaagca ctgttctgtc acctcagctg ccatcccggc cctacctgga   1440
agcaaaggag tcctgacatc tggccaccag ccatcctcac tgctaaggag ccctgctatg   1500
ggcacgttgg gtggggattt cctgtccagt ctcccactac atgagtaccc acctgccttc   1560
ccactgggag ccgacatcca aggtttagat ttatttcat ttcttcagac agagagtcag   1620
cactatggcc cctctgtcat cacctcacta gatgaacagg atgcccttgg ccacttcttc   1680
cagtaccagg ggacccttc tcactttctg ggcccactgg cccccacgct ggggagctcc   1740
cactgcagcg ccactccggc gcccctcct ggccgtgtca gcagcattgt ggccctgggg   1800
ggggccttga gggagggca tggaggaccc ctgccctcag gtccctcttt gactggctgt   1860
cggtcagaca tcattccct ggactga                                       1887

SEQ ID NO: 9        moltype = DNA  length = 552
FEATURE             Location/Qualifiers
source              1..552
                    mol_type = other DNA
                    organism = Homo sapiens
SEQUENCE: 9
cccttctatg aagtctatgg ggagctcatc cggcccacca cccttgcatc cacttctagc    60
cagcggtttg aggaagcgca ctttaccttt gccctcacac cccagcaagt gcagcagatt   120
cttacatcca gagaggttct gccaggagcc aaatgtgatt ataccataca ggtgcagcta   180
aggttctgtc tctgtgagac cagctgcccc caggaagatt attttccccc caacctcttt   240
gtcaaggtca atgggaaact gtgccccctg ccgggttacc ttccccaac caagaatggg   300
gccgagccca gaggcccag ccgccccatc aacatcacac ccctggctcg actctcagcc   360
actgttccca acaccattgt ggtcaattgg tcatctgagt tcggacggaa ttactccttg   420
tctgtgtacc tggtgaggca gttgactgca ggaaccctt ctacaaaaact cagagcaaag    480
ggtatccgga acccagacca ctcgcgggca ctgatcaagg agaaattgac tgctgaccct   540
gacagtgagg tg                                                       552

SEQ ID NO: 10       moltype = DNA  length = 138
FEATURE             Location/Qualifiers
source              1..138
                    mol_type = other DNA
                    organism = Homo sapiens
SEQUENCE: 10
ttgcccttct atgaagtcta tggggagctc atccggccca ccaccttgc atccacttct    60
agccagcggt tgaggaagc gcactttacc tttgccctca cccccagca agtgcagcag   120
attcttacat ccagagag                                                 138

SEQ ID NO: 11       moltype = AA   length = 11
FEATURE             Location/Qualifiers
source              1..11
                    mol_type = protein
                    organism = Human immunodeficiency virus 1
SEQUENCE: 11
YGRKKRRQRR R                                                         11

SEQ ID NO: 12       moltype = DNA  length = 33
FEATURE             Location/Qualifiers
source              1..33
                    mol_type = other DNA
                    organism = Human immunodeficiency virus 1
SEQUENCE: 12
tatggcagga agaagcggag acagcgacga aga                                 33

SEQ ID NO: 13       moltype = DNA  length = 33
FEATURE             Location/Qualifiers
```

```
source                  1..33
                        mol_type = other DNA
                        organism = Human immunodeficiency virus 1
SEQUENCE: 13
tatggacgaa aaaacgacg acaacgacga cga                                33

SEQ ID NO: 14           moltype = DNA   length = 24
FEATURE                 Location/Qualifiers
source                  1..24
                        mol_type = other DNA
                        organism = Human immunodeficiency virus 1
SEQUENCE: 14
cgacaacgac gaaagaagcg aggt                                         24

SEQ ID NO: 15           moltype = AA   length = 8
FEATURE                 Location/Qualifiers
source                  1..8
                        mol_type = protein
                        organism = Human immunodeficiency virus 1
SEQUENCE: 15
RQRRKKRG                                                           8

SEQ ID NO: 16           moltype = AA   length = 40
FEATURE                 Location/Qualifiers
source                  1..40
                        mol_type = protein
                        organism = Yersinia pestis
SEQUENCE: 16
KSKTEYYNAW SEWERNAPPG NGEQREMAVS RLRDCLDRQA                        40

SEQ ID NO: 17           moltype = DNA   length = 120
FEATURE                 Location/Qualifiers
source                  1..120
                        mol_type = other DNA
                        organism = Yersinia pestis
SEQUENCE: 17
aagagtaaga cggagtatta caatgcttgg tcagagtggg agcgaaacgc ccctccaggc  60
aatggggagc agcgagagat ggcggtgagt cggttgaggg actgtctcga caggcaggca 120

SEQ ID NO: 18           moltype = AA   length = 27
FEATURE                 Location/Qualifiers
REGION                  1..27
                        note = Description of Unknown: Transportan sequence
source                  1..27
                        mol_type = protein
                        organism = unidentified
SEQUENCE: 18
GWTLNSAGYL LGKINLKALA ALAKKIL                                      27

SEQ ID NO: 19           moltype = DNA   length = 81
FEATURE                 Location/Qualifiers
misc_feature            1..81
                        note = Description of Unknown: Transportan sequence
source                  1..81
                        mol_type = other DNA
                        organism = unidentified
SEQUENCE: 19
ggctggacac ttaacagcgc aggatatttg cttggcaaaa tcaatttgaa ggccttggct  60
gcgcttgcaa aaaaaattct c                                            81

SEQ ID NO: 20           moltype = AA   length = 16
FEATURE                 Location/Qualifiers
REGION                  1..16
                        note = Description of Unknown: Penetratin sequence
source                  1..16
                        mol_type = protein
                        organism = unidentified
SEQUENCE: 20
RQIKIWFQNR RMKWKK                                                  16

SEQ ID NO: 21           moltype = DNA   length = 48
FEATURE                 Location/Qualifiers
misc_feature            1..48
                        note = Description of Unknown: Penetratin sequence
source                  1..48
                        mol_type = other DNA
                        organism = unidentified
SEQUENCE: 21
cggcagataa aaatctggtt ccagaatcgg cgcatgaaat ggaagaaa               48
```

```
SEQ ID NO: 22              moltype = AA  length = 15
FEATURE                    Location/Qualifiers
REGION                     1..15
                           note = Description of Artificial Sequence: Synthetic peptide
source                     1..15
                           mol_type = protein
                           organism = synthetic construct
SEQUENCE: 22
RRRRRRRRRH HHHHH                                                         15

SEQ ID NO: 23              moltype = DNA  length = 45
FEATURE                    Location/Qualifiers
misc_feature               1..45
                           note = Description of Artificial Sequence: Synthetic
                           oligonucleotide
source                     1..45
                           mol_type = other DNA
                           organism = synthetic construct
SEQUENCE: 23
aggcggcgaa gacgccgcag gagacggcac caccatcacc atcac             45

SEQ ID NO: 24              moltype = AA  length = 124
FEATURE                    Location/Qualifiers
source                     1..124
                           mol_type = protein
                           organism = Homo sapiens
SEQUENCE: 24
MEDGSWCPMK PKKEASEVCP PPGYGLDGLQ YSPVQGGDPS ENKKKVEVID LTIESSSDEE         60
DLPPTKKHCS VTSAAIPALP GSKGVLTSGH QPSSVLRSPA MGTLGGDFLS SLPLHEYPPA        120
FPLG                                                                    124

SEQ ID NO: 25              moltype = AA  length = 139
FEATURE                    Location/Qualifiers
REGION                     1..139
                           note = Description of Artificial Sequence: Synthetic
                           polypeptide
source                     1..139
                           mol_type = protein
                           organism = synthetic construct
SEQUENCE: 25
MEDGSWCPMK PKKEASEVCP PPGYGLDGLQ YSPVQGGDPS ENKKKVEVID LTIESSSDEE         60
DLPPTKKHCS VTSAAIPALP GSKGVLTSGH QPSSVLRSPA MGTLGGDFLS SLPLHEYPPA        120
FPLGRRRRRR RRRHHHHHH                                                    139

SEQ ID NO: 26              moltype = AA  length = 124
FEATURE                    Location/Qualifiers
source                     1..124
                           mol_type = protein
                           organism = Mus musculus
SEQUENCE: 26
MEDGSWCPMK PKKEASEVCP PPGYGLDGLQ YSAVQEGIQP ESKKRVEVID LTIESSSDEE         60
DLPPTKKHCP VTSAAIPALP GSKGALTSGH QPSSVLRSPA MGTLGSDFLS SLPLHEYPPA        120
FPLG                                                                    124

SEQ ID NO: 27              moltype = AA  length = 139
FEATURE                    Location/Qualifiers
REGION                     1..139
                           note = Description of Artificial Sequence: Synthetic
                           polypeptide
source                     1..139
                           mol_type = protein
                           organism = synthetic construct
SEQUENCE: 27
MEDGSWCPMK PKKEASEVCP PPGYGLDGLQ YSAVQEGIQP ESKKRVEVID LTIESSSDEE         60
DLPPTKKHCP VTSAAIPALP GSKGALTSGH QPSSVLRSPA MGTLGSDFLS SLPLHEYPPA        120
FPLGRRRRRR RRRHHHHHH                                                    139

SEQ ID NO: 28              moltype = AA  length = 225
FEATURE                    Location/Qualifiers
source                     1..225
                           mol_type = protein
                           organism = Homo sapiens
SEQUENCE: 28
MVTHSKFPAA GMSRPLDTSL RLKTFSSKSE YQLVVNAVRK LQESGFYWSA VTGGEANLLL         60
SAEPAGTFLI RDSSDQRHFF TLSVKTQSGT KNLRIQCEGG SFSLQSDPRS TQPVPRFDCV        120
LKLVHHYMPP PGAPSFPSPP TEPSSEVPEQ PSAQPLPGSP PRRAYYIYSG GEKIPLVLSR        180
PLSSNVATLQ HLCRKTVNGH LDSYEKVTQL PGPIREFLDQ YDAPL                       225
```

-continued

```
SEQ ID NO: 29          moltype = DNA  length = 675
FEATURE                Location/Qualifiers
source                 1..675
                       mol_type = other DNA
                       organism = Homo sapiens
SEQUENCE: 29
atggtcaccc acagcaagtt tcccgccgcc gggatgagcc gccccctgga caccagcctg    60
cgcctcaaga ccttcagctc caagagcgag taccagctgg tggtgaacgc agtgcgcaag   120
ctgcaggaga gcggcttcta ctggagcgca gtgaccggcg cgaggcgaaa cctgctgctc   180
agtgccgagc ccgccggcac ctttctgatc cgcgacagtc cggaccagcg ccacttcttc   240
acgctcagcg tcaagaccca gtctgggacc aagaacctgc gcatccagtg tgaggggggc   300
agcttctctc tgcagagcga tccccggagc acgcagcccg tgccccgctt cgactgcgtg   360
ctcaagctgg tgcaccacta catgccgccc ctggagccc ctccttccc ctcgccacct    420
actgaaccct cctccgaggt gcccgagcag ccgtctgcca agccactccc tgggagtcc    480
cccagaagag cctattacat ctactccggg ggcgagaaga tccccctggt gttgagccgg   540
cccctctcct ccaacgtggc cactcttcag catctctgtc ggaagaccgt caacggccac   600
ctggactcct atgagaaagt cacccagctg ccggggccca ttcgggagtt cctggaccag   660
tacgatgccc cgctt                                                   675

SEQ ID NO: 30          moltype = AA  length = 225
FEATURE                Location/Qualifiers
source                 1..225
                       mol_type = protein
                       organism = Mus musculus
SEQUENCE: 30
MVTHSKFPAA GMSRPLDTSL RLKTFSSKSE YQLVVNAVRK LQESGFYWSA VTGGEANLLL    60
SAEPAGTFLI RDSSDQRHFF TLSVKTQSGT KNLRIQCEGG SFSLQSDPRS TQPVPRFDCV   120
LKLVHHYMPP PGTPSFSLPP TEPSSEVPEQ PPAQALPGST PKRAYYIYSG GEKIPLVLSR   180
PLSSNVATLQ HLCRKTVNGH LDSYEKVTQL PGPIREFLDQ YDAPL                   225

SEQ ID NO: 31          moltype = DNA  length = 678
FEATURE                Location/Qualifiers
source                 1..678
                       mol_type = other DNA
                       organism = Mus musculus
SEQUENCE: 31
atggtcaccc acagcaagtt tcccgccgcc gggatgagcc gccccctgga caccagcctg    60
cgcctcaaga ccttcagctc caaaagcgag taccagctgg tggtgaacgc cgtgcgcaag   120
ctgcaggaga gcggattcta ctggagcgca gtgaccggcg cgaggcgaaa cctgctgctc   180
agcgccgagc ccgcgggcac ctttcttatc cgcgacagct cggaccagcg ccacttcttc   240
acgttgagcg tcaagaccca gtcggggacc aagaacctac gcatccagtg tgaggggggc   300
agcttttcgc tgcagagtga cccccgaagc acgcagccag tccccgctt cgactgtgta    360
ctcaagctgg tgcaccacta catgccgctt ccagggccca cctcctttc tttgccacct    420
acggaaccct cgtccgaagt tccggagcag ccacctgccc aggcactccc cgggagtacc   480
cccaagagag cttactacat ctattctggg ggcgagaaga ttccgctggt actgagccga   540
cctctctcct ccaacgtggc cacctcag catctttgtc ggaagactgt caacggccac    600
ctggactcct atgagaaagt gacccagctg cctggaccca ttcgggagtt cctggatcag   660
tatgatgctc cactttaa                                                678

SEQ ID NO: 32          moltype = AA  length = 387
FEATURE                Location/Qualifiers
source                 1..387
                       mol_type = protein
                       organism = Homo sapiens
SEQUENCE: 32
MPTTIEREFE ELDTQRRWQP LYLEIRNESH DYPHRVAKFP ENRNRNRYRD VSPYDHSRVK    60
LQNAENDYIN ASLVDIEEAQ RSYILTQGPL PNTCCHFWLM VWQQKTKAVV MLNRIVEKES   120
VKCAQYWPTD DQEMLFKETG FSVKLLSEDV KSYYTVHLLQ LENINSGETR TISHFHYTTW   180
PDFGVPESPA SFLNFLFKVR ESGSLNPDHG PAVIHCSAGI GRSGTFSLVD TCLVLMEKGD   240
DINIKQVLLN MRKYRMGLIQ TPDQLRFSYM AIIEGAKCIK GDSSIQKRWK ELSKEDLSPA   300
FDHSPNKIMT EKYNGNRIGL EEEKLTGDRC TGLSSKMQDT MEENSESALR KRIREDRKAT   360
TAQKVQQMKQ RLNENERKRK RPRLTDT                                      387

SEQ ID NO: 33          moltype = DNA  length = 1721
FEATURE                Location/Qualifiers
source                 1..1721
                       mol_type = other DNA
                       organism = Homo sapiens
SEQUENCE: 33
gctcgggcgc cgagtctgcg cgctgacgtc cgacgctcca ggtactttcc ccacggccga    60
cagggcttgg cgtgggggcg gggcgcggcg cagcgcgc atgcgccgca gcgcagcgc    120
tctccccgga tcgtgcgggg cctgagcctc tccgccggcg caggtctgc tcgcgccagc    180
tcgctcccgc agccatgccc accaccatcg agcgggagtt cgaagagttg atactcagc    240
gtcgcggca gcgcgtgtac ttggaaattc gaaatgagtc ccatgactat cctcatagag   300
tggccaagtt tccagaaaac agaaatcgaa acagatacag agatgtaagc ccatatgatc   360
acagtcgtgt taaactgcaa aatgctgaga atgattatat taatgccagt ttagttgaca   420
tagaagaggc acaaaggagt tacatcttaa cacagggtcc acttcctaac acatgctgcc   480
atttctggct tatggtttgg cagcagaaga ccaaagcagt tgtcatgctg aaccgcattg   540
tggagaaaga atcggtaaaa tgtgcacagt actggccaac agatgaccaa gagatgctgt   600
```

```
ttaaagaaac aggattcagt gtgaagctct tgtcagaaga gtgaagtcg tattatacag    660
tacatctact acaattagaa aatatcaata gtggtgaaac cagaacaata tctcactttc    720
attatactac ctggccagat tttggagtcc ctgaatcacc agcttcattt ctcaatttct    780
tgtttaaagt gagagaatct ggctccttga accctgacca tgggcctgcg gtgatccact    840
gtagtgcagg cattgggcgc tctggcacct tctctctgat agacacttgt cttgttttga    900
tggaaaagg agatgatatt aacataaaac aagtgttact gaacatgaga aaataccgaa    960
tgggtcttat tcagacccca gatcaactga gattctcata catggctata atagaaggag   1020
caaaatgtat aagggagat tctagtatac agaaacgatg gaagaactt tctaggaag    1080
acttatctcc tgcctttgat cattccacaa acaaaatgat gactgaaaaa tacaatggga   1140
acagaatagg tctagaagaa gaaaaactga caggtgaccg atgtacagga ctttcctcta   1200
aaatgcaaga tacaatggag gagaacagtg agagtgctct acggaaacgt attcgagagg   1260
acagaaaggc caccacagct cagaaggtgc agcagatgaa acagaggcta aatgagaatg   1320
aacgaaaaag aaaaaggcca agattgacag acacctaata ttcatgactt gagatattcc   1380
tgcagctata aattttgaac cattgatgtg caaagcagca cctgaagccc actccggaaa   1440
ctaaagtgag gctcgctaac cctctagatt gcctcacagt tgtttgttta caaagtaaac   1500
tttacatcca ggggatgaag agcacccacc agcagaagac tttgcagaac cttaattgg    1560
atgtgttaag tgttttaat gagtgtatga aatgtagaaa gatgtacaag aaataaatta   1620
ggggagatta ctttgtattg tactgccatt cctactgtaa tttatactt tttggcagca   1680
ttaaatattt ttgttaaata gtcaaaaaaa aaaaaaaaa a                        1721

SEQ ID NO: 34            moltype = AA   length = 382
FEATURE                  Location/Qualifiers
source                   1..382
                         mol_type = protein
                         organism = Mus musculus
SEQUENCE: 34
MSATIEREFE ELDAQCRWQP LYLEIRNESH DYPHRVAKFP ENRNRNRYRD VSPYDHSRVK     60
LQSTENDYIN ASLVDIEEAQ RSYILTQGPL PNTCCHFWLM VWQQKTKAVV MLNRTVEKES    120
VKCAQYWPTD DREMVFKETG FSVKLLSEDV KSYYTVHLLQ LENINTGETR TISHFHYTTW    180
PDFGVPESPA SFLNFLFKVR ESGCLTPDHG PAVIHCSAGI GRSGTFSLVD TCLVLMEKGE    240
DVNVKQLLLN MRKYRMGLIQ TPDQLRFSYM AIIEGAKYTK GDSNIQKRWK ELSKEDLSPI    300
CDHSQNRVMV EKYNGKRIGS EDEKLTGLPS KVQDTVEESS ESILRKRIRE DRKATTAQKV    360
QQMKQRLNET ERKRKRPRLT DT                                            382

SEQ ID NO: 35            moltype = DNA   length = 1149
FEATURE                  Location/Qualifiers
source                   1..1149
                         mol_type = other DNA
                         organism = Mus musculus
SEQUENCE: 35
atgagcgcca ctattgagcg ggagttcgag gaactggacg cccagtgtag atggcagccc     60
ctttatcttg agatacgcaa cgaaagtcac gattaccctc ataggggtagc taaattccct    120
gagaacagaa acagaaaccg ctaccgcgat gtgtcaccct acgatcactc cagagtgaaa    180
cttcaaagta ccgaaaatga ttatataaat gccagcttgg tggacataga ggaagcccaa    240
agatcataca tacttactca agggcctctc ccaaacactt gttgccattt ctggctcatg    300
gtgtgggcaac agaagaccaa ggctgtggta atgctcaatc ggactgtgga aaagagtca    360
gtaaagtgtg ctcaatattg gccaactgat gataggagag tgtcttttaa ggaaacaggt    420
ttctccgtta agttgctcag tgaggatgtg aagtccattt acacagtaca tcttctccaa    480
ttggagaaca tcaacaccgg tgaaacccga acaatatccc actttcatta taccacttgg    540
cctgacttcg gtgttcctga agccccgct tcttttctca atttcctgtt taaggtgcgg    600
gagtcaggct gtctcacccc agatcatggg cctgctgtaa tacattgtag cgctgggatc    660
gggcgatccg ggacattctc ttttggtagac acttgcctgg tcctgatgga aagggagag    720
gacgtaaacg ttaagcagtt gctcctgaat atgagaaaat atcgaatggg gttgattcag    780
actcccgatc aacttagatt ctcttatatg gctataatcg agggcgcaaa atataccaag    840
ggggactcca acattcaaaa aagatggaag gagctctcta aggaagatct gtctccaatc    900
tgtgaccaca gtcagaaccg agttatggta gagaaataca cggtaaaag aattggctca    960
gaagacgaaa aactgaccgg actccctcc aaagtgcaag atacagtcga gaatcatcc    1020
gagtcaatct tgaggaaaag aatcagggaa gatcggaagg ccactacagc ccaaaagtg    1080
caacaaatga acagcgact caacgaaaca gagcggaaac gaaaacggcc aagactgaca   1140
gacacctaa                                                           1149

SEQ ID NO: 36            moltype = AA   length = 769
FEATURE                  Location/Qualifiers
REGION                   1..769
                         note = Description of Artificial Sequence: Synthetic
                          polypeptide
source                   1..769
                         mol_type = protein
                         organism = synthetic construct
SEQUENCE: 36
MAQWNQLQQL DTRYLEQLHQ LYSDSFPMEL RQFLAPWIES QDWAYAASKE SHATLVFHNL     60
LGEIDQQYSR FLQESNVLYQ HNLRRIKQFL QSRYLEKPME IARIVARCLW EESRLLQTAA    120
TAAQQGGQAN HPTAAVVTEK QQMLEQHLQD VRKRVQDLEQ KMKVVENLQD DFDFNYKTLK    180
SQGDMQDLNG NNQSVTRQKM QQLEQMLTAL DQMRRSIVSE LAGLLSAMEY VQKTLTDEEL    240
ADWKRRQQIA CIGGPPNICL DRLENWITSL AESQLQTRQQ IKKLEELQQK VSYKGDPIVQ    300
HRPMLEERIV ELFRNLMKSA FVVERQPCMP MHPDRPLVIK TGVQFTTKVR LLVKFPELNY    360
QLKIKVCIDK DSGDVAALRG SRKFNILGTN TKVMNNEESN NGSLSAEFKH LTLREQRCGN    420
GGRANCDASL IVTEELHLIT FETEVYHQGL KIDLETHSLP VVVISNICQM PNAWASILWY    480
NMLTNNPKNV NFFTKPPIGT WDQVAEVLSW QFSSTTKRGL SIEQLTTLAE KLLGPGVNYS    540
```

```
GCQITWAKFC KENMAGKGFS FWVWLDNIID LVKKYILALW NEGYIMGFIS KERERAILST    600
KPPGTFLLRF SESSKEGGVT FTWVEKDISG KTQIQSVEPY TKQQLNNMSF  AEIIMGYKIM   660
DATNILVSPL VYLYPDIPKE EAFGKYCRPE SQEHPEADPG AAPFLKTKFI  CVTPTTCSNT   720
IDLPMSPRTL DSLMQFGNNG EGAEPSAGGQ FESLTFDMEL TSECATSPM               769

SEQ ID NO: 37           moltype = DNA  length = 2310
FEATURE                 Location/Qualifiers
misc_feature            1..2310
                        note = Description of Artificial Sequence: Synthetic
                        polynucleotide
source                  1..2310
                        mol_type = other DNA
                        organism = synthetic construct
SEQUENCE: 37
atggcccaat ggaatcagct acagcagctt gacacacggt acctggagca gctccatcag    60
ctctacagtg acagcttccc aatggagctg cggcagtttc tggccccttg gattgagagt   120
caagattggg catatgcggc cagcaaagaa tcacatgcca ctttggtgtt tcataatctc   180
ctgggagaga ttgaccagca gtatagccgc ttcctgcaag agtcgaatgt tctctatcag   240
cacaatctac gaagaatcaa gcagtttctt cagagcaggt atcttgagaa gccaatggag   300
attgcccgga ttgtggcccg gtgcctgtgg gaagaatcac gccttctaca gactgcagcc   360
actgcggccc agcaaggggg ccaggccaac caccccacag cagccgtggt gacggagaag   420
cagcagatgc tggagcagca cctttcaggat gtccggaaga gagtgcagga tctagaacag   480
aaaatgaaag tggtagagaa tctccaggat gactttgatt tcaactataa aaccctcaag   540
agtcaaggag acatgcaaga tctgaatgga acaaccagt cagtgaccag gcagaagatg   600
cagcagctgg aacagatgct cactgcgctg gaccagatgc ggagaagcat cgtgagtgag   660
ctggcgggga ttttgtcagc gatggagtac gtgcagaaaa ctctcacgga cgaggagctg   720
gctgactgga gaggcggca  acagattgcc tgcattggag ccgcccaa catctgccta    780
gatcggctag aaaactggat aacgtcatta gcagaatctc aacttcagac ccgtcaacaa    840
attaagaaac tggaggagtt gcagcaaaaa gtttcctaca aggggaccc  cattgtacag    900
caccggccga tgctggagaa gagaatcgtg gagctgttta gaaacttaat gaaaagtgtg    960
tttgtggtgg agcggcagcc ctgcatgccc atgcatcctg accggcccct cgtcatcaag   1020
accggcgtcc agttcactac taaagtcagg ttgctggtca aattccctga gttgaattat   1080
cagcttaaaa ttaaagtgtg cattgacaaa gactctgggg acgttgcagc tctcagagga   1140
tcccggaaat ttaacattct gggcacaaac acaaaagtga tgaacatgga agaatccaac   1200
aacggcagcc tctctgcaga attcaaacac ttgaccctga gggagcagag atgtgggaat   1260
gggggccgag ccaattgtga tgcttccctg attgtgactg aggagctgca cctgatcacc   1320
tttgagaccg aggtgtatca ccaaggcctc aagattgacc tagagcccca ctccttgcca   1380
gttgtggtga tctccaacat ctgtcagatg ccaaatgcct gggcgtccat cctgtggtac   1440
aacatgctga ccaacaatcc caagaatgta aacttttttta ccaagccccc aattggaacc   1500
tgggatcaag tggccgaggt cctgagctgg cagttctcct ccaccaccaa gcgaggactg   1560
agcatcgagc agctgactac actggcagag aaacttttgg gacctggtgt gaattattca   1620
gggtgtcaga tcacatgggc taaattttgc aaagaaaaca tggctggcaa gggcttctcc   1680
ttctgggtct ggctggacaa tatcattgac cttgtgaaaa agtacatcct ggcccttttg    1740
aacgaaggt  acatcatggg ctttatcagt aaggagcggg agcgggccat cttgagcact   1800
aagcctccag gcaccttcct gctaagattc agtgaaagca gaaagaagg  aggcgtcact   1860
ttcacttggg tggagaagga catcagcggt aagacccaga tccagtccgt ggaaccatac   1920
acaaagcagc agctgaacaa catgtcattt gctgaaatca tcatgggcta taagatcatg   1980
gatgctacca atatcctggt gtctccactg gtctatctct atcctgacat tcccaaggag   2040
gaggcattcg gaaagtattg tcggccagag agccaggagc atcctgaagc tgacccaggc   2100
gctgccccat tcctgaagac caagttttatc tgtgtgacac caacgacctg cagcaatacc   2160
attgacctgc cgatgtcccc ccgcacttta gattcattga tgcagttttgg aaataatggt   2220
gaaggtgctg aaccctcagc aggagggcag tttgagtccc tcacctttga catggagttg   2280
acctcggagt gcgctacctc ccccatgtga                                    2310

SEQ ID NO: 38           moltype = AA  length = 769
FEATURE                 Location/Qualifiers
REGION                  1..769
                        note = Description of Artificial Sequence: Synthetic
                        polypeptide
source                  1..769
                        mol_type = protein
                        organism = synthetic construct
SEQUENCE: 38
MAQWNQLQQL DTRYLEQLHQ LYSDSFPMEL RQFLAPWIES QDWAYAASKE SHATLVFHNL    60
LGEIDQQYSR FLQESNVLYQ HNLRRIKQFL QSRYLEKPME IARIVARCLW EESRLLQTAA   120
TAAQQGGQAN HPTAAVVTEK QQMLEQHLQD VRKRVQDLEQ KMKVVENLQD DFDFNYKTLK   180
SQGDMQDLNG NNQSVTRQKM QQLEQMLTAL DQMRRSIVSE LAGLLSAMEY VQKTLTDEEL   240
ADWKRRQQIA CIGGPPNICL DRLENWITSL AESQLQTRQQ IKKLEELQQK VSYKGDPIVQ   300
HRPMLEERIV ELFRNLMKSA FVVERQPCMP MHPDRPLVIK TGVQFTTKVR LLVKFPELNY   360
QLKIKVCIDK DSGDVAALRG SRKFNILGTN TKVMNMEESN NGSLSAEFKH LTLREQRCGN   420
GGRANCDASL IVTAALHLIT FETEVYHQGL KIDLETHSLP VVVISNICQM PNAWASILWY   480
NMLTNNPKNV NFFTKPPIGT WDQVAEVLSW QFSSTTKRGL SIEQLTTLAE KLLGPGVNYS   540
GCQITWAKFC KENMAGKGFS FWVWLDNIID LVKKYILALW NEGYIMGFIS KERERAILST   600
KPPGTFLLRF SESSKEGGVT FTWVEKDISG KTQIQSVEPY TKQQLNNMSF AEIIMGYKIM   660
DATNILVSPL VYLYPDIPKE EAFGKYCRPE SQEHPEADPG AAPYLKTKFI CVTPTTCSNT   720
IDLPMSPRTL DSLMQFGNNG EGAEPSAGGQ FESLTFDMEL TSECATSPM               769

SEQ ID NO: 39           moltype = DNA  length = 2310
FEATURE                 Location/Qualifiers
```

| misc_feature | 1..2310 |
| | note = Description of Artificial Sequence: Synthetic polynucleotide |
| source | 1..2310 |
| | mol_type = other DNA |
| | organism = synthetic construct |

SEQUENCE: 39

```
atggcccaat ggaatcagct acagcagctt gacacacggt acctggagca gctccatcag   60
ctctacagtg acagcttccc aatggagctg cggcagtttc tggcccccttg gattgagagt  120
caagattggg catatgcggc cagcaaagaa tcacatgcca ctttggtgtt tcataatctc  180
ctgggagaga ttgaccagca gtatagccgc ttcctgcaag agtcgaatgt tctctatcag  240
cacaatctac gaagaatcaa gcagtttctt cagagcaggt atcttgagaa gccaatggag  300
attgcccgga ttgtggcccg gtgcctgtgg aagaatcac gccttctaca gactgcagcc   360
actgcgggcc agcaagggg ccaggccaac caccccacaa cagccgtggt gacggagaag   420
cagcagatgc tggagcagca ccttcaggat gtccggaaga gagtgcagga tctagaacag  480
aaaatgaaag tggtagagaa tctccaggat gactttgatt tcaactataa aaccctcaag  540
agtcaaggag acatgcaaga tctgaatgga acaaccagt cagtgaccag gcagaagatg   600
cagcagctgg aacagatgct cactgcgctg accagatgc ggagaagcat cgtgagtgag   660
ctggcgggc ttttgtcagc gatggagtac gtgcagaaaa ctctcacgga cgaggagctg   720
gctgactgga gaggcggca acagattgcc tgcattggag gcccgcccaa catctgccta   780
gatcggctag aaaactggat aacgtcatta gcagaatctc aacttcagac ccgtcaacaa  840
attaagaaac tggaggagtt gcagcaaaaa gtttcctaca aaggggaccc cattgtacag  900
caccggccga tgctggagga gagaatcgtg gagctgttta gaaacttaat gaaaagtgcc  960
tttgtggtgg agcggcagcc ctgcatgccc atgcatcctg accggcccct cgtcatcaag 1020
accggcgtcc agttcactac taaagtcagg ttgctggtca aattccctga gttgaattat 1080
cagcttaaaa ttaaagtgtg cattgacaaa gactctgagg acgttgcagc tctcagagga 1140
tcccggaaat taacattct gggcacaaac acaaagtga tgaacatgga agaatccaac  1200
aacggcagcc tctctgcaga attcaaaac ttgaccctga gggagcagag atgtgggaat  1260
gggggccgag ccaattgtga tgcttccctg attgtgactg cggcgctgca cctgatcacc  1320
tttgagaccg aggtgtatca ccaaggcctc aagattacc tagagaccca ctccttgcca  1380
gttgtggtga tctccaacat ctgtcagatg ccaaatgcct gggcgtccat cctgtggtac  1440
aacatgctga ccaacaatcc caagaatgta aacttttta ccaagcccc aattggaacc   1500
tgggatcaag tggccgaggt cctgagctgg cagttctcct ccaccaccaa gcgaggactg  1560
agcatcgagc agctgactac actggcagag aaactcttgg gacctggtgt gaattattca  1620
gggtgtcaga tcacatgggg taaatttgc aaagaaaaca tggctggcaa gggcttctcc  1680
ttctgggtct ggctggacaa tatcattgac cttgtgaaaa agtacatcct ggcccttgg   1740
aacgaagggt acatcatggg ctttatcagt aaggagcggg agcgggccat cttgagcact  1800
aagcctccag gcaccttcct gctaagattc agtgaaagca gcaaagaagg aggcgtcact  1860
ttcacttggg tggagaagga catcagcggt aagaccccag tccagtccgt ggaaccatac  1920
acaaagcagc agctgaacaa catgtcattt gctgaaatca tcatgggcta taagatcatg  1980
gatgctacca atatcctggt gtccactg gtctatctct atcctgacat tcccaaggag   2040
gaggcattcg gaaagtattg tcggccagag agccaggagc atcctgaagc tgacccaggc  2100
gctgccccat acctgaagac caagttttatc tgtgtgacaa ccacgacctg caataacc   2160
attgacctgc cgatgtcccc ccgcacttta gattcattga tgcagtttgg aaataatggt  2220
gaaggtgctg aaccctcagc aggagggcag tttgagtccc tcacctttga catggagttg  2280
acctcggagt gcgctacctc ccccatgtga                                      2310
```

| SEQ ID NO: 40 | moltype = DNA length = 372 |
| FEATURE | Location/Qualifiers |
| source | 1..372 |
| | mol_type = other DNA |
| | organism = Homo sapiens |

SEQUENCE: 40

```
atggaagatg gatcctggtg cccaatgaaa cccaagaagg aggcatctga ggtttgcccc   60
ccgccagggt atgggctgga tggcctccag tacagccag tccaggggg agatccatca   120
gagaataaga agaaggtcga agttattgac ttgacaatag aaagctcatc agatgaggag  180
gatctgcccc ctaccaagaa gcactgttct gtcacctcag ctgccatccc ggccctacct  240
ggaagcaaag gagtcctgac atctggccac cagccatcct cggtgctaag gagccctgct  300
atgggcacgt gggtggga tttcctgtcc agtctcccac tacatgagta cccacctgcc   360
ttcccactgg ga                                                         372
```

| SEQ ID NO: 41 | moltype = DNA length = 420 |
| FEATURE | Location/Qualifiers |
| misc_feature | 1..420 |
| | note = Description of Artificial Sequence: Synthetic polynucleotide |
| source | 1..420 |
| | mol_type = other DNA |
| | organism = synthetic construct |

SEQUENCE: 41

```
atggaagatg gatcctggtg cccaatgaaa cccaagaagg aggcatctga ggtttgcccc   60
ccgccagggt atgggctgga tggcctccag tacagcccag tccaggggg agatccatca   120
gagaataaga agaaggtcga agttattgac ttgacaatag aaagctcatc agatgaggag  180
gatctgcccc ctaccaagaa gcactgttct gtcacctcag ctgccatccc ggccctacct  240
ggaagcaaag gagtcctgac atctggccac cagccatcct cggtgctaag gagccctgct  300
atgggcacgt gggtggga tttcctgtcc agtctcccac tacatgagta cccacctgcc   360
ttcccactgg gaaggcggcg aagacgccgc aggagacggc accaccatca ccatcactaa  420
```

| SEQ ID NO: 42 | moltype = DNA length = 378 |

```
FEATURE            Location/Qualifiers
source             1..378
                   mol_type = other DNA
                   organism = Mus musculus
SEQUENCE: 42
atggaagatg gatcctggtg tccgatgaaa cccaagaagg aggcatcaga ggtttgcccc   60
ccgccagggt atgggctgga tggtctccag tacagcgcag tccaggaggg aattcagcca  120
gagagtaaga agagggtcga agtcattgac ttgaccatcg aaagctcatc agatgaggag  180
gatttgcccc ccaccaagaa gcactgccct gtcacctcag cggccattcc agcccttcct  240
ggaagcaaag gagccctgac ctctggtcac cagccatcct cggtgctgcg gagccctgca  300
atgggcacac tgggcagtga cttcctgtct agtctcccgc tacatgagta cccacctgcc  360
ttcccactgg ggcgacga                                                378

SEQ ID NO: 43       moltype = DNA  length = 420
FEATURE             Location/Qualifiers
misc_feature        1..420
                    note = Description of Artificial Sequence: Synthetic
                    polynucleotide
source              1..420
                    mol_type = other DNA
                    organism = synthetic construct
SEQUENCE: 43
atggaagatg gatcctggtg tccgatgaaa cccaagaagg aggcatcaga ggtttgcccc   60
ccgccagggt atgggctgga tggtctccag tacagcgcag tccaggaggg aattcagcca  120
gagagtaaga agagggtcga agtcattgac ttgaccatcg aaagctcatc agatgaggag  180
gatttgcccc ccaccaagaa gcactgccct gtcacctcag cggccattcc agcccttcct  240
ggaagcaaag gagccctgac ctctggtcac cagccatcct cggtgctgcg gagccctgca  300
atgggcacac tgggcagtga cttcctgtct agtctcccgc tacatgagta cccacctgcc  360
ttcccactgg ggcgacgaag gcggcgaaga cggaggcggc atcaccatca tcaccactaa  420
```

ONCOLYTIC VIRUSES TARGETING STAT3

CROSS-REFERENCE

The instant application is a Divisional of U.S. application Ser. No. 17/574,763, filed Jan. 13, 2022, now abandoned, and is a Divisional of U.S. application Ser. No. 17/574,691, filed Jan. 13, 2022, now abandoned, which are Divisional Applications of U.S. application Ser. No. 16/252,338, filed Jan. 18, 2019, issued as U.S. Pat. No. 11,253,559, on Feb. 22, 2022, which is a Continuation of International Application No. PCT/US2017/042910, filed Jul. 19, 2017, which claims the benefit of U.S. Provisional Application No. 62/364,095, filed Jul. 19, 2016, to each of which priority is claimed and the contents of each of which are incorporated herein by reference in their entireties.

INCORPORATION BY REFERENCE

All publications, patents, patent applications, and NCBI accession numbers mentioned in this specification are herein incorporated by reference to the same extent as if each individual publication, patent, or patent application was specifically and individually indicated to be incorporated by reference, and as if set forth in their entireties. In the event of a conflict between a term as used herein and the term as defined in the incorporated reference, the definition of this disclosure controls.

GRANT INFORMATION

This disclosure was made with government support under CA178766 awarded by the National Institutes of Health. The government has certain rights in the disclosure.

SEQUENCE LISTING

The instant application contains a Sequence Listings, which has been submitted in XML format via EFS-Web and is hereby incorporated by reference in its entirety. Said XML copy, created on Aug. 18, 2023, is named 072396_0984_SL.XML, and is 62,838 bytes in size.

INTRODUCTION

Embodiments herein relate to oncolytic viruses that can modulate STAT3 (signal transducer and activator of transcription 3)-mediated gene activation.

SUMMARY

Provided herein in one embodiment is an oncolytic vaccinia virus which can comprise an exogenous nucleic acid, wherein said exogenous nucleic acid can encode a protein or a fragment thereof that can modulate STAT3-mediated gene-activation. In certain embodiments, the exogenous nucleic acid can encode the protein. In certain embodiments, the exogenous nucleic acid can encode the fragment.

In certain embodiments, the protein or the fragment thereof can comprise a STAT3 recognition domain or a blocking fragment within said recognition domain. In certain embodiments, the oncolytic vaccinia virus can comprise the blocking fragment, wherein the blocking fragment can modulate STAT3-mediated gene activation.

In certain embodiments, the protein or the fragment thereof can be a PIAS3 protein or a fragment thereof. In certain embodiments, the protein or the fragment thereof can be a SOCS3 protein or a fragment thereof, a TCPTP protein or a fragment thereof, or a STAT3 protein or a fragment thereof.

In certain embodiments, the protein or the fragment thereof can be a PIAS3 protein or a fragment thereof. In certain embodiments, the exogenous nucleic acid can be codon optimized for increased expression of the PIAS3 protein or the fragment thereof, the SOCS3 protein or a fragment thereof, the TCPTP protein or the fragment thereof, or the dominant-negative mutant STAT3 protein or the fragment thereof. In certain embodiments, the exogenous nucleic acid can encode the PIAS3 protein, wherein the exogenous nucleic acid can be at least about 85%, at least about 90%, at least about 95%, at least about 96%, at least about 97%, at least about 98%, at least about 99%, or 100% homologous to a nucleic acid sequence selected from the group consisting of SEQ ID NOs: 8-10 and 40-43. In certain embodiments, the exogenous nucleic acid can encode the PIAS3 protein, wherein the exogenous nucleic acid can comprise a nucleotide sequence selected from the group consisting of SEQ ID NOs: 8-10 and 40-43. In certain embodiments, the exogenous nucleic acid coding for the PIAS3 protein, wherein the exogenous nucleic acid can be at least about 85%, at least about 90%, at least about 95%, at least about 96%, at least about 97%, at least about 98%, at least about 99%, or 100% homologous to the entire length of a nucleic acid sequence selected from the group consisting of SEQ ID NOs: 8-10 and 40-43. In certain embodiments, the exogenous nucleic acid can encode the PIAS3 protein, wherein the exogenous nucleic acid can be at least about 85%, at least about 90%, at least about 95%, at least about 96%, at least about 97%, at least about 98%, at least about 99%, or 100% homologous to a fraction of a nucleic acid sequence selected from the group consisting of SEQ ID NOs: 8-10 and 40-43. In certain embodiments, the exogenous nucleic acid can encode the PIAS3 protein fragment, wherein the exogenous nucleic acid can be at least about 85%, at least about 90%, at least about 95%, at least about 96%, at least about 97%, at least about 98%, at least about 99%, or 100% homologous to a nucleic acid fragment of a nucleotide sequence selected from the group consisting of SEQ ID NOs: 8-10 and 40-43. In certain embodiments, the exogenous nucleic acid can encode the PIAS3 protein fragment, wherein the exogenous nucleic acid comprises a nucleic acid fragment of a nucleotide sequence that can be selected from of the group consisting of SEQ ID NOs: 8-10 and 40-43. In certain embodiments, the nucleic acid fragment can comprise a contiguous stretch of nucleotides from a nucleotide sequence selected from the group consisting of SEQ ID NOs: 8-10 and 40-43. In certain embodiments, the contiguous stretch of nucleotides can have a length from 3 nucleotides to 552 nucleotides. In certain embodiments, the nucleic acid fragment can comprise a non-contiguous nucleotides from a nucleotide sequence selected from the group consisting of SEQ ID NOs: 8-10 and 40-43.

In certain embodiments, the exogenous nucleic acid coding for the PIAS3 protein, wherein the PIAS3 protein comprises an amino acid sequence that can be at least about 85%, at least about 90%, at least about 95%, at least about 96%, at least about 97%, at least about 98%, at least about 99%, or 100% homologous to an amino acid sequence selected from the group consisting of SEQ ID NOs: 1-7 and 24-27 and conservative substitutions thereof. In certain embodiments, the exogenous nucleic acid coding for the PIAS3 protein, wherein the PIAS3 protein can comprise an amino acid sequence that is at least about 85%, at least about 90%, at least about 95%, at least about 96%, at least about 97%, at least about 98%, at least about 99%, or 100% homologous to the amino acid sequence of SEQ ID NO: 1 and conservative substitutions thereof. In certain embodiments, the exogenous nucleic acid can encode the PIAS3 protein, wherein the PIAS3 protein can comprise an amino acid sequence that can be at least about 85%, at least about 90%, at least about 95%, at least about 96%, at least about 97%, at least about 98%, at least about 99%, or 100% homologous to the entire length of an amino acid sequence selected from the group consisting of SEQ ID NOs: 1-7 and 24-27 and conservative substitutions thereof. In certain embodiments, the exogenous nucleic acid can encode the PIAS3 protein, wherein the PIAS3 protein can comprise an amino acid sequence that is at least about 85%, at least about 90%, at least about 95%, at least about 96%, at least about 97%, at least about 98%, at least about 99%, or 100% homologous to the entire length of the amino acid sequence of SEQ ID NO: 1 and conservative substitutions thereof. In certain embodiments, the exogenous nucleic acid can encode the PIAS3 protein, wherein the PIAS3 protein can comprise an amino acid sequence that is at least about 85%, at least about 90%, at least about 95%, at least about 96%, at least about 97%, at least about 98%, at least about 99%, or 100% homologous to a fraction of the entire length of an amino acid sequence selected from the group consisting of SEQ ID NOs: 1-7 and 24-27 and conservative substitutions thereof. In certain embodiments, the exogenous nucleic acid can encode the PIAS3 protein, wherein the PIAS3 protein can comprise an amino acid sequence that can be at least about 85%, at least about 90%, at least about 95%, at least about 96%, at least about 97%, at least about 98%, at least about 99%, or 100% homologous to a fraction of the entire length of the amino acid sequence of SEQ ID NO: 1 and conservative substitutions thereof. In certain embodiments, the exogenous nucleic acid coding for the PIAS3 protein fragment, wherein the PIAS3 protein fragment can comprise an amino acid sequence that can be at least about 85%, at least about 90%, at least about 95%, at least about 96%, at least bout 97%, at least about 98%, at least about 99%, or 100% homologous to an amino acid fragment from any one of SEQ ID NOs: 1-7 and 24-27 and conservative substitutions thereof. In certain embodiments, the exogenous nucleic acid can encode the PIAS3 protein fragment, wherein the PIAS3 protein fragment can comprise an amino acid sequence that can be at least about 85%, at least about 90%, at least about 95%, at least about 96%, at least about 97%, at least about 98%, at least about 99%, or 100% homologous to an amino acid fragment from SEQ ID NO: 1 and conservative substitutions thereof. In certain embodiments, the PIAS3 protein or a fragment thereof encoded by an exogenous nucleic acid disclosed herein can comprise amino acids 400-528 of the amino acid sequence of SEQ ID NO: 1 and conservative substitutions thereof. In certain embodiments, the PIAS3 protein or a fragment thereof encoded by an exogenous nucleic acid disclosed herein can comprise amino acids 400-523 of the amino acid sequence of SEQ ID NO: 6 and conservative substitutions thereof.

In certain embodiments, the protein or a fragment thereof that modulates STAT3 activity, e.g., modulate STAT3-mediated gene-activation, is a SOCS3 protein or a fragment thereof and conservative substitutions thereof. In certain embodiments, the SOCS3 protein or a fragment thereof can comprise a human SOCS3 protein or a fragment thereof and conservative substitutions thereof. In certain embodiments, the SOCS3 protein or the fragment thereof can comprise an amino acid sequence that can be at least about 85% homologous to an amino acid sequence selected from the group consisting of SEQ ID NOs: 28 and 30 and conservative substitutions thereof. In certain embodiments, the SOCS3 protein or the fragment thereof can comprise an amino acid sequence that can be at least about 85% homologous to the amino acid sequence of SEQ ID NO: 28 and conservative substitutions thereof. In certain embodiments, the SOCS3 protein or the fragment thereof can comprise an amino acid sequence that can be at least about 85% homologous to the entire length of an amino acid sequence selected from the group consisting of SEQ ID NOs: 28 and 30 and conservative substitutions thereof. In certain embodiments, the SOCS3 protein or the fragment thereof can comprise an amino acid sequence that can be at least about 85% homologous to a fraction of the entire length of an amino acid sequence selected from the group consisting of SEQ ID NOs: 28 and 30 and conservative substitutions thereof.

In certain embodiments, the protein or the fragment thereof that modulates STAT3 activity, e.g., modulate STAT3-mediated gene-activation, can be a TCPTP protein or a fragment thereof and conservative substitutions thereof. In certain embodiments, the TCPTP protein or the fragment thereof can be a human TCPTP protein or a fragment thereof and conservative substitutions thereof. In certain embodiments, the TCPTP protein or the fragment thereof can comprise an amino acid sequence that can be at least about 85% homologous to an amino acid sequence selected from the group consisting of SEQ ID NOs: 32 and 34 and conservative substitutions thereof. In certain embodiments, the TCPTP protein or the fragment thereof can comprise an amino acid sequence that can be at least about 85% homologous to the amino acid sequence of SEQ ID NO: 32 and conservative substitutions thereof. In certain embodiments, the TCPTP protein or the fragment thereof can comprise an amino acid sequence that can be at least about 85% homologous to the entire length of an amino acid sequence selected from the group consisting of SEQ ID NOs: 32 and 34 and conservative substitutions thereof. In certain embodiments, the TCPTP protein or portion thereof can comprise an amino acid sequence that can be at least about 85% homologous to a fraction of the entire length of an amino acid sequence selected from the group consisting of SEQ ID NOs: 32 and 34 and conservative substitutions thereof.

In certain embodiments, a protein or a fragment thereof that modulates STAT3 activity, e.g., modulate STAT3-mediated gene-activation, can be a dominant-negative mutant STAT3 protein or a fragment thereof and conservative substitutions thereof. In certain embodiments, the dominant-negative mutant STAT3 protein or the fragment thereof can be a human dominant-negative mutant STAT3 protein or a fragment thereof and conservative substitutions thereof. In certain embodiments, the dominant-negative mutant STAT3 protein or the fragment thereof can comprise an amino acid sequence that can be at least about 85% homologous to an amino acid sequence selected from the group consisting of SEQ ID NOs: 36 and 38 and conservative substitutions thereof. In certain embodiments, the dominant-negative mutant STAT3 protein or the fragment thereof can comprise an amino acid sequence that can be at least about 85% homologous to the entire length of an amino acid sequence selected from the group consisting of SEQ ID NOs: 36 and 38 and conservative substitutions thereof. In certain embodiments, the dominant-negative mutant STAT3 protein or the fragment thereof can comprise an amino acid sequence that can be at least about 85% homologous to a portion of the entire length of an amino acid sequence selected from the group consisting of SEQ ID NOs: 36 and 38 and conservative substitutions thereof.

In certain embodiments, the exogenous nucleic acid can be inserted into the vaccinia viral genome.

In certain embodiments, the exogenous nucleic acid can be inserted into the thymidine kinase locus of the vaccinia viral genome. In certain embodiments, the oncolytic vaccinia virus can be an extracellular enveloped virus (EEV). In certain embodiments, the oncolytic vaccinia virus can replicate within M2 macrophages in tumor cells. In certain embodiments, the oncolytic vaccinia virus can replicate within the M2 macrophages in tumor cells to produce a population of viruses that predominantly contains extracellular enveloped viruses (EEVs). In certain embodiments, the oncolytic vaccinia virus can partially avoid immunosuppression by replicating within the M2 macrophages.

The present disclosure further provides a pharmaceutical composition that can comprise an oncolytic vaccinia virus as described herein, and an excipient. In certain embodiments, the excipient can comprise one or more of a buffering agent, a stabilizer, an antioxidant, a binder, a diluent, a dispersing agent, a rate controlling agent, a lubricant, a glidant, a disintegrant, a plasticizer, a preservative, or any combination thereof. In certain embodiments, the excipient can comprise di-sodium hydrogen phosphate dihydrate, sodium dihydrogen phosphate dihydrate, sodium chloride, myo-inositol, sorbitol, or any combination thereof. In certain embodiments, the pharmaceutical compositions may not comprise a preservative. In certain embodiments, the pharmaceutical compositions can further comprise one or more of a preservative, a diluent, and a carrier. In certain embodiments, the pharmaceutical composition can further comprise an additional active ingredient or a salt thereof. In certain embodiments, the pharmaceutical compositions can comprise the additional active ingredient, wherein the additional active ingredient can be a further oncolytic vaccinia virus.

The present disclosure further provides a process for producing an oncolytic vaccinia virus as described herein, wherein the process can comprise the following steps: (i) generating a modified vaccinia virus DNA vector by operably linking a vaccinia virus base nucleic acid sequence to the exogenous nucleic acid sequence according as described above; (ii) transfecting mammalian cells with the modified vaccinia virus DNA vector; (iii) culturing the mammalian cells in conditions suitable for viral replication; and (iv) harvesting the viral particles. In certain embodiments, the mammalian cells comprise HeLa cells. 293 cells, or Vero cells. In certain embodiments, the exogenous nucleic acid in the modified vaccinia virus DNA vector can promote a population of viral particles predominantly containing extracellular enveloped viruses (EEV).

The present disclosure provides methods of treatment by administering one or more of the disclosed vaccinia viruses. In certain embodiments, a method of treating a cancer can comprise administering to a subject in need thereof a therapeutically effective amount of an oncolytic vaccinia virus according to this disclosure or a pharmaceutical composition as described herein. In some embodiment, the method can comprise the administration of a therapeutically effective amount of an oncolytic vaccinia virus according to this disclosure or a pharmaceutical composition as described herein, wherein the cancer can be a solid tumor, a leukemia, or a lymphoma.

One non-limiting embodiment provides a method of treating a tumor, wherein the method can comprise administering to a subject in need thereof a therapeutically effective amount of an oncolytic vaccinia virus according to this disclosure or a pharmaceutical composition as described herein. In certain embodiments, the method can comprise the administration of a therapeutically effective amount of an oncolytic vaccinia virus according to this disclosure or a pharmaceutical composition as described herein, wherein the tumor can be a solid tumor, a leukemia, or a lymphoma.

One non-limiting embodiment provides, a method of treating a cancer or a tumor, wherein the method can comprise administering to a subject in need thereof a therapeutically effective amount of an oncolytic vaccinia virus according to this disclosure or a pharmaceutical composition as described herein, in combination with a further therapy. In certain embodiments, the method can comprise administration of the further therapy, wherein the further therapy can comprise chemotherapy, radiation, oncolytic viral therapy with an additional virus, treatment with immunomodulatory proteins, a STAT3 inhibitor, an anti-cancer agent, or any combinations thereof. In certain embodiments, the method can comprise administration of the further therapy, wherein the further therapy can be administered concurrently or sequentially. In certain embodiments, the method can comprise sequential administration of the further therapy, wherein the further therapy can be administered prior to administering the oncolytic vaccinia virus according to this disclosure or a pharmaceutical composition as described herein. In certain embodiments, the method can comprise sequential administration of the further therapy, wherein the further therapy can be administered after administering the oncolytic vaccinia virus according to this disclosure or a pharmaceutical composition as described herein.

One non-limiting embodiment provides a method of at least partially re-sensitizing a cancer patient to a cancer therapy, wherein the method can comprise administering to a subject in need thereof a therapeutically effective amount of an oncolytic vaccinia virus according to this disclosure or a pharmaceutical composition as described herein, in combination with a drug that can enhance the replication of the vaccinia virus within tumor cells. In certain embodiments, the method can comprise the administration of the therapeutically effective amount of an oncolytic vaccinia virus according to this disclosure or a pharmaceutical composition as described herein, wherein the cancer therapy can comprise chemotherapy, radiation, viral therapy, treatment with immunomodulatory proteins, or any combinations thereof.

One non-limiting embodiment provides a method of producing a toxic effect in cancer cells, wherein the method can comprise administering to a population of cancer cells a therapeutically effective amount of an oncolytic vaccinia virus according to this disclosure or a pharmaceutical composition as described herein. In certain embodiments, the method can comprise the administration of the therapeutically effective amount of an oncolytic vaccinia virus according to this disclosure or a pharmaceutical composition as described herein, wherein not every cancer cell in the population of cancer cells can be infected with the oncolytic vaccinia virus. In certain embodiments, the growth of a non-infected cancer cell can be inhibited without direct infection One non-limiting embodiment provides, a method of determining the infectivity of an oncolytic vaccinia virus, wherein the method can comprise: (i) collecting a first biological sample from a subject and determining the level of STAT3 in the first biological sample; (ii) administering to the subject effective therapeutically effective amount of an oncolytic vaccinia virus according to this disclosure or a pharmaceutical composition as described herein, alone or in combination with a further therapy; (iii) collecting a second biological sample from the subject after about 2 hours to about 72 hours following the administration in step (ii) and detecting the level of a STAT3 protein in the second biological sample. In certain embodiments, the method can comprise administration of the further therapy, wherein the further therapy can comprise chemotherapy, radiation, oncolytic viral therapy with an additional virus, treatment with immunomodulatory proteins, a STAT3 inhibitor, an anticancer agent, or any combinations thereof. In certain embodiments, the method can comprise administration of the further therapy, wherein the further therapy can be administered concurrently or sequentially. In certain embodiments, the method can comprise sequential administration of the further therapy, wherein the further therapy can be administered prior to administering the oncolytic vaccinia virus according to this disclosure or a pharmaceutical composition as described herein. In certain embodiments, the method can comprise sequential administration of the further therapy, wherein the further therapy can be administered after administering the oncolytic vaccinia virus according to this disclosure or a pharmaceutical composition as described herein.

In certain embodiments, the method can comprise determining the level of STAT3 before (step i) and after (step iii) administration of the oncolytic vaccinia virus or the pharmaceutical composition, alone or in combination with a further therapy, wherein the oncolytic vaccinia virus can be determined to be infective when the level of STAT3 is lower in step (iii) than in step (i).

In certain embodiments, the method can comprise the administration of the oncolytic vaccinia virus according to this disclosure or a pharmaceutical composition as described herein, wherein the oncolytic vaccinia virus or the pharmaceutical composition can be administered at a dosage that can comprise about $10^6$ PFU/mL to about $10^8$ PFU/mL of the oncolytic vaccinia virus. In certain embodiments, the method can comprise the administration of the oncolytic vaccinia virus according to this disclosure or a pharmaceutical composition as described herein, wherein the oncolytic vaccinia virus or the pharmaceutical composition can be administered, independently, in an initial dose for a first period of time, an intermediate dose for a second period of time, and a high dose for a third period of time. In certain embodiments, the method can comprise administration of the initial, the intermediate, and the high dose, independently, wherein the initial dose can be lower than the intermediate dose and the intermediate dose is lower than the high dose. In certain embodiments, the first, second, and third periods of time can each be from about 1 week to about 3 weeks. In certain embodiments, the method can comprise administering the oncolytic vaccinia virus according to this disclosure or a pharmaceutical composition as described herein, wherein the oncolytic vaccinia virus and the pharmaceutical composition can independently comprise a liquid dosage form that can be administered at a volume of about 1 mL to about 5 mL, about 5 mL to 10 mL, about 15 mL to about 20 mL, about mL to about 30 mL, about 30 mL to about 50 mL, about 50 mL to about 100 mL, about 100 mL to 150 mL, about 150 mL to about 200 mL, about 200 mL to about 250 mL, about 250 mL to about 300 mL, about 300 mL to about 350 mL, about 350 mL to about 400 mL, about 400 mL to about 450 mL, about 450 mL to 500 mL, about 500 mL to 750 mL, or about 750 mL to 1000 mL. In certain embodiments, the method can comprise administering the oncolytic vaccinia virus according to this disclosure or a pharmaceutical composition as described herein, wherein the oncolytic vaccinia virus or the pharmaceutical composition can be administered in a liquid dosage form, a solid dosage form, an inhalable dosage form, an intranasal dosage form, in a liposomal formulation, a dosage form comprising nanoparticles, a dosage form comprising microparticles, a polymeric dosage form, or any combinations thereof. In certain embodiments, the method can comprise administering the oncolytic vaccinia virus according to this disclosure or a pharmaceutical composition as described herein, wherein the oncolytic vaccinia virus or the pharmaceutical composition can be administered for a duration of about 1 week, about 2 week, about 3 weeks, about 4 weeks, about 6 weeks, about 7 weeks, about 8 weeks, about 9 weeks, about 10, weeks, or about 12 weeks. In certain embodiments, the method can comprise administering the oncolytic vaccinia virus according to this disclosure or a pharmaceutical composition as described herein, wherein the oncolytic vaccinia virus or the pharmaceutical composition can be administered once daily, twice daily, once every week, once every two weeks, or once every three weeks. In certain embodiments, the method can comprise administering the oncolytic vaccinia virus according to this disclosure or a pharmaceutical composition as described herein, wherein the oncolytic vaccinia virus or the pharmaceutical composition can be administered intravenously or by an intratumoral injection. In certain embodiments, the method can comprise administering the oncolytic vaccinia virus according to this disclosure or a pharmaceutical composition as described herein, wherein the administration of the oncolytic vaccinia virus or the pharmaceutical composition can result in a first peak viral load after about 1 hour to about 3 days and a second peak viral load after about 3 days to about 7 days from administration of a first dose. In certain embodiments, the method can comprise administration of the further therapy, wherein the further therapy can be administered for a duration of about 1 week, about 2 week, about 3 weeks, about 4 weeks, about 6 weeks, about 7 weeks, about 8 weeks, about 9 weeks, about 10, weeks, or about 12 weeks. In certain embodiments, the method can comprise administration of the further therapy, wherein the further therapy can be administered once daily, once every week, once every two weeks, or once every three weeks. In certain embodiments, the method can comprise administration of the further therapy, wherein the further therapy can be administered in a liquid dosage form, a solid dosage form, an inhalable dosage form, an intranasal dosage form, in a liposomal formulation, a dosage form comprising nanoparticles, a dosage form comprising microparticles, a polymeric dosage form, or any combinations thereof. In certain embodiments, the method can comprise administration of the further therapy, wherein the further therapy can be administered orally, intravenously, by an intratumoral injection, or by radiation. In certain embodiments, the method can comprise the administration of the oncolytic vaccinia virus according to this disclosure or a pharmaceutical composition as described herein, to a subject in need thereof, wherein the subject can be human. In certain embodiments, the method can comprise collection of the first and the second biological samples from the subject, wherein the first and the second biological samples can be human tissue samples. In certain embodiments, the method can comprise collection of the first and the second biological samples from the subject, wherein the subject can be human and the first and the second biological samples can be blood or plasma from the human subject. In certain embodiments, the method can comprise the administration of the oncolytic vaccinia virus according to this disclosure, or the pharmaceutical composition as described herein, to the subject in need thereof, wherein prior to administration of the oncolytic vaccinia virus or the pharmaceutical composition the subject may have been diagnosed with a cancer or a tumor. In certain embodiments, the method can comprise the administration of the oncolytic vaccinia virus according to this disclosure or a pharmaceutical composition as described herein, to the subject in need thereof, wherein prior to administration of the oncolytic vaccinia virus or the pharmaceutical composition the subject can be diagnosed with a cancer or a tumor. In certain embodiments, the method can comprise the administration of the oncolytic vaccinia virus according to this disclosure or a pharmaceutical composition as described herein, to the subject in need thereof in combination with the further therapy, wherein prior to administration of the oncolytic vaccinia virus or the pharmaceutical composition or the further therapy the subject may have been diagnosed with a cancer or a tumor. In certain embodiments, the method comprises the administration of the oncolytic vaccinia virus according to this disclosure or a pharmaceutical composition as described herein, to the subject in need thereof in combination with the further therapy, wherein prior to administration of the oncolytic vaccinia virus or the pharmaceutical composition the subject may have been diagnosed with a cancer or a tumor.

One non-limiting embodiment provides a virus comprising an exogenous nucleic acid, wherein said exogenous nucleic acid can encode a protein or a fragment thereof that can modulate STAT3-mediated gene-activation. In certain embodiments, the virus can comprise the exogenous nucleic acid sequence, wherein said virus can be a vaccinia virus. In certain embodiments, the virus can comprise the exogenous nucleic acid, wherein the oncolytic vaccinia virus can be an oncolytic vaccinia virus. In certain embodiments, the protein or the fragment thereof can be a PIAS3 protein or a fragment thereof. In certain embodiments, the virus can comprise the exogenous nucleic acid coding for the PIAS3 protein or a fragment thereof, wherein the exogenous nucleic acid can be at least about 85%, at least about 90%, at least about 95%, at least about 96%, at least about 97%, at least about 98%, at least about 99%, or 100% homologous to a nucleic acid sequence selected from the group consisting of SEQ ID NOs: 8-10 and 40-43, or a fragment thereof. In certain embodiments, the virus can comprise the exogenous nucleic acid coding for the PIAS3 protein or a fragment thereof, wherein PIAS3 protein or the fragment thereof can comprise an amino acid sequence that can be at least about 85%, about 90%, about 95%, about 96%, about 97%, about 98%, about 99%, or 100% homologous to an amino acid fragment from any one of SEQ ID NOs: 1-7 and 24-27, or a fragment thereof.

In certain embodiments, the oncolytic vaccinia virus can comprise an exogenous nucleic acid sequence that can encode a PIAS3 protein or a fragment thereof that can comprise amino acids 400-528 of the amino acid sequence of SEQ ID NO: 1 and conservative substitutions thereof. In certain embodiments, the oncolytic vaccinia virus can comprise an exogenous nucleic acid sequence that can encode a PIAS3 protein or a fragment thereof that can comprise amino acids 400-523 of the amino acid sequence of SEQ ID NO: 6 and conservative substitutions thereof.

In certain embodiments, the protein or a fragment thereof that modulates STAT3 activity, e.g., modulate STAT3-mediated gene-activation, can be a SOCS3 protein or a fragment thereof and conservative substitutions thereof. In certain embodiments, the exogenous nucleic acid can comprise a SOCS3 protein or a fragment thereof comprises a human SOCS3 protein or a fragment thereof and conservative substitutions thereof. In certain embodiments, the SOCS3 protein or the fragment thereof can comprise an amino acid sequence that is at least about 85% homologous to an amino acid sequence selected from the group consisting of SEQ ID NOs: 28 and 30 and conservative substitutions thereof. In certain embodiments, the SOCS3 protein or the fragment thereof can comprise an amino acid sequence that can be at least about 85% homologous to the amino acid sequence of SEQ ID NO: 28 and conservative substitutions thereof. In certain embodiments, the SOCS3 protein or the fragment thereof can comprise an amino acid sequence that can be at least about 85% homologous to the entire length of an amino acid sequence selected from the group consisting of SEQ ID NOs: 28 and 30 and conservative substitutions thereof. In certain embodiments, the SOCS3 protein or the fragment thereof comprises an amino acid sequence that can be at least about 85% homologous to a fraction of the entire length of an amino acid sequence selected from the group consisting of SEQ ID NOs: 28 and 30 and conservative substitutions thereof.

In certain embodiments, the exogenous nucleic acid that can encode a protein or a fragment thereof that modulates STAT3 activity, e.g., modulate STAT3-mediated gene-activation, can be a TCPTP protein or a fragment thereof and conservative substitutions thereof. In certain embodiments, the exogenous nucleic acid can comprise a TCPTP protein or the fragment thereof, wherein the TCPTP protein or the fragment thereof is a human TCPTP protein or a fragment thereof and conservative substitutions thereof. In certain embodiments, the TCPTP protein or the fragment thereof can comprise an amino acid sequence that can be at least about 85% homologous to an amino acid sequence selected from the group consisting of SEQ ID NOs: 32 and 34 and conservative substitutions thereof. In certain embodiments, the TCPTP protein or the fragment thereof can comprise an amino acid sequence that can be at least about 85% homologous to the amino acid sequence of SEQ ID NO: 32 and conservative substitutions thereof. In certain embodiments, the TCPTP protein or the fragment thereof can comprise an amino acid sequence that can be at least about 85% homologous to the entire length of an amino acid sequence selected from the group consisting of SEQ ID NOs: 32 and 34 and conservative substitutions thereof. In certain embodiments, the TCPTP protein or the fragment thereof can comprise an amino acid sequence that can be at least about 85% homologous to a fraction of the entire length of an amino acid sequence selected from the group consisting of SEQ ID NOs: 32 and 34 and conservative substitutions thereof.

In certain embodiments, the protein or a fragment thereof that modulates STAT3 activity, e.g., modulate STAT3-mediated gene-activation, can be a dominant-negative mutant STAT3 protein or a fragment thereof and conservative substitutions thereof. In certain embodiments, the dominant-negative mutant STAT3 protein or the fragment thereof can be a human dominant-negative mutant STAT3 protein or a fragment thereof and conservative substitutions thereof. In certain embodiments, the dominant-negative mutant STAT3 protein or the fragment thereof can comprise an amino acid sequence that can be at least about 85% homologous to an amino acid sequence selected from the group consisting of SEQ ID NOs: 36 and 38 and conservative substitutions thereof. In certain embodiments, the dominant-negative mutant STAT3 protein or the fragment thereof can comprise an amino acid sequence that can be at least about 85% homologous to the entire length of an amino acid sequence selected from the group consisting of SEQ ID NOs: 36 and 38 and conservative substitutions thereof. In certain embodiments, the dominant-negative mutant STAT3 protein or the fragment thereof can comprise an amino acid sequence that can be at least about 85% homologous to a fraction of the entire length of an amino acid sequence selected from the group consisting of SEQ ID NOs: 36 and 38 and conservative substitutions thereof.

In certain embodiments, the exogenous nucleic acid can further encode a cell-penetrating protein, wherein the cell-penetrating protein comprises a TAT protein of HIV-1 or a fragment thereof, YopM, transportan, penetratin, poly-arginine, or any combinations thereof. In certain embodiments, the exogenous nucleic acid can further encode the cell-penetrating protein, wherein the exogenous nucleic acid further comprises a sequence that can be at least about 85%, at least about at least 90%, at least about 95%, at least about 96%, at least about 97%, at least about 98%, at least about 99%, or 100% homologous to SEQ ID NO: 12, 13, 115, 17, 19, 21 and 23, or fragments thereof. In certain embodiments, the nucleic acid can further encode a cell-penetrating protein, wherein the exogenous nucleic acid can further comprise a sequence that can be at least about 85%, at least about 90%, at least about 95%, at least about 96%, at least about 97%, at least about 98%, at least about 99%, or 100% homologous to the entire length of SEQ ID NO: 12, 13, 115, 17, 19, 21 and 23. In certain embodiments, the exogenous nucleic acid can further encode the cell-penetrating protein, wherein the exogenous nucleic acid can further comprises a sequence that can be at least about 85%, at least about 90%, at least about 95%, at least about 96%, at least about 97%, at least about 98%, at least about 99%, or 100% homologous to a fraction of the length of SEQ ID NO: 12, 13, 115, 17, 19, 21 and 23. In certain embodiments, the exogenous nucleic acid can encode the cell-penetrating peptide or the fragment thereof, wherein the cell-penetrating peptide or the fragment thereof can comprise a sequence that is at least about 85%, at least about 90%, at least about 95%, at least about 96%, at least about 97%, at least about 98%, at least about 99%, or 100% identical to SEQ ID NO: 11, 14, 16, 18, 20 and 22 and conservative substitutions thereof, or a fragment thereof and conservative substitutions thereof. In certain embodiments, the protein or the fragment thereof that modulates STAT3 activity can be conjugated to a cell-penetrating peptide having an amino acid that can be at least about 85% homologous to the amino acid sequence of SEQ ID NO: 11.

In certain embodiments, the protein or the fragment thereof that modulates STAT3 activity can be conjugated to a cell-penetrating peptide comprising the amino acid sequence of SEQ ID NO: 11. In certain embodiments, the protein or the fragment thereof can comprise the blocking fragment, wherein the blocking fragment can comprise amino acids 126-176 of SEQ ID NO: 1. In certain embodiments, the protein or the fragment thereof can comprise the PIAS3 protein or the fragment thereof, wherein the PIAS3 protein or the fragment thereof can comprise amino acids 129-316, 133-316, 132-177, 126-176 or 400-528 of SEQ ID NO: 1.

In certain embodiments, the protein or a fragment thereof that can modulate STAT3-mediated gene-activation can be a STAT3 inhibitor.

In certain non-limiting methods of the present disclosure, the subject can be administered a ketogenic diet prior to, concurrently, or following administration of the oncolytic vaccinia virus according to this disclosure, or the pharmaceutical composition as described herein.

In certain embodiments, the oncolytic vaccinia virus comprises an exogenous nucleic acid, wherein the exogenous nucleic acid can comprise a nucleic acid fragment that can comprise a non-contiguous stretch of nucleotides from a nucleotide sequence that can be selected from the group consisting of from a nucleotide sequence selected from the group consisting of SEQ ID NOs: 8-10, 29, 31, 33, 35, 37 and 39-43. In certain embodiments, the oncolytic vaccinia virus comprises an exogenous nucleic acid, wherein the exogenous nucleic acid can comprise the nucleotide sequence of SEQ ID NO: 8. In certain embodiments, the oncolytic vaccinia virus can comprise an exogenous nucleic acid, wherein the exogenous nucleic acid can comprise the nucleotide sequence of SEQ ID NO: 9. In certain embodiments, the oncolytic vaccinia virus comprises an exogenous nucleic acid, wherein the exogenous nucleic acid can comprise the nucleotide sequence of SEQ ID NO: 10. In certain embodiments, the oncolytic vaccinia virus comprises an exogenous nucleic acid, wherein the exogenous nucleic acid can comprise the nucleotide sequence of SEQ ID NO: 29. In certain embodiments, the oncolytic vaccinia virus can comprise an exogenous nucleic acid, wherein the exogenous nucleic acid can comprise the nucleotide sequence of SEQ ID NO: 31. In certain embodiments, the oncolytic vaccinia virus comprises an exogenous nucleic acid, wherein the exogenous nucleic acid can comprise the nucleotide sequence of SEQ ID NO: 33. In certain embodiments, the oncolytic vaccinia virus comprises an exogenous nucleic acid, wherein the exogenous nucleic acid can comprise the nucleotide sequence of SEQ ID NO: 35. In certain embodiments, the oncolytic vaccinia virus comprises an exogenous nucleic acid, wherein the exogenous nucleic acid can comprise the nucleotide sequence of SEQ ID NO: 37. In certain embodiments, the oncolytic vaccinia virus comprises an exogenous nucleic acid, wherein the exogenous nucleic acid can comprise the nucleotide sequence of SEQ ID NO: 39. In certain embodiments, the oncolytic vaccinia virus comprises an exogenous nucleic acid, wherein the exogenous nucleic acid can comprise the nucleotide sequence of SEQ ID NO: 40. In certain embodiments, the oncolytic vaccinia virus comprises an exogenous nucleic acid, wherein the exogenous nucleic acid can comprise the nucleotide sequence of SEQ ID NO: 41. In certain embodiments, the oncolytic vaccinia virus comprises an exogenous nucleic acid, wherein the exogenous nucleic acid can comprise the nucleotide sequence of SEQ ID NO: 42. In certain embodiments, the oncolytic vaccinia virus comprises an exogenous nucleic acid, wherein the exogenous nucleic acid can comprise the nucleotide sequence of SEQ ID NO: 43.

DETAILED DESCRIPTION

Figure 1:
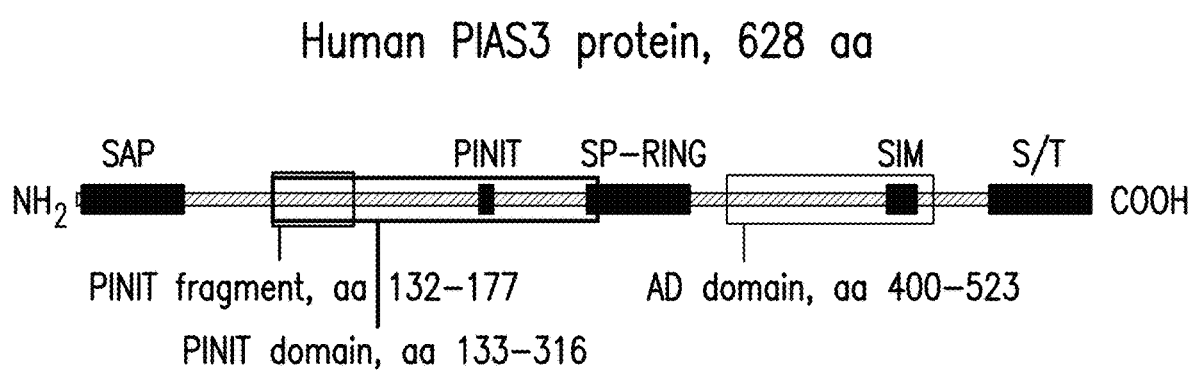
FIG. 1 shows the structural domains of PIAS3.

While preferred embodiments of this disclosure have been shown and described herein, it will be obvious to those skilled in the art that such embodiments are provided by way of example only. Numerous variations, changes, and substitutions will now occur to those skilled in the art without departing from this disclosure. It should be understood that various alternatives to the embodiments of this disclosure described herein may be employed in practicing the disclosure. It is intended that the following claims define the scope of the disclosure and that methods and structures within the scope of these claims and their equivalents be covered thereby.

Certain Definitions

The terminology used herein is for the purpose of describing particular cases only and is not intended to be limiting.

As used herein, the singular forms "a", "an" and "the" can include the plural forms as well, unless the context clearly indicates otherwise. Furthermore, to the extent that the terms "contains," "containing," "including", "includes," "having," "has", "with", or variants thereof are used in either the detailed description and/or the claims, such terms are intended to be inclusive in a manner similar to the term "comprising."

The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value, such as ±10% of the value modified by the term "about".

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker). In certain embodiments, patients, subjects, or individuals can be under the supervision of a health care worker.

The terms "heterologous nucleic acid sequence," or "exogenous nucleic acid sequence," as used herein, in relation to a specific virus can refer to a nucleic acid sequence that originates from a source other than the specified virus.

The term "mutation," as used herein, can refer to a deletion, an insertion of a heterologous nucleic acid, an inversion or a substitution, including an open reading frame ablating mutations as commonly understood in the art.

The term "gene," as used herein, can refer to a segment of nucleic acid that encodes an individual protein or RNA (also referred to as a "coding sequence" or "coding region"), optionally together with associated regulatory regions such as promoters, operators, terminators and the like, which may be located upstream or downstream of the coding sequence.

The terms "mutant virus" and "modified virus," as used interchangeably herein, can refer to a virus comprising one or more mutations in its genome, including but not limited to deletions, insertions of heterologous nucleic acids, inversions, substitutions or combinations thereof.

The term "naturally-occurring," as used herein with reference to a virus, can indicate that the virus can be found in nature, i.e., it can be isolated from a source in nature and has not been intentionally modified.

The terms "inhibiting," "reducing" or "prevention," or any variation of these terms, referred to herein, can include any measurable decrease or complete inhibition to achieve a desired result.

A "promoter," as used herein, can be a control sequence that is a region of a nucleic acid sequence at which initiation and rate of transcription are controlled. In certain embodiments, a promoter may contain genetic elements at which regulatory proteins and molecules may bind such as RNA polymerase and other transcription factors. The terms "operatively positioned," "operatively linked," "under control" and "under transcriptional control" can mean that a promoter is in a correct functional location and/or orientation in relation to a nucleic acid sequence to control transcriptional initiation and/or expression of that sequence. In certain embodiments, a promoter may or may not be used in conjunction with an "enhancer," which refers to a cis-acting regulatory sequence involved in the transcriptional activation of a nucleic acid sequence.

The term "homology," as used herein, may be to calculations of "homology" or "percent homology" between two or more nucleotide or amino acid sequences that can be determined by aligning the sequences for optimal comparison purposes (e.g., gaps can be introduced in the sequence of a first sequence). The nucleotides at corresponding positions may then be compared, and the percent identity between the two sequences may be a function of the number of identical positions shared by the sequences (i.e., % homology=# of identical positions/total # of positions×100). For example, a position in the first sequence may be occupied by the same nucleotide as the corresponding position in the second sequence, then the molecules are identical at that position. The percent homology between the two sequences may be a function of the number of identical positions shared by the sequences, taking into account the number of gaps, and the length of each gap, which need to be introduced for optimal alignment of the two sequences. In certain embodiments, the length of a sequence aligned for comparison purposes may be at least about: 30%, 40%, 50%, 60%, 65%, 70%, 75%, 80%, 85%, 90%, 91%, 92%, 93%, 94%, 95%, 96%, 97%, 98%, or 95%, of the length of the reference sequence. A basic local alignment search tool (BLAST®) search may determine homology between two sequences. The two sequences can be genes, nucleotides sequences, protein sequences, peptide sequences, amino acid sequences, or fragments thereof. The actual comparison of the two sequences can be accomplished by well-known methods, for example, but not by way of limitation, using a mathematical algorithm. A non-limiting example of such a mathematical algorithm is described in Karlin, S. and Altschul, S., Proc. Natl. Acad. Sci. USA, 90-5873-5877 (1993). Such an algorithm may be incorporated into the NBLAST and) (BLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In another non-limiting embodiment, the percent identity between two amino acid sequences can be accomplished using, for example, the GAP program in the GCG software package (Accelrys, Cambridge, UK).

The term "subject" can refer to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" can be meant to include alleviating or abrogating a disorder, disease, or condition; or one or more of the symptoms associated with the disorder, disease, or condition; or alleviating or eradicating the cause(s) of the disorder, disease, or condition itself. In certain embodiments, treatment can be performed either for prophylaxis or during the course of clinical pathology. Desirable effects of treatment can include, but are not limited to, preventing occurrence or recurrence of disease, alleviation of symptoms, diminishing any direct or indirect pathological consequences of the disease, preventing metastasis, decreasing the rate of disease progression, amelioration or palliation of the disease state and remission or improved prognosis.

The terms "therapeutically effective amount" or "effective amount," as used interchangeably herein, can refer to the amount of a compound that, when administered, can be sufficient to prevent development of, or alleviate to some extent, one or more of the symptoms of the disorder, disease, or condition being treated. The term "therapeutically effective amount" can also refer to the amount of a compound that is sufficient to elicit the biological or medical response of a cell, tissue, system, animal, or human that is being sought by a researcher, veterinarian, medical doctor, or clinician.

The terms "pharmaceutically acceptable carrier," "pharmaceutically acceptable excipient," "physiologically acceptable carrier," or "physiologically acceptable excipient" can refer to a pharmaceutically-acceptable material, composition, or vehicle, such as a liquid or solid filler, diluent, excipient, solvent, or encapsulating material. A component can be "pharmaceutically acceptable" in the sense of being compatible with the other ingredients of a pharmaceutical formulation. It can also be suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, PA, 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation,* Gibson Ed., CRC Press LLC: Boca Raton, F L, 2004).

The term "pharmaceutical composition," as used herein, can refer to a mixture of a compound disclosed herein with other chemical components, such as diluents or carriers. The pharmaceutical composition can facilitate administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

An "anti-cancer agent," as used herein, can refer to an agent or therapy that is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Non-limiting examples of anti-cancer agents can include biological agents (biotherapy), chemotherapy agents, and radiotherapy agents.

The term "oncolytic," as used herein, can refer to killing of cancer or tumor cells by an agent, such as an oncolytic vaccinia virus, e.g., through the direct lysis of said cells, by stimulating immune response towards said cells, apoptosis, expression of toxic proteins, autophagy and shut-down of protein synthesis, induction of anti-tumoral immunity, or any combinations thereof. The direct lysis of the cancer or tumor cells infected by the agent, such as an oncolytic vaccinia virus, can be a result of replication of the virus within said cells. In certain examples, the term "oncolytic," refers to killing of cancer or tumor cells without lysis of said cells.

The term "dominant-negative mutation," as used herein, can refer to a mutation in an amino acid sequence of a protein or a nucleotide sequence that encodes the protein that results in a mutated form of the protein that acts antagonistically to the wild-type form of the protein.

Modified Viruses

In certain embodiments, modified viruses, e.g., oncolytic vaccinia viruses, containing an exogenous nucleic acid sequence that encodes a modulator of STAT3 activity, e.g., STAT-3 mediated gene-activation, are provided. STAT3 can indirectly regulate several target genes by mediating expression of other transcription factors or physical association with other transcription factors to enhance or suppress their function in gene regulation. Examples of STAT3-regulated genes include, but are not limited to, p53 (NG_017013.2), Fas (NG_009089.2), Hsp70 (NC_000005.10), Cyclin-D1 (NG_007375.1), IL-10 (NG_012088.1), etc. See, e.g., Carpenter and Lo, Cancers, 2014, 6, 897-925, which is incorporated by reference herein.

In certain embodiments, viruses described herein comprise one or more exogenous nucleic acid sequences, alternatively referred to as transgenes, which can generate mRNAs coding for an agent that can modulate the activity of STAT3 and as a result can also modulate the activation of genes regulated by STAT3. Thus, certain examples provided herein provide oncolytic vaccinia viruses containing exogenous nucleic acid sequences that can encode an agent that can modulate STAT-3 mediated gene-activation. The phrase "modulates STAT3-mediated gene activation," as used herein, can refer to a process wherein STAT3 activity is modulated and as a consequence the activation of one or more genes that are regulated by STAT3 is also modulated.

In certain embodiments, the agent that can modulate STAT3-mediated gene activation is a protein or a fragment thereof. In certain embodiments, the protein or the fragment thereof can inhibit, reduce, or minimize STAT3 activity and STAT3-mediated gene activation. A protein or a fragment thereof that inhibits, reduces and/or minimizes STAT3 activity and STAT3-mediated gene activation can, for example, block the binding of STAT3 to a DNA binding sequence in the promoter regions of STAT3 responsive genes. In additional examples, the protein or a fragment thereof that inhibits, reduces, or minimizes STAT3 activity and STAT3-mediated gene activation can directly bind the STAT3 protein, for example, at the SH2 domain. In certain embodiments, a protein that inhibits, reduces and/or minimizes STAT3 activity blocks, prevents, reduces and/or minimizes the phosphorylation of STAT3 and/or dephosphorylates STAT3. In certain non-limiting embodiments, the proteins that modulate STAT3 activity can include phosphotyrosine phosphatases (PTPs), protein inhibitor of activated STAT (PIAS) and suppressor of cytokine signaling (SOCS) proteins.

In certain embodiments, the protein or the fragment thereof that inhibits, reduces, or minimizes STAT3 activity and STAT3-mediated gene activation can be a PIAS3 protein or a fragment thereof. For example, and not by way of limitation, a modified virus, e.g., an oncolytic vaccinia virus, of this disclosure can express a PIAS3 protein or a fragment thereof. In certain embodiments, the modified virus can express a human PIAS3 protein, e.g., that can comprise an amino acid sequence that is at least about 85%, about 90%, about 95%, about 96%, about 97%, about 98%, about 99% or 100% homologous to the amino acid sequence of SEQ ID NO: 1, or a fragment thereof and conservative substitutions thereof.

In certain embodiments, the modified viruses can express a mouse PIAS3 protein or a fragment thereof, e.g., that can comprise an amino acid sequence that is at least about 85%, about 90%, about 95%, about 96%, about 97%, about 98%, about 99% or 100% homologous to the amino acid sequence of SEQ 1D NO: 6, or a fragment thereof and conservative substitutions thereof.

In certain embodiments, the virus can express a rat PIAS3 protein or a fragment thereof, e.g., that can comprise an amino acid sequence that is at least about 85%, about 90%, about 95%, about 96%, about 97%, about 98%, about 99% or 100% homologous to the amino acid sequence of SEQ ID NO: 7, or a fragment thereof and conservative substitutions thereof.

In certain embodiments, this disclosure provides a modified virus, e.g., an oncolytic vaccinia virus, that can express a PINIT (proline, isoleucine, asparagine, isoleucine, threonine) fragment of a PIAS3 protein. In certain embodiments, the PINIT fragment can comprise amino acids 126-176 of SEQ ID NO: 1 and conservative substitutions thereof. For example, and not by way of limitation, the PINIT fragment can comprise the amino acid sequence set forth in SEQ ID NO: 4 and conservative substitutions thereof. In certain embodiments, the PINIT fragment can comprise amino acids 132-177 of SEQ ID NO: 1 and conservative substitutions thereof. In certain embodiments, the PINIT fragment can comprise the amino acid sequence set forth in SEQ ID NO: 3 and conservative substitutions thereof.

In certain embodiments, this disclosure provides a modified virus, e.g., an oncolytic vaccinia virus, that can express the PINIT domain of a PIAS3 protein. In certain embodiments, the PINIT domain can comprise amino acids 129-316 of SEQ ID NO: 1 or conservative substitutions thereof. For example, and not by way of limitation, the PINIT domain can comprise the amino acid sequence set forth in SEQ ID NO: 5 and conservative substitutions thereof. In certain embodiments, the PINIT domain can comprise amino acids 133-316 of SEQ ID NO: 1 or conservative substitutions thereof. In certain embodiments, the PINIT domain can comprise the amino acid sequence set forth in SEQ ID NO: 2 and conservative substitutions thereof.

In certain embodiments, the present invention provides a virus, e.g., vaccinia virus, expressing the acidic domain of a human PIAS3 protein. In certain embodiments, the acidic domain comprises amino acids 400-528 of SEQ ID NO: 1 and conservative substitutions thereof. For example, and not by way of limitation, the acidic domain comprises the amino acid sequence set forth in SEQ ID NO: 24 and conservative substitutions thereof. In certain embodiments, the acidic domain of a mouse PIAS3 protein comprises amino acids 400-523 of SEQ ID NO: 6 and conservative substitutions thereof. For example, and not by way of limitation, the acidic domain comprises the amino acid sequence set forth in SEQ ID NO: 26 and conservative substitutions thereof.

In certain embodiments, this disclosure provides a modified virus, e.g., an oncolytic vaccinia virus, that can express a PIAS3 protein or a fragment thereof that can comprise an amino acid sequence that is at least about 85%, about 90%, about 95%, about 96%, about 97%, about 98%, about 99% or 100% homologous to an amino acid sequence selected from the group consisting of SEQ ID NOs: 1-7 and 24-27, or a fragment thereof and conservative substitutions thereof. In certain embodiments, the PIAS3 protein or the fragment thereof can comprise an amino acid sequence that is at least about 85%, about 90%, about 95%, about 96%, about 97%, about 98%, about 99%, or 100% homologous to the entire length of an amino acid sequence selected from the group consisting of SEQ ID NOs: 1-7 and 24-27. In certain embodiments, the PIAS3 protein or the fragment thereof can comprise an amino acid sequence that is at least about 85%, about 90%, about 95%, about 96%, about 97%, about 98%, about 99%, or 100% homologous to a fraction of the entire length of an amino acid sequence selected from the group consisting of SEQ ID NOs: 1-7 and 24-27. In additional examples, the PIAS3 protein or the fragment thereof can comprise an amino acid sequence that is at least about 85%, about 90%, about 95%, about 96%, about 97%, about 98%, about 99%, or 100% homologous to the entire length of the amino acid sequence of SEQ ID NO: 1. In yet other examples, the PIAS3 protein or the fragment thereof can comprise an amino acid sequence that is at least about 85%, about 90%, about 95%, about 96%, about 97%, about 98%, about 99%, or 100% homologous to a fraction of the entire length of the amino acid sequence of SEQ ID NO: 1. In certain embodiments, the PIAS3 protein can be further conjugated to a cell penetrating peptide, as disclosed herein, and the exogenous nucleic acid can further encode a cell penetrating peptide.

In certain embodiments, this disclosure provides a modified virus, e.g., an oncolytic vaccinia virus, that can be modified to comprise one or more heterologous nucleic acids, e.g., genes, encoding a protein or a fragment thereof that can inhibit, reduce, or minimize STAT3 activity and STAT3-mediated gene activation, as described above. In certain embodiments, this disclosure provides modified viruses, e.g., oncolytic vaccinia viruses having a nucleic acid encoding a protein that can inhibit, reduce, or minimize STAT3 activity. For example, and not by way of limitation, this disclosure provides a modified virus, e.g., an oncolytic vaccinia virus having one or more nucleic acids that can encode a PIAS3 protein or a fragment thereof (e.g., a PINIT domain or a PINIT fragment of a PIAS3 protein) as disclosed herein. In certain embodiments, the nucleic acid that can encode a PIAS3 protein can comprise a nucleotide sequence selected from the group consisting of SEQ ID NO:

8-10 and or a fragment thereof. In certain embodiments, the nucleic acid that can encode a PIAS3 protein can comprise a nucleotide sequence that is at least about 85%, about 90%, about 95%, about 96%, about 97%, about 98%, about 99%, or 100% homologous to the entire length of a nucleic acid sequence selected from the group consisting of SEQ ID NOs: 8-10 and 40-43. In certain embodiments, the nucleic acid that can encode a PIAS3 protein can be at least about 85%, about 90%, about 95%, about 96%, about 97%, about 98%, about 99%, or 100% homologous to a fraction of a nucleic acid sequence selected from the group consisting of SEQ ID NOs: 8-10 and 40-43. In certain embodiments, the nucleic acid that can encode a PIAS3 protein can comprise the nucleotide sequence of SEQ ID NO: 8. In certain embodiments, the nucleic acid that can encode a PIAS3 protein can comprise the nucleotide sequence of SEQ ID NO: 9. In certain embodiments, the nucleic acid that can encode a PIAS3 protein can comprise the nucleotide sequence of SEQ ID NO: 10. In certain non-limiting embodiments, the nucleic acid that encodes a PIAS3 protein comprises the nucleotide sequence of SEQ ID NO: 40. In certain non-limiting embodiments, the nucleic acid that encodes a PIAS3 protein comprises the nucleotide sequence of SEQ ID NO: 41. In certain non-limiting embodiments, the nucleic acid that encodes a PIAS3 protein comprises the nucleotide sequence of SEQ ID NO: 42. In certain non-limiting embodiments, the nucleic acid that encodes a PIAS3 protein comprises the nucleotide sequence of SEQ ID NO: 43. In certain embodiments, the fragment can have a length of about 3 to about 6 nucleotides, about 6 to about 9 nucleotides, about 9 to about 12 nucleotides, about 12 to about 15 nucleotides, about 15 to about 18 nucleotides, about 18 to about 21 nucleotides, about 21 to about 24 nucleotides, about 24 to about 99 nucleotides, about 99 to about 120 nucleotides, about 120 to about 150 nucleotides, about 150 to about 153 nucleotides, about 156 nucleotides to about 573 nucleotides, about 576 nucleotides to about 600 nucleotides, or more, from a nucleotide sequence selected from the group consisting of SEQ ID NOs: 8-10 and 40-43. In certain embodiments, the fragment can comprise a contiguous stretch of nucleotides from a nucleotide sequence selected from SEQ ID NOs: 8-10 and 40-43. In certain embodiments, the fragment can comprise non-contiguous nucleotides from a nucleotide sequence selected from SEQ ID NOs: 8-10 and 40-43.

In certain embodiments, the protein or the fragment thereof that inhibits, reduces, or minimizes STAT3 activity and STAT3-mediated gene activation can be a SOCS3 protein or a fragment thereof. For example, and not by way of limitation, a modified virus, e.g., an oncolytic vaccinia virus, of this disclosure can express a SOCS3 protein or a fragment thereof. In certain embodiments, the modified virus can express a human SOCS3 protein, e.g., that can comprise an amino acid sequence that is at least about 85%, at least about 90%, at least about 95%, at least about 96%, at least about 97%, at least about 98%, at least about 99% or 100% homologous to the amino acid sequence of SEQ ID NO: 28 or 30, or a fragment thereof and conservative substitutions thereof. In certain embodiments, the modified viruses can comprise an exogenous nucleic acid that can express a SOCS3 protein or a fragment thereof, wherein said nucleic acid can comprise a nucleotide sequence that is at least about 85%, about 90%, about 95%, about 96%, about 97%, about 98%, about 99% or 100% homologous to the amino acid sequence of SEQ 1D NO: 29 or 31, or a fragment thereof. In certain embodiments, the SOCS3 protein or the fragment thereof can comprise an amino acid sequence that is at least about 85%, at least about 90%, at least about 95%, at least about 96%, at least about 97%, at least about 98%, at least about 99%, or 100% homologous to the entire length of an amino acid sequence selected from the group consisting of SEQ ID NOs: 28 and 30. In certain embodiments, the SOCS3 protein or the fragment thereof can comprise an amino acid sequence that is at least about 85%, at least about 90%, at least about 95%, at least about 96%, at least about 97%, at least about 98%, at least about 99%, or 100% homologous to a fraction of the entire length of an amino acid sequence selected from the group consisting of SEQ ID NOs: 28 and 30. In certain embodiments, the SOCS3 protein can be further conjugated to a cell penetrating peptide, as disclosed herein, and the exogenous nucleic acid can further encode a cell penetrating peptide.

In certain embodiments, the protein or the fragment thereof that inhibits, reduces, or minimizes STAT3 activity and STAT3-mediated gene activation can be a TCPTP protein or a fragment thereof. For example, and not by way of limitation, a modified virus, e.g., an oncolytic vaccinia virus, of this disclosure can express a TCPTP protein or a fragment thereof. In certain embodiments, the modified virus can express a human TCPTP protein, e.g., that can comprise an amino acid sequence that is at least about 85%, at least about 90%, at least about 95%, at least about 96%, at least about 97%, at least about 98%, at least about 99% or 100% homologous to the amino acid sequence of SEQ ID NO: 32 or 34, or a fragment thereof, and conservative substitutions thereof. In certain embodiments, the modified viruses can comprise an exogenous nucleic acid that can express a TCPTP protein or a fragment thereof, wherein said nucleic acid can comprise a nucleotide sequence that is at least about 85%, at least about 90%, at least about 95%, at least about 96%, at least about 97%, at least about 98%, at least about 99% or 100% homologous to the amino acid sequence of SEQ 1D NO: 33 or 35, or a fragment thereof. In certain embodiments, the TCPTP protein or the fragment thereof can comprise an amino acid sequence that is at least about 85%, at least about 90%, at least about 95%, at least about 96%, at least about 97%, at least about 98%, at least about 99%, or 100% homologous to the entire length of an amino acid sequence selected from the group consisting of SEQ ID NOs: 32 and 34. In certain embodiments, the TCPTP protein or the fragment thereof can comprise an amino acid sequence that is at least about 85%, at least about 90%, at least about 95%, at least about 96%, at least about 97%, at least about 98%, at least about 99%, or 100% homologous to a fraction of the entire length of an amino acid sequence selected from the group consisting of SEQ ID NOs: 32 and 34. In certain embodiments, the TCPTP protein can be further conjugated to a cell penetrating peptide, as disclosed herein, and the exogenous nucleic acid can further encode a cell penetrating peptide.

In certain embodiments, the protein or the fragment thereof that inhibits, reduces, or minimizes STAT3 activity and STAT3-mediated gene activation can be a STAT3 protein. For example, and not by way of limitation, a modified virus, e.g., an oncolytic vaccinia virus, of this disclosure can express a STAT3 protein or a fragment thereof. In certain embodiments, the modified virus can express a human STAT3 protein, e.g., that can comprise an amino acid sequence that is at least about 85%, at least about 90%, at least about 95%, at least about 96%, at least about 97%, at least about 98%, at least about 99% or 100% homologous to the amino acid sequence of SEQ ID NO: 36 or 38, or a fragment thereof and conservative substitutions thereof. In certain embodiments, the modified viruses can comprise an exogenous nucleic acid that can express a STAT3 protein or a fragment thereof, wherein said nucleic acid can comprise a nucleotide sequence that is at least about 85%, at least about 90%, at least about 95%, at least about 96%, at least about 97%, at least about 98%, at least about 99% or 100% homologous to the amino acid sequence of SEQ ID NO: 37 or 39, or a fragment thereof. In certain embodiments, the TCPTP protein or the fragment thereof can comprise an amino acid sequence that is at least about 85%, at least about 90%, at least about 95%, at least about 96%, at least about 97%, at least about 98%, at least about 99%, or 100% homologous to the entire length of an amino acid sequence selected from the group consisting of SEQ ID NOs: 36 and 38. In certain embodiments, the TCPTP protein or the fragment thereof can comprise an amino acid sequence that is at least about 85%, at least about 90%, at least about 95%, at least about 96%, at least about 97%, at least about 98%, at least about 99%, or 100% homologous to a fraction of the entire length of an amino acid sequence selected from the group consisting of SEQ ID NOs: 36 and 38. In certain embodiments, the STAT3 protein can be further conjugated to a cell penetrating peptide, as disclosed herein, and the exogenous nucleic acid can further encode a cell penetrating peptide.

In certain embodiments, the nucleic acid can be operably linked to a promoter element, such as a promoter element endogenous to the virus or, alternatively, an introduced exogenous promoter. In certain embodiments, the promoter is a high-expression viral promoter including, but not limited to, the synthetic vaccinia virus promoter "P11 late" derived from the vSC8 vaccinia strain or the "synthetic early/late promoter" derived from the vSC56 vaccinia strain. In certain embodiments, the promoter can be a low-expression viral promoter including, but not limited to, the "P7.5 early/late" promoter derived from the vGK vaccinia strain.

In certain embodiments, the exogenous nucleic acid that can encode a protein or fragment thereof that can modulate STAT3 activity and STAT3-mediated gene activation can independently be inserted at any location of the viral genome, for example in a non-essential locus. Insertion into the oncolytic virus can be performed by routine molecular biology, e.g., as described in Sambrook et al. (2001, Molecular Cloning-A Laboratory Manual, Cold Spring Harbor Laboratory). Insertion into an adenoviral vector or a poxviral vector can be performed through homologous recombination as described respectively in Chartier et al. (1996, J. Virol. 70: 4805-10) and Paul et al. (2002, Cancer gene Ther. 9: 470-7). For example, TK, RR and F2L genes as well as intergenic regions are exemplary loci appropriate for insertion in oncolytic vaccinia virus and E3 and E4 regions for insertion in an oncolytic virus. In certain embodiments, the nucleic acid is inserted at the J2R locus which encodes the thymidine kinase (TK) enzyme resulting in the disruption of the TK locus.

Some non-limiting embodiments of this disclosure provides a modified vaccinia virus that can comprise a nucleic acid that can encode a PIAS3 protein or a fragment thereof, a SOCS3 protein or a fragment thereof, a TCPTP protein or a fragment thereof, or a STAT3 protein comprising one or more dominant-negative mutations, where the nucleic acid can be inserted in the TK gene, resulting in thymidine kinase inactivation. Alternatively, the nucleic acid can be inserted within any non-essential gene within the viral genome or within any intragenic region within the virus genome.

In certain embodiments, the exogenous nucleic acid encoding a PIAS3 protein or a fragment thereof can further encode a cell-penetrating peptide. For example, and not by way of limitation, the cell-penetrating peptide can be derived from the HIV-1 tat gene. In certain embodiments, the cell-penetrating peptide can include TAT47-57 of NCBI/UniProtKB Accession No. NP 057853.1, which has the amino acid sequence YGRKKRRQRRR (SEQ ID NO: 11), e.g., derived from nucleotide residues 5515-5547 of the HIV-1 genome (set forth in NCB1/UniProtKB Accession No. NC_001802.1), which has the nucleotide sequence TATGGCAGGAAGAAGCGGAGACAGCGACGAAGA (SEQ ID NO: 12). In certain embodiments, the nucleic acid that encodes a TAT protein can comprise a nucleotide sequence that can be at least about 85%, about 90%, about 95%, about 96%, about 97%, about 98%, about 99%, or 100% homologous to the entire length of SEQ ID NO: 12. In certain embodiments, the nucleic acid that can encode a TAT protein is at least about 85%, about 90%, about 95%, about 96%, about 97%, about 98%, about 99%, or 100% homologous to a fraction of the entire length of SEQ ID NO: 12. In certain embodiments, the amino sequence of SEQ ID NO: 11 is encoded by the nucleotide sequence TATGGACGAAAAAAACGACGACAACGACGACGA (SEQ ID NO: 13). In certain embodiments, the cell-penetrating peptide can include can be derived from the HIV-1 tat gene and have the nucleotide sequence CGACAACGACGAAAGAAGCGAGGT (SEQ ID NO: 14), which encodes a peptide having the amino acid sequence RQRRKKRG (SEQ ID NO: 15).

In certain embodiments, the cell-penetrating peptide can be an N-terminal domain (NTD) of the *Yersinia pestis* virulence effector YopM having the amino acid sequence KSKTEYYNAWSEWERNAPPGNGEQREMAVSRLRD-CLDRQA (SEQ ID NO: 16). In certain embodiments, the YopM NTD cell-penetrating peptide has the nucleotide sequence

```
                                    (SEQ ID NO: 17)
AAGAGTAAGACGGAGTATTACAATGCTTGGTCAGAGTGGGAGCGAAACG

CCCCTCCAGGCAATGGGGAGCAGCGAGAGATGGCGGTGAGTCGGTTGAG

GGACTGTCTCGACAGGCAGGCA.
```

In certain embodiments, the cell-penetrating peptide can be transportan having the amino acid sequence GWTLN-SAGYLLGKINLKALAALAKKIL (SEQ ID NO: 18). In certain embodiments, the transportan cell-penetrating peptide is encoded by the nucleotide sequence

```
                                    (SEQ ID NO: 19)
GGCTGGACACTTAACAGCGCAGGATATTTGCTTGGCAAAATCAATTTGA
AGGCCTTGGCTGCGCTTGCAAAAAAAATTCTC.
```

In certain embodiments, the cell-penetrating peptide can be penetratin having the amino acid sequence RQIKIWFQNRRMKWKK (SEQ ID NO: 20). In certain embodiments, the penetratin cell-penetrating peptide is encoded by the nucleotide sequence

```
                                    (SEQ ID NO: 21)
CGGCAGATAAAAATCTGGTTCCAGAATCGGCGCATGAAATGGAAGAAA.
```

In certain embodiments, the cell-penetrating peptide can be poly-arginine having the amino acid sequence RRRRRRRRREIHHHHH (SEQ ID NO: 22), e.g., see SEQ ID NOs: 25 and 27. In certain embodiments, the polyarginine cell-penetrating peptide is encoded by the nucleotide sequence (SEQ ID NO: 23)
AGGCGGCGAAGACGCCGCAGGAGACGGCACCACCATCACCATCAC.

In certain embodiments, the cell-penetrating peptide can be conjugated to the PIAS3 protein or a fragment thereof placed either directly at or in close proximity to the N- or C-terminal of a PIAS3 gene construct. In certain embodiments, the cell-penetrating peptide can be conjugated to the SOCS3 protein or a fragment thereof placed either directly at or in close proximity to the N- or C-terminal of a SOCS3 gene construct. In certain embodiments, the cell-penetrating peptide can be conjugated to the TCPTP protein or a fragment thereof placed either directly at or in close proximity to the N- or C-terminal of a TCPTP gene construct. In certain embodiments, the cell-penetrating peptide can be conjugated to the TCPTP protein or a fragment thereof placed either directly at or in close proximity to the N- or C-terminal of a dominant-negative STAT3 nucleic acid construct.

In certain embodiments, the above-described modifications may be produced in any virus that is known in the art. For instance, a vaccinia virus that is known in the art can be modified as described above to be used in this disclosure. Non-limiting examples include the Western Reserve (WR) strain, Copenhagen strain, Wyeth (NYCBOH) strain, Tian Tian strain or USSR strain. In certain embodiments, the above-described modifications may be produced in a virus such as, but not limited to, other poxviruses, HSV, Adenovirus, Reovirus, Newcastle Disease Virus, Measles virus, Maraba virus, Vesicular Stomatitis Virus, AAV and retroviruses. In certain embodiments, the modified vaccinia viruses disclosed herein are of the WR strain. The base vaccinia virus strain modified as set forth herein can itself comprise one or more mutations relative to its parent strain, for example, but not limited to, one or more of the following: deletion in TK; deletion in VGF; SPI-1 deletion; and SPI-2 deletion. In alternative embodiments, the oncolytic virus of the present disclosure can be a vaccinia virus comprising defective TK and Ribonucleotide reductase (RR) activities, where the RR defect results from inactivating mutations in the I4L and/or F4L gene(s) carried by the viral genome. In another non-limiting embodiment, the oncolytic virus of the present disclosure can be a vaccinia virus defective for dUTPase resulting from inactivating mutations in the F2L gene of the viral genome, alone or in combination with disruption of at least one of TK and RR activities or both. In certain embodiments, the vaccinia virus strain can also include a mutation and/or deletion in B8R (IFN gamma binding protein; e.g., see Symons et al., 1995, Cell. 81(4): 551-60); B18R (type I IFN binding protein; e.g., see Colamonici et al., 1995, J. Biol. Chem. 270(27):15974-8); B15R (IL-1β binding protein; e.g., see Alcami et al., 1992, Cell. 71(1):153-67); IL-18BP (e.g., a C12L deletion); B5R (e.g., B5R deletion); and/or C16 (e.g., C16L deletion; see Fahy et al., 2008, J. Gen. Virol. 89:2377-2387). See, also, WO 2015/027163, which is hereby incorporated by reference in its entirety.

Vaccinia viruses usually produce four virion forms, including the single-enveloped intracellular mature virion (IMV), triple-enveloped intracellular enveloped virion (IEV), and the double enveloped cell-associated enveloped virion (CEV) and extracellular enveloped virion (EEV). The EEV form can be associated with long-range virus dissemination. In certain embodiments of this disclosure, a population of oncolytic viruses as describe herein can predominantly comprise the EEV form. In certain embodiments, the disclosed modified vaccinia viruses replicate within M2 macrophages in tumor cells. For example, and not by way of limitation, the vaccinia virus replicates within the M2 macrophages in tumor cells to produce a population of viruses that predominantly contains extracellular enveloped viruses (EEVs). In certain embodiments, the vaccinia virus partially avoids immunosuppression by replicating within the M2 macrophages.

PIAS3 (Protein Inhibitor of Activated STAT3; Denoted PIAS3 Herein)

In certain embodiments, a PIAS3 protein may be a human PIAS3 protein having an amino acid sequence as set forth in NCBI/UniProtKB Accession No. NP 006090.2 or an amino acid sequence at least about 95 percent or at least about 98 percent homologous thereto. In certain embodiments, a PIAS3 protein can comprise an amino acid sequence that has the sequence of SEQ ID NO: 1, set forth below: MAELGELKHMVMSFRVSELQVLLGFAGRNKSGRKHELLAKALHLLKSSCAPSVQMKI KELYRRRFPRKTLGPSDLSLLSLPPGTSPVGSPGPLAPIPPTLLAPG TLLGPKREVDMHPP LPQPVHPDVTMKPLPFYEVYGELIRPTTLASTSSQRFEEAHFTFALTPQQVQQILTSREVL PGAKCDYTIQVQLRFCLCETSCPQEDYFPPNLFVKVNGKLCPLPGYLPPTKNGAEPKRP SRPINITPLARLSATVPNTIVVNWSSEFGRNYSLSVYLVRQLTAGTLLQKLRAKGIRNPD HSRALIKEKLTADPDSEVATTSLRVSLMCPLGKMRLTVPCRALTCAHLQSFDAALYLQ MNEKKPTWTCPVCDKKAPYESLIIDGLFMEILSSCSDCDEIQFMEDGSWCPMKPKKEAS EVCPPPGYGLDGLQYSPVQGGDPSENKKKVEVIDLTIESSSDEEDLPPTKKHCSVTSAAI PALPGSKGVLTSGHQPSSVLRSPAMGTLGGDFLSSLPLHEYPPAFPLGADIQGLDLFSFL QTESQHYGPSVITSLDEQDALGHFFQYRGTPSHFLGPLAPTLGSSHCSATPAPPPGRVSSI VAPGGALREGHGGPLPSGPSLTGCRSDIISLD (SEQ ID NO: 1) or an amino acid sequence at least about 95 percent or at least about 98 percent homologous thereto.

In certain embodiments, a PIAS3 protein of this disclosure can have an amino acid sequence that is a consecutive a fragment of SEQ ID NO: 1, which is at least 20, or at least 30, or at least 40, or at least 50, or at least 60, or at least 70, or at least 80, or at least 90 or at least 100 or at least 200 amino acids or more in length, or an amino acid sequence at least about 95 percent or at least about 98 percent homologous thereto.

In certain embodiments, a PIAS3 protein can comprise amino acids 133-316 of SEQ ID NO: 1 or an amino acid sequence at least about 95 percent or at least about 98 percent homologous thereto. For example, and not by way of limitation, the PIAS3 protein can comprise the amino acid sequence of SEQ ID NO: 2, as set forth below: PFYEVYGELIRPTTLASTSSQRFEEAHFTFALTPQQVQQILTSREVLPGAKCDYTIQVQLR FCLCETSCPQEDYFPPNLFVKVNGKLCPLPGYLPPTKNGAEPKRPSRPINITPLARLSATV PNTIVVNWSSEFGRNYSLSVYLVRQLTAGTLLQKLRAKGIRNPDHSRALIKEKLTADPDS EV (SEQ ID NO: 2) or an amino acid sequence at least about 95 percent or at least about 98 percent homologous thereto.

In certain embodiments, a PIAS3 protein can comprise amino acids 132-177 of SEQ ID NO: 1 or an amino acid sequence at least about 95 percent or at least about 98 percent homologous thereto. For example, and not by way of limitation, the PIAS3 protein can comprise the amino acid sequence of SEQ ID NO: 3, as set forth below: LPFYEVYGELIRPTTLASTSSQRFEEAHFTFALTPQQVQQILTSRE (SEQ ID NO: 3) or an amino acid sequence at least about 95 percent or at least about 98 percent homologous thereto.

In certain embodiments, a PIAS3 protein can comprise amino acids 126-176 of SEQ ID NO: 1 or an amino acid sequence at least about 95 percent or at least about 98 percent homologous thereto. For example, and not by way of limitation, the PIAS3 protein can comprise the amino acid sequence of SEQ ID NO: 4, as set forth below: DVTMKPLPFYEVYGELIRPTTLASTSSQRFEEAHFTFALTPQQVQQILTSR (SEQ ID NO: 4) or an amino acid sequence at least about 95 percent or at least about 98 percent homologous thereto.

In certain embodiments, a PIAS3 protein can comprise amino acids 129-316 of SEQ ID NO: 1 or an amino acid sequence at least about 95 percent or at least about 98 percent homologous thereto. For example, and not by way of limitation, the PIAS3 protein can comprise the amino acid sequence of SEQ ID NO: 5, as set forth below: MKPLPFYEVYGELIRPTTLASTSSQRFEEAHFTFALTPQQVQQILTSREVLPGAKCDYTIQ VQLRFCLCETSCPQEDYFPPNLFVKVNGKLCPLPGYLPPTKNGAEPKRPSRPINITPLARLSATVPNTIVVNWSSEFGRNYSLSVYLVRQLTAGTLLQKLRAKGIRNPDHSRALIKEKLTA DPDSEV (SEQ ID NO: 5) or an amino acid sequence at least about 95 percent or at least about 98 percent homologous thereto.

In certain embodiments, a PIAS3 protein comprises amino acids 400-528 of SEQ ID NO: 1 or an amino acid sequence at least about 95 percent or at least about 98 percent homologous thereto. For example, and not by way of limitation, the PIAS3 protein comprises the amino acid sequence of SEQ ID NO: 24, as set forth below: MEDGSWCPMKPKKEASEVCPPPGYGLDGLQYSPVQGGDPSENKKKVEVIDLTIESSSDEEDLPPTKKHCSVTSAAIPALPGSKGVLTSGHQPSSVLRSPAMGTLGGDFLSSLPLHEYPP AFPLG (SEQ ID NO: 24) or an amino acid sequence at least about 95 percent or at least about 98 percent homologous thereto. In certain embodiment, the C-terminus of a PIAS3 protein can be modified to include a poly-arginine cell-penetrating peptide comprising the amino acid sequence RRRRRRRRRHEIHHHH (SEQ ID NO: 22). For example, and not by way of limitation, a PIAS3 protein conjugated to a poly-arginine cell-penetrating peptide comprises the amino acid sequence of SEQ ID NO: 25, as set forth below: MEDGSWCPMKPKKEASEVCPPPGYGLDGLQYSPVQGGDPSENKKKVEVIDLTIESSSDEEDLPPTKKHCSVTSAAIPALPGSKGVLTSGHQPSSVLRSPAMGTLGGDFLSSLPLHEYPP AFPLGRRRRRRRRRHHHHHH (SEQ ID NO: 25) or an amino acid sequence at least about 95 percent or at least about 98 percent homologous thereto.

In certain embodiments, a PIAS3 protein may be a mouse PIAS3 protein having an amino acid sequence as set forth in NCBI/UniProtKB Accession No. NP 001159421.1 or an amino acid sequence at least about 95 percent or at least about 98 percent homologous thereto. For example, and not by way of limitation, the mouse PIAS3 protein comprises the amino acid sequence of SEQ ID NO: 6, as set forth below: MAELGELKHMVMSFRVSELQVLLGFAGRNKSGRKHELLAKALHLLKSSCAPSVQMKIK ELYRRRFPRKTLGPSDLSLLSLPPGTSPVGSPGPLAPIPPTLLTPGTLLGPKREVDMEIPPLP QPVHPDVTMKPLPFYEVYGELIRPTTLASTSSQRFEEAHFTFALTPQQLQQILTSREVLPG AKCDYTIQVQLRFCLCETSCPQEDYFPPNLFVKVNGKLCPLPGYLPPTKNGAEPKRPSRP INITPLARLSATVPNTIVVNWSSEFGRNYSLSVYLVRQLTAGTLLQKLRAKGIRNPDHSR ALIKEKLTADPDSEVATTSLRVSLMCPLGKMRLTVPCRALTCAHLQSFDAALYLQMNE KKPTWTCPVCDKKAPYESLIIDGLFMEILNSCSDCDEIQFMEDGSWCPMKPKKEASEVC PPPGYGLDGLQYSAVQEGIQPESKKRVEVIDLTIESSSDEEDLPPTKKHCPVTSAAIPALP GSKGALTSGHQPSSVLRSPAMGTLGSDFLSSLPLHEYPPAFPLGADIQGLDLFSFLQTESQ HYGPSVITSLDEQDTLGHFFQYRGTPSHFLGPLAPTLGSSHRSSTPAPPPGRVSSIVAPGSS LREGHGGPLPSGPSLTGCRSDVISLD (SEQ ID NO: 6) or an amino acid sequence at least about 95 percent or at least about 98 percent homologous thereto.

In non-limiting embodiments, a PIAS3 protein of the present invention can have an amino acid sequence that is a consecutive portion of SEQ ID NO: 6, which is at least 20, or at least 30, or at least 40, or at least 50, or at least 60, or at least 70, or at least 80, or at least 90 or at least 100 or at least 200 amino acids or more in length, or an amino acid sequence at least about percent or at least about 98 percent homologous thereto.

In certain embodiments, a mouse PIAS3 protein comprises amino acids 400-523 of SEQ ID NO: 6 or an amino acid sequence at least about 95 percent or at least about 98 percent homologous thereto. For example, and not by way of limitation, the PIAS3 protein comprises the amino acid sequence of SEQ ID NO: 26, as set forth below: MEDGSWCPMKPKKEASEVCPPPGYGLDGLQYSAVQEGIQPESKKRVEVIDLTIESSSDEE DLPPTKKHCPVTSAAIPALPGSKGALTSGHQPSSVLRSPAMGTLGSDFLSSLPLHEYPPAF PLG (SEQ ID NO: 26) or an amino acid sequence at least about 95 percent or at least about 98 percent homologous thereto. In certain embodiment, the C-terminus of the PIAS3 protein having the amino acid sequence of SEQ ID NO: 26 can be modified to include poly-arginine. For example, and not by way of limitation, the PIAS3 protein comprises the amino acid sequence of SEQ ID NO: 27, as set forth below: MEDGSWCPMKPKKEASEVCPPPGYGLDGLQYSAVQEGIQPESKKRVEVIDLTIESSSDEE DLPPTKKHCPVTSAAIPALPGSKGALTSGHQPSSVLRSPAMGTLGSDFLSSLPLHEYPPAF PLGRRRRRRRRRHEIHEIHH (SEQ ID NO: 27) or an amino acid sequence at least about 95 percent or at least about 98 percent homologous thereto.

In certain embodiments, a PIAS3 protein may be a rat PIAS3 protein having an amino acid sequence as set forth in NCBI/UniProtKB Accession No. NP 113972.2 or an amino acid sequence at least about 95 percent or at least about 98 percent homologous thereto. For example, and not by way of limitation, the rat PIAS3 protein comprises the amino acid sequence of SEQ ID NO: 7, as set forth below: MAELGELKHMVMSFRVSELQVLLGFAGRNKSGRKHELLAKALHLLKSSCAPSV QMKIKELYRRRFPRKTLGPSDLSLLSLPPGTSPVGSPSPLASIPPTLLTPGTLLGPKREVDM HPPLPQPVHPDVTMKPLPFYEVYGELIRPTTLASTSSQRFEEAHFTFALTPQQLQQILTSR EVLPGAKCDYTIQVQLRFCL- CETSCPQEDYFPPNLFVKVNGKLCPLPGYLPPTKN-GAEPK RPSRPINITPLARLSATVPNTIVVNWSSEFGR-NYSLSVYLVRQLTAGTLLQKLRAKGIRNP DHSRALIKEKLTADPDSEVATT-SLRVSLMCPLGKMRLTVPCRALTCAHL-QSFDAALYLQ MNEKKPTWTCPVCDKKAPYESLI-IDGLFMEILNSCSDCDEIQFMEDGSWCPMKPKKEAS EVCPPPGYGLDGLQYSPVQEGNQSENKKRVEVI-DLTIESSSDEEDLPPTKKHCPVTSAAIP ALPGSKGALT-SGHQPSSVLRSPAMGTLGSDFLSSLPLHEYPPAFPL-GADIQGLDLFSFLQT ESQHYSPSVITSLDEQDTLGHFFQFRGTPPHFLG-PLAPTLGSSHRSATPAPAPGRVSSIVAP GSSL-REGHGGPLPSGPSLTGCRSDVISLD (SEQ ID NO: 7) or an amino acid sequence at least about 95 percent or at least about 98 percent homologous thereto.

In non-limiting embodiments, a PIAS3 protein of the present invention can have an amino acid sequence that is a consecutive portion of SEQ ID NO: 7, which is at least 20, or at least 30, or at least 40, or at least 50, or at least 60, or at least 70, or at least 80, or at least 90 or at least 100 or at least 200 amino acids or more in length, or an amino acid sequence at least about 95 percent or at least about 98 percent homologous thereto.

In certain embodiments, a PIAS3 protein of this disclosure can have an amino acid sequence comprising the sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 24, SEQ ID NO: 25, SEQ ID NO: 26 or SEQ ID NO: 27. In certain embodiments, a P1AS3 protein can have an amino acid sequence that is at least about 95 percent homologous to the sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 24, SEQ ID NO: 25, SEQ ID NO: 26 or SEQ ID NO: 27. In certain embodiments, a P1AS3 protein can have an amino acid sequence that is at least about 98 percent homologous to the sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 24, SEQ ID NO: 25, SEQ ID NO: 26 or SEQ ID NO: 27.

In certain embodiments, a nucleic acid encoding a human PIAS3 protein can comprise a nucleic acid sequence as set forth in GenBank Accession No. CR457090.1 or a nucleic acid sequence at least about 95 percent or at least about 98 percent homologous thereto. For example, and not by way of limitation, the nucleic acid comprises the nucleotide sequence of SEQ ID NO: 8, as set forth below: ATGGCG-GAGCTGGGCGAATTAAAGCACATGGTGAT-GAGTTTCCGGGTGTCTGAGCT CCAGGTGCTTCTTGGCTTTGCTGGCCG-GAACAAGAGTGGACGGAAGCACGAGCTCCT GGC-CAAGGCTCTGCACCTCCT-GAAGTCCAGCTGTGCCCCTAGTGTCCAGATGAAGAT CAAAGAGCTTTACCGACGACGCTTTCCCCGGAA-GACCCTGGGGCCCTCTGATCTCTC CCTTCTCTCTTTGCCCCTGGCACCTCTCCTGTAG-GCTCCCCTGGTCCTCTAGCTCCC ATTCCC-CAACGCTGTTGGCCCTGGCACCCTGCTGGGCCC-CAAGCGTGAGGTGGAC ATGCACCCCCTCTGCCCCAGCCTGTGCACCCT-GATGTCACCATGAAACCATTGCCC TTCTAT-GAAGTCTATGGGGAGCTCATCCGGCCCAC-CACCCTTGCATCCACTTCTAGC CAGCGGTTTGAGGAAGCGCACTTTACCTTTGCCCT-CACACCCCAGCAAGTGCAGCAG ATTCTTA-CATCCAGAGAGGTTCTGCCAGGAGCCAAATGTGAT-TATACCATACAGGTG CAGCTAAGGTTCTGTCTCTGTGA-GACCAGCTGCCCCCAGGAAGATTATTTTCCCCCC AACCTCTTTGTCAAGGTCAATGG-GAAACTGTGCCCCCTGCCGGGTTACCTTCCCCCA ACCAAGAATGGGGCCGAGCC-CAAGAGGCCCAGCCGCCCCATCAACAT-CACACCCCT GGCTCGACTCTCAGCCACTGTTCC-CAACACCATTGTGGTCAATTGGTCATCTGAGTTC GGACGGAATTACTCCTTGTCTGTGTACCTGGT-GAGGCAGTTGACTGCAGGAACCCTT CTA-CAAAAACTCAGAGCAAAGGGTATCCGGAACCCA-GACCACTCGCGGGCACTGAT CAAGGAGAAATTGACTGCTGACCCTGACAGT-GAGGTGGCCACTACAAGTCTCCGGG TGTCACT-CATGTGCCCGCTAGGGAA-GATGCGCCTGACTGTCCCTTGTCGTGCCCTCA CCTGCGCCCACCTGCAGAGCTTCGATGCTGCCCTT-TATCTACAGATGAATGAGAAGA AGCCTACATGGA-CATGTCCTGTGTGTGACAAGAAGGCTCCCTAT-GAATCTCTTATCA TTGATGGTTTATTTATGGAGATTCT-TAGTTCCTGTTCAGATTGTGATGAGATCCAATT CATGGAAGATGGATCCTGGTGCCCAATGAAACC-CAAGAAGGAGGCATCTGAGGTTT GCC CCCCGCCAGGGTATGGGCTGGATGGCCTCCAGTA-CAGCCCAGTCCAGGGGGGA GATC-CATCAGAGAATAAGAAGAAGGTCGAAGTTAT-TGACTTGACAATAGAAAGCTC ATCAGATGAGGAGGATCTGCCCCCTAC-CAAGAAGCACTGTTCTGTCACCTCAGCTGC CATCCCGGCCCTACCTG-GAAGCAAAGGAGTCCTGACATCTGGCCACCAGC-CATCCTC GGTGCTAAGGAGCCCTGC-TATGGGCACGTTGGGTGGGGATTTCCTGTCCAGTC-TCCC ACTACATGAGTACCCACCTGCCTTCC-CACTGGGAGCCGACATCCAAGGTTTAGATTT ATTTTCATTTCTTCAGACAGAGAGTCAGCAC-TATGGCCCCTCTGTCATCACCTCACTA GAT-GAACAGGATGCCCTTGGC-CACTTCTTCCAGTACCGAGGGACCCCTTCTCACTTT CTGGGCCCACTGGCCCCCACGCTGGGGAGCTCC-CACTGCAGCGCCACTCCGGCGCCC CCTCCTGGCCGTGTCAGCAGCAT-TGTGGCCCCTGGGGGGGCCTTGAGGGAGGGGCA TGGAGGACCCCTGCCCTCAGGTCCCTCTTTGACTG-GCTGTCGGTCAGACATCATTTC CCTGGACTGA (SEQ ID NO: 8) or a nucleic acid sequence at least about 95 percent or at least about 98 percent homologous thereto.

In certain embodiments, a nucleic acid encoding a PIAS3 protein may comprise a nucleic acid sequence of SEQ ID NO: 9, as set forth below: CCCTTCTATGAAGTC-TATGGGGAGCTCATCCGGCCCACCACCCTTGCATC-CACTTCT AGCCAGCGGTTTGAGGAAGCGCACTT-TACCTTTGCCCTCACACCCCAGCAAGTGCAG CAGATTCTTACATCCAGAGAGGTTCTGCCAGGAGC-CAAATGTGATTATACCATACAG GTGCAGCTAAGGTTCTGTCTCTGTGA-GACCAGCTGCCCCCAGGAAGATTATTTTCCC CCCAACCTCTTTGTCAAGGTCAATGG-GAAACTGTGCCCCCTGCCGGGTTACCTTCCC CCAACCAAGAATGGGGCCGAGCC-CAAGAGGCCCAGCCGCCCCATCAACATCACACC CCTGGCTCGACTCTCAGCCACTGTTCCCAACAC-CATTGTGGTCAATTGGTCATCTGA GTTCGGACG-GAATTACTCCTTGTCTGTGTACCTGGT-GAGGCAGTTGACTGCAGGAAC CCTTCTACAAAAACTCAGAGCAAAGGGTATCCG- GAACCCAGACCACTCGCGGGCAC TGAT-CAAGGAGAAATTGACTGCTGACCCTGACAGT-GAGGTG (SEQ ID NO: 9) or a nucleic acid sequence at least about 95 percent or at least about 98 percent homologous thereto.

In certain embodiments, a nucleic acid encoding a PIAS3 protein may comprise a nucleic acid sequence of SEQ ID NO: 10, as set forth below: TTGCCCTTCTATGAAGTC-TATGGGGAGCTCATCCGGCCACCACCCTTGCATC-CACTT CTAGCCAGCGGTTTGAGGAAGCGCACTT-TACCTTTGCCCTCACACCCCAGCAAGTGC AGCAGATTCTTACATCCAGAGAG (SEQ ID NO: 10) or a nucleic acid sequence at least about 95 percent or at least about 98 percent homologous thereto.

In certain embodiments, a nucleic acid encoding a fragment of a human PIAS3 protein that comprises amino acids 400-528 of SEQ ID NO: 1 may comprise the nucleotide sequence of SEQ ID NO: 40, as set forth below: ATGGAA-GATGGATCCTGGTGCCCAATGAAACC-CAAGAAGGAGGCATCTGAGGTTTG CCCCCCGCCAGGGTATGGGCTG-GATGGCCTCCAGTACAGCCCAGTCCAGGGGGGAG ATCCATCAGAGAATAAGAAGAAGGTCGAAGTTAT-TGACTTGACAATAGAAAGCTCA TCAGATGAGGAG-GATCTGCCCCCTACCAAGAAGCACTGTTCTGT-CACCTCAGCTGCC ATCCCGGCCCTACCTGGAAGCAAAGGAGTCCTGA-CATCTGGCCACCAGCCATCCTCG GTGCTAAGGAGCCCTGC-TATGGGCACGTTGGGTGGGGAT-TTCCTGTCCAGTCTCCCA CTACATGAGTACC-CACCTGCCTTCCCACTGGGA (SEQ ID NO: 40) or a nucleotide sequence at least about 95 percent or at least about 98 percent homologous thereto.

In certain embodiments, a nucleic acid encoding a fragment of a human PIAS3 protein that comprises amino acids 400-528 of SEQ ID NO: 1 and a poly-arginine cell penetrating peptide may comprise the nucleotide sequence of SEQ ID NO: 41, as set forth below: ATGGAAGATG-GATCCTGGTGCCCAATGAAACCCAAGAAGGAGG-CATCTGAGGTTTG CCCCCCGCCAGGGTATGGGCTG-GATGGCCTCCAGTACAGCCCAGTCCAGGGGGGAG ATCCATCAGAGAATAAGAAGAAGGTCGAAGTTAT-TGACTTGACAATAGAAAGCTCA TCAGATGAGGAG-GATCTGCCCCCTACCAAGAAGCACTGTTCTGT-CACCTCAGCTGCC ATCCCGGCCCTACCTGGAAGCAAAGGAGTCCTGA-CATCTGGCCACCAGCCATCCTCG GTGCTAAGGAGCCCTGC-TATGGGCACGTTGGGTGGGGAT-TTCCTGTCCAGTCTCCCA CTACATGAGTACC-CACCTGCCTTCCCACTGGGAAGGCGGCGAAGACG-CCGCAGGAG ACGGCACCACCATCACCATCACTAA (SEQ ID NO: 41) or a nucleotide sequence at least about 95 percent or at least about 98 percent homologous thereto.

In certain embodiments, a nucleic acid encoding a fragment of a mouse PIAS3 protein that comprises amino acids 400-523 of SEQ ID NO: 1 may comprise the nucleotide sequence of SEQ ID NO: 42, as set forth below: ATGGAA-GATGGATCCTGGTGTCCGATGAAACC-CAAGAAGGAGGCATCAGAGGTTTG CCCCCCGCCAGGGTATGGGCTG-GATGGTCTCCAGTACAGCGCAGTCCAGGAGGGAA TTCAGCCAGAGAGTAAGAAGAGGGTCGAAGTCAT-TGACTTGACCATCGAAAGCTCA TCAGATGAGGAG-GATTTGCCCCCCACCAAGAAGCACTGCCCTGT-CACCTCAGCGGC CATTCCAGCCCTTCCTG-GAAGCAAAGGAGCCCTGACCTCTGGTCACCAGC-CATCCTC GGTGCTGCG-GAGCCCTGCAATGGGCACACTGGGCAGTGACTTC-CTGTCTAGTCTCCC GCTACATGAGTACC-CACCTGCCTTCCCACTGGGGCGACGA (SEQ ID NO: 42) or a nucleotide sequence at least about 95 percent or at least about 98 percent homologous thereto.

In certain embodiments, a nucleic acid encoding a fragment of a mouse PIAS3 protein that comprises amino acids 400-523 of SEQ ID NO: 1 and a poly-arginine cell penetrating peptide may comprise the nucleotide sequence of SEQ ID NO: 43, as set forth below: ATGGAAGATG-GATCCTGGTGTCCGATGAAACCCAAGAAGGAGG-CATCAGAGGTTTG CCCCCCGCCAGGGTATGGGCTG-GATGGTCTCCAGTACAGCGCAGTCCAGGAGGGAA TTCAGCCAGAGAGTAAGAAGAGGGTCGAAGTCAT-TGACTTGACCATCGAAAGCTCA TCAGATGAGGAG-GATTTGCCCCCCACCAAGAAGCACTGCCCTGT-CACCTCAGCGGC CATTCCAGCCCTTCCTG-GAAGCAAAGGAGCCCTGACCTCTGGTCACCAGC-CATCCTC GGTGCTGCG-GAGCCCTGCAATGGGCACACTGGGCAGTGACTTC-CTGTCTAGTCTCCC GCTACATGAGTACC-CACCTGCCTTCC-CACTGGGGCGACGAAGGCGGCGAAGACGGA GGCGGCATCACCATCATCACCACTAA (SEQ ID NO: 43) or a nucleotide sequence at least about 95 percent or at least about 98 percent homologous thereto.

In certain embodiments, a nucleic acid for use in the present invention encodes a PIAS3 protein comprising the amino acid sequence of SEQ ID NO: 1 or a fragment thereof. For example, and not by way of limitation, a nucleic acid for use in the present invention can encode a PIAS protein that comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 24, SEQ ID NO: 25, SEQ ID NO: 26 or SEQ ID NO: 27 or an amino acid sequence that is at least about 95 percent or at least about 98 percent homologous thereto. In certain embodiments, a nucleic acid for use in the present invention can encode a PIAS protein that comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 24, SEQ ID NO: 25, SEQ ID NO: 26 or SEQ ID NO: 27 or an amino acid sequence that is at least about 95 percent homologous thereto. In certain embodiments, a nucleic acid for use in the present invention can encode a PIAS protein that comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 24, SEQ ID NO: 25, SEQ ID NO: 26 or SEQ ID NO: 27 or an amino acid sequence that is at least about 98 percent homologous thereto. For example, and not by way of limitation, a nucleic acid for use in the present invention can comprise the nucleotide sequence set forth in SEQ ID NOs: 8-10 and 40-43.

In certain embodiments, the PIAS3 protein or a fragment thereof can be associated with enhanced tumor specific activity of a modified virus as described herein, e.g. an oncolytic vaccinia virus.

SOCS3 (Suppressor of Cytokine Signaling 3; Denoted SOCS3 Herein)

In certain embodiments, the modulator of STAT3 activity can be a SOCS3 protein, or a fragment thereof.

In certain embodiments, a SOCS3 protein can be a human SOCS3 protein having an amino acid sequence as set forth in GenBank Accession No. CAG46495.1 or an amino acid sequence at least about 95 percent or at least about 98 percent homologous thereto. In certain embodiments, a human SOCS3 protein that can comprise an amino acid sequence that has the sequence of SEQ ID NO: 28, set forth below: MVTHSKFPAAGMSRPLDTSLRLKTFSSK-SEYQLVVNAVRKLQESGFYWSAVTGGEANL LLSAE-PAGTFLIRDSSDQRHFFTLSVKTQSGTKNL-RIQCEGGSFSLQSDPRSTQPVPRFDC VLKLVHHYMPPPGAPSFPSPPTEPSSEVPEQP-SAQPLPGSPPRRAYYIYSGGEKIPLVLSRP LSSN-VATLQHLCRKTVNGHLDSYEKVTQLPGPIRE-FLDQYDAPL (SEQ ID NO: 28) or an amino acid sequence at least about 95 percent or at least about 98 percent homologous thereto.

In certain embodiments, a nucleic acid encoding a human SOCS3 protein can comprise a nucleic acid sequence as set forth in GenBank Accession No. CR541694.1 or a nucleic acid sequence at least about 95 percent or at least about 98 percent homologous thereto. In certain embodiments, a nucleic acid encoding a human SOCS3 protein comprises the nucleotide sequence of SEQ ID NO: 29, as set forth below: ATGGTCACC-CACAGCAAGTTTCCCGCCGCCGGGAT-GAGCCGCCCCCTGGACACCAG CCTGCGCCTCAA-GACCTTCAGCTCCAAGAGCGAGTACCAGCTGGTG-GTGAACGCAG TGCGCAAGCTGCAG-GAGAGCGGCTTCTACTG-GAGCGCAGTGACCGGCGGCGAGGCG AACCTGCTGCTCAGTGCCGAGCCCGCCGGCACCT-TTCTGATCCGCGACAGCTCGGAC CAGCGC-CACTTCTTCACGCTCAGCGTCAA-GACCCAGTCTGGGACCAAGAACCTGCGC ATCCAGTGT-GAGGGGGGCAGCTTCTCTCTGCAGAGC-GATCCCCGGAGCACGCAGCC CGTGCCCCGCTTCGACTGCGTGCT-CAAGCTGGTGCACCACTACATGCCGCCCCTGG AGCCCCCTCCTTCCCCTCGCCACCTACT-GAACCCTCCTCCGAGGTGCCCGAGCAGCC GTCTGCCCAGCCACTCCCTGG-GAGTCCCCCCAGAAGAGCCTATTACATC-TACTCCGG GGGCGAGAAGATCCCCCTGGTGTT-GAGCCGGCCCCTCTCCTCCAACGTGGCCACTCT TCAGCATCTCTGTCGGAAGACCGTCAACGGC-CACCTGGACTCCTATGAGAAAGTCAC CCAGCTGCCGGGGCCCATTCGG-GAGTTCCTGGACCAGTACGATGCCCCGCTT (SEQ ID NO: 29) or a nucleic acid sequence at least about 95 percent or at least about 98 percent homologous thereto.

In certain embodiments, a SOCS3 protein can be a mouse SOCS3 protein that can comprise an amino acid sequence that has the sequence of SEQ ID NO: 30, set forth below: MVTHSKFPAAGMSRPLDTSLRLKTFSSKSEYQLVV-NAVRKLQESGFYWSAVTGGEANL LLSAEPAGTF-LIRDSSDQRHFFTLSVKTQSGTKNL-RIQCEGGSFSLQSDPRSTQPVPRFDC VLKLVHHYMPPPGTPSFSLPPTEPSSEVPEQP-PAQALPGSTPKRAYYTYSGGEKIPLVLSRP LSSN-VATLQHLCRKTVNGHLDSYEKVTQLPGPIRE-FLDQYDAPL (SEQ ID NO: 30) or an amino acid sequence at least about 95 percent or at least about 98 percent homologous thereto.

In certain embodiments, a nucleic acid encoding a mouse SOCS3 protein comprises the nucleotide sequence of SEQ ID NO: 31, as set forth below: ATGGTCACC-CACAGCAAGTTTCCCGCCGCCGGGAT-GAGCCGCCCCCTGGACACCAG CCTGCGCCTCAA-GACCTTCAGCTCCAAAAGCGAGTACCAGCTGGTG-GTGAACGCCG TGCGCAAGCTGCAGGAGAGCGGAT-TCTACTGGAGCGCCGTGACCGGCGGCGAGGCG AACCTGCTGCTCAGCGCCGAGCCCGCGGGCACCT-TTCTTATCCGCGACAGCTCGGAC CAGCGC-CACTTCTTCACGTTGAGCGTCAA-GACCCAGTCGGGGACCAAGAACCTACG CATCCAGTGT-GAGGGGGGCAGCTTTTCGCTGCAGAGTGACCCCC-GAAGCACGCAGC CAGTTCCCCGCTTCGACTGTGTACT-CAAGCTGGTGCACCACTACATGCCGCCTCCAG GGACCCCCTCCTTTTCTTTGCCACCCACG-GAACCCTCGTCCGAAGTTCCGGAGCAGC CACCTGCCCAGGCACTCCCCGGGAGTACCCC-CAAGAGAGCTTACTACATCTATTCTG GGGGCGAGAAGATTCCGCTGGTACT-GAGCCGACCTCTCTCCTCCAACGTGGCCACCC TCCAGCATCTTTGTCGGAAGACTGTCAACGGC-CACCTGGACTCCTATGAGAAAGTGA CCCAGCTGCCTGGACCCATTCGGGAGTTCCTG-GATCAGTATGATGCTCCACTTTAA (SEQ ID NO: 31) or a nucleic acid sequence at least about 95 percent or at least about 98 percent homologous thereto.

In non-limiting embodiments, a SOCS3 protein of this disclosure can have an amino acid sequence that can be a consecutive portion of SEQ ID NO: 28 or 30, which is at least 20, or at least 30, or at least 40, or at least 50, or at least 60, or at least 70, or at least 80, or at least 90 or at least 100 and up to 200 amino acids in length, or an amino acid sequence at least about 95 percent or at least about 98 percent homologous thereto. In certain embodiments, a SOCS3 protein can have an amino acid sequence that is at least about 95 percent homologous to the sequence of SEQ ID NO: 28 or 30. In certain embodiments, a SOCS3 protein can have an amino acid sequence that is at least about 98 percent homologous to the sequence of 28 or 30.

In certain embodiments, a nucleic acid for use in this disclosure encodes a SOCS3 protein or a fragment thereof. For example, and not by way of limitation, a nucleic acid for use in this disclosure can encode a SOCS3 protein that comprises the amino acid sequence of SEQ ID NO: 28 or SEQ ID NO: 30 or an amino acid sequence that is at least about 95 percent or at least about 98 percent homologous thereto. For example, and not by way of limitation, a nucleic acid for use in this disclosure can comprise the nucleotide sequence set forth in SEQ ID NOs: 29 and 31, or a nucleotide sequence at least about 95 percent or at least about 98 percent homologous thereto. In certain embodiments, a nucleic acid for use in this disclosure can comprise the nucleotide sequence set forth in SEQ ID NOs: 29 and 31, or a nucleotide sequence at least about 95 percent homologous thereto. In certain embodiments, a nucleic acid for use in this disclosure can comprise the nucleotide sequence set forth in SEQ ID NOs: 29 and 31, or a nucleotide sequence at least about 98 percent homologous thereto.

TCPTP (T-Cell Protein Tyrosine Phosphatase; Denoted as TCPTP Herein)

In certain embodiments, the modulator of STAT3 activity can be a TCPTP protein.

In certain embodiments, a TCPTP protein can be a human TCPTP isoform 2 protein having an amino acid sequence as set forth in NCBI/UniProtKB Accession No. NP 536347.1 or an amino acid sequence at least about 95 percent or at least about 98 percent homologous thereto. In certain embodiments, a human TCPTP isoform 2 protein can comprise an amino acid sequence that has the sequence of SEQ ID NO: 32, set forth below: MPTTIERE-FEELDTQRRWQPLYLEIRNESHDYPHR-VAKFPENRNRNRYRDVSPYDHSRV KLQNAENDYI-NASLVDIEEAQRSYILTQGPLPNTCCHFWLMVWQQ-KTKAVVMLNRIVE KESVK-CAQYWPTDDQEMLFKETGFSVKLLSEDVKSYYTV-HLLQLENINSGETRTISHFH YTTWPDFGVPESPASFLN-FLFKVRESGSLNPDHGPAVIHCSAGIGRSGTFSLVDT-CLVLM EKGDDINIKQVLLNMRKYRMGLI QTPDQLRFSYMAIIEGAKCIKGDSSIQKRWKELSKED LSPAFDHSPNKIMTEKYNGNRI-GLEEEKLTGDRCTGLSSKMQDTMEENSESALRKRI-RED RKATTAQKVQQMKQRLNENERKRKRPRLTDT (SEQ ID NO: 32) or an amino acid sequence at least about 95 percent or at least about 98 percent homologous thereto.

In certain embodiments, a nucleic acid encoding a human TCPTP isoform 2 protein can comprise a nucleic acid sequence as set forth in NCBI/UniProtKB Accession No. NM 080422.2 or a nucleic acid sequence at least about 95 percent or at least about 98 percent homologous thereto. In certain embodiments, a nucleic acid encoding a human TCPTP isoform 2 protein can comprise the nucleotide sequence of SEQ ID NO: 33, as set forth below: GCTCGGGCGCCGAGTCTGCGCGCTGACGTCCGAC-GCTCCAGGTACTTTCCCCACGGC CGACAGGGCTTGGCGTGGGGGCGGGGCGCGGCG-CGCAGCGCGCATGCGCCGCAGC GCCAGCGCTCTCCCCGGATCGTGCGGGGCCT-GAGCCTCTCCGCCGGCGCAGGCTCTG CTCGCGCCAGCTCGCTCCCGCAGCCATGCCCAC-CACCATCGAGCGGGAGTTCGAAG AGTTGGA-TACTCAGCGTCGCTGGCAGCCGCTGTACTTG-GAAATTCGAAATGAGTCCC ATGACTATCCTCATAGAGTGGC-CAAGTTTCCAGAAAACAGAAATCGAAACAGATAC AGAGATGTAAGCCCATATGATCACAGTCGTGT-TAAACTGCAAAATGCTGAGAATGA TTATAT-TAATGCCAGTTTAGTTGACAT-AGAAGAGGCACAAAGGAGTTACATCTTAAC ACAGGGTCCACTTCCTAACACATGCTGCCAT-TTCTGGCTTATGGTTTGGCAGCAGAA GAC-CAAAGCAGTTGTCATGCTGAACCGCATTGTG-GAGAAAGAATCGGTTAAATGTG CACAGTACTGGCCAACAGATGAC-CAAGAGATGCTGTTTAAAGAAACAGGATTCAGT GTGAAGCTCTTGTCAGAAGATGTGAAGTCGTAT-TATACAGTACATCTACTACAATTA GAAAATAT-CAATAGTGGTGAAACCAGAACAATATCTCACTTT-CATTATACTACCTGG CCAGATTTTGGAGTCCCTGAATCACCAGCTTCAT-TTCTCAATTTCTTGTTTAAAGTGA GAGAATCTGGCTCCTTGAACCCTGAC-CATGGGCCTGCGGTGATCCACTGTAGTGCAG GCAT-TGGGCGCTCTGGCACCTTCTCTCTGGTA-GACACTTGTCTTGTTTTGATGGAAAA AGGAGATGATATTAACATAAAACAAGTGTTACT-GAACATGAGAAAATACCGAATGG GTCTTATTCA-GACCCCAGATCAACTGAGATTCTCATACATGGC-TATAATAGAAGGAG CAAAATGTATAAAGGGAGATTCTAGTATA-CAGAAACGATGGAAAGAACTTTCTAAG GAAGACT-TATCTCCTGCCTTTGATCATTCAC-CAAACAAAATAATGACTGAAAAATAC AATGGGAACAGAATAGGTCTAGAAGAAGAAAA ACTGACAGGTGACCGATGTACAG GACTTTCCTCTAAAATGCAAGATACAATGGAG-GAGAACAGTGAGAGTGCTCTACGG AAACGTAT-TCGAGAGGACAGAAAGGCCAC-CACAGCTCAGAAGGTGCAGCAGATGA AACAGAGGCTAAATGAGAAT-GAACGAAAAAGAAAAAGGCCAAGATTGACA-GACAC CTAATATTCATGACTTGAGAATAT-TCTGCAGCTATAAATTTTGAACCATTGATGTGC AAAGCAAGACCTGAAGCCCACTCCG-GAAACTAAAGTGAGGCTCGCTAACCCTCTAG ATTGCCTCACAGTTGTTTGTTTACAAAGTAAACTT-TACATCCAGGGGATGAAGAGCA CCCACCAGCAGAAGACTTTGCAGAACCTTTAATTG-GATGTGTTAAGTGTTTTTAATG AGTGTAT-GAAATGTAGAAAGATGTACAAGAAATAAATT-AGGGGAGATTACTTTGTA TTGTACTGCCATTCCTACTGTATTTT-TATACTTTTTGGCAGCATTAAATATTTTTGTTA AATAGTCAAAAAAAAAAAAAAAAAA (SEQ ID NO: 33) or a nucleic acid sequence at least about 95 percent or at least about 98 percent homologous thereto.

In certain embodiments, a mouse TCPTP isoform 2 protein can comprise an amino acid sequence that has the sequence of SEQ ID NO: 34, set forth below: MSATIERE-FEELDAQCRWQPLYLEIRNESHDYPHR-VAKFPENRNRNRYRDVSPYDHSRV KLQSTENDYI-NASLVDIEEAQRSYILTQGPLPNTCCHFWLMVWQQ-KTKAVVMLNRTVE KESVKCAQYWPTD-DREMVFKETGFSVKLLSEDVKSYYTVHLLQLENINT-GETRTISHFH YTTWPDFGVPESPASELN-FLEKVRESGCLTPDHGPAVIHCSAGIGRSGTFSLVDT-CLVLM EKGEDVNVKQLLLNMRKYRMGLIQTPDQLRFSY-MAIIEGAKYTKGDSNIQKRWKELSK EDL-SPICDHSQNRVMVEKYN-GKRIGSEDEKLTGLPSKVQDTVEESSESILRKRIREDR-KATTAQKVQQMKQRLNETERKRKRPRLTDT (SEQ ID NO: 34) or an amino acid sequence at least about 95 percent or at least about 98 percent homologous thereto.

In certain embodiments, a nucleic acid encoding a mouse TCPTP isoform 2 protein can comprises the nucleotide sequence of SEQ ID NO: 35, as set forth below: ATGAGCGCCACTATTGAGCGGGAGTTCGAG-GAACTGGACGCCCAGTGTAGATGGCA GCCCCTT-TATCTTGAGATACGCAACGAAAGTCACGAT-TACCCTCATAGGGTAGCTAA ATTCCCTGAGAACAGAAACAGAAACCGCTACCGC-GATGTGTCACCCTACGATCACT CCAGAGT-GAAACTTCAAAGTACCGAAAATGAT-TATATAAATGCCAGCTTGGTGGAC ATAGAGGAAGCCCAAAGATCATACATACTTACT-CAAGGGCCTCTCCCAAACACTTGT TGCCAT-TTCTGGCTCATGGTGTGGCAACAGAAGAC-CAAGGCTGTGGTAATGCTCAAT CGGACTGTGGAAAAAGAGTCAGTAAAGTGTGCT-CAATATTGGCCAACTGATGATAG GGAGATGGTCTT-TAAGGAAACAGGTTTCTCCGTTAAGTTGCTCAGT-GAGGATGTGAA GTCCTATTACACAGTACATCTTCTCCAATTG-GAGAACATCAACACCGGTGAAACCCG AACAATATCCCACTTTCATTATAC-CACTTGGCCTGACTTCGGTGTTCCTGAAAGCCCC GCTTCTTTTCTCAATTTCCTGTTTAAGGTGCGG-GAGTCAGGCTGTCTCACCCCAGATC ATGGGCCTGCTGTAATACATTGTAGCGCTGG-GATCGGGCGATCCGGGACATTCTCTT TGGTA- GACACTTGCCTGGTCCTGATGGAGAAGG-GAGAGGACGTAAACGTTAAGCAG TTGCTCCTGAATATGAGAAAATATCGAATGGGGTT-GATTCAGACTCCCGATCAACTT AGATTCTCT-TATATGGCTATAATCGAGGGCGCAAAATATAC-CAAGGGGGACTCCAA CATTCAAAAAAGATGGAAGGAGCTCTCTAAGGAA-GATCTGTCTCCAATCTGTGACC ACAGTCAGAACCGAGTTATGGTAGAGAAATA-CAACGGTAAAAGAATTGGCTCAGAA GACGAAAAACTGACCGGACTCCCCTC-CAAAGTGCAAGATACAGTCGAAGAATCATC CGAGTCAATCTTGAGGAAAAGAATCAGGGAA-GATCGGAAGGCCACTACAGCCCAAA AAGTGCAACAAATGAAACAGCGACT-CAACGAAACAGAGCGGAAACGAAAACGGCC AAGACTGACAGACACCTAA (SEQ ID NO: 35) or a nucleic acid sequence at least about 95 percent or at least about 98 percent homologous thereto.

In certain embodiments, a TCPTP protein of this disclosure can have an amino acid sequence that can be a consecutive portion of SEQ ID NO: 32 or 34, which is at least 20, or at least 30, or at least 40, or at least 50, or at least 60, or at least 70, or at least 80, or at least 90 or at least 100 and up to 200 amino acids in length, or an amino acid sequence at least about 95 percent or at least about 98 percent homologous thereto. In certain embodiments, a TCPTP protein can have an amino acid sequence that is at least about 95 percent homologous to the sequence of SEQ ID NO: 32 or 34. In certain embodiments, a TCPTP protein can have an amino acid sequence that is at least about 98 percent homologous to the sequence of 32 or 34.

In certain embodiments, a nucleic acid for use in the present invention encodes a TCPTP protein. For example, and not by way of limitation, a nucleic acid for use in the present invention can encode a TCPTP protein, i.e., TCPTP isoform 2 protein, that comprises the amino acid sequence of SEQ ID NO: 32 or SEQ ID NO: 34 or an amino acid sequence that is at least about 95 percent or at least about 98 percent homologous thereto. In certain embodiments, a nucleic acid for use in this disclosure can comprise the nucleotide sequence set forth in SEQ ID NOs: 33 and 35, or a nucleotide sequence at least about 95 percent homologous thereto. In certain embodiments, a nucleic acid for use in this disclosure can comprise the nucleotide sequence set forth in SEQ ID NOs: 33 and 35, or a nucleotide sequence at least about 98 percent homologous thereto. For example, and not by way of limitation, a nucleic acid for use in the present invention can comprise the nucleotide sequence set forth in SEQ ID NOs: 33 and 35.

STAT3 Containing Dominant-Negative Mutations

In certain embodiments, the modulator of STAT3 activity can be a STAT3 protein with one or more dominant-negative mutations. In certain embodiments, the dominant-negative mutant STAT3 protein can be a dominant-negative mutant human STAT3 protein.

In certain embodiments, a dominant-negative mutant human STAT3 protein can have a mutation at amino acid 705, e.g., Y705F. For example, and not by way of limitation, a dominant-negative mutant STAT3 protein can comprise an amino acid sequence that has the sequence of SEQ ID NO: 36, set forth below: MAQWNQLQQLDTRYLEQLHQLYSDSFPMELRQ-FLAPWIESQDWAYAASKESHATLVF HNLLGEIDQQYSRFLQESNVLYQHNLR-RIKQFLQSRYLEKPMEIARIVARCLWEESRLLQ TAATAAQQGGQANHPTAAVVTEKQQM-LEQHLQDVRKRVQDLEQKMKVVENLQDDFD FNYKTLKSQGDMQDLNG-NNQSVTRQKMQQLEQMLTALDQMRRSIVSELAGLL-SAMEY VQKTLTDEELADWKRRQQIACIGGPPNICL-DRLENWITSLAESQLQTRQQIKKLEELQQK VSYKGDPIVQHRPMLEERIVELFRNLMKSAFVVER-QPCMPMHPDRPLVIKTGVQFTTKV RLL-VKFPELNYQLKIKVCIDKDSGDVAALRGSRKF-NILGTNTKVMNMEESNNGSLSAEF KHLTLREQRCGNGGRANCDASLIVTEELHLITFETE-VYHQGLKIDLETHSLPVVVISNICQ MPNA-WASILWYNMLTNNPKNVNFFTKPPIGTWDQ-VAEVLSWQFSSTTKRGLSIEQLTTL AEKLLGPGVNYSGCQITWAKFCKEN-MAGKGFSFWVWLDNIIDLVKKYILALWNEGYIM GFISKERERAILSTKPPGTFLLRFSESSKEG-GVTFTWVEKDISGKTQIQSVEPYTKQQLNN MSFAEIIMGYKIMDATNILVSPLVYLYPDIPKEE-AFGKYCRPESQEHPEADPGAAPFLKT KFICVTPTTCSNTIDLPMSPRTLDSLMQFGNNGEGAE-PSAGGQFESLTFDMELTSECATSP M (SEQ ID NO: 36) or an amino acid sequence at least about 95 percent or at least about 98 percent homologous thereto.

In certain embodiments, SEQ ID NO: 36 can be encoded by the nucleotide sequence of SEQ ID NO: 37, as set forth below: ATGGCCCAATGGAATCAGCTA-CAGCAGCTTGACACACGGTACCTGGAGCAGCTCCA TCAGCTCTACAGTGACAGCTTCCCAATG-GAGCTGCGGCAGTTTCTGGCCCCTTGGAT TGAGAGTCAAGATTGGG-CATATGCGGCCAGCAAAGAATCACATGC-CACTTTGGTGTT TCATAATCTCCTGGGAGAGAT-TGACCAGCAGTATAGCCGCTTCCTGCAAGAGTCG-AA TGTTCTCTATCAGCACAATCTACGAAGAAT-CAAGCAGTTTCTTCAGAGCAGGTATCT TGAGAAGCCAATGGAGATTGCCCGGAT-TGTGGCCCGGTGCCTGTGGGAAGAATCAC GCCTTCTACAGACTGCAGC-CACTGCGGCCCAGCAAGGGGGCCAGGCCAAC-CACCCC ACAGCAGCCGTGGTGACG-GAGAAGCAGCAGATGCTGGAGCAGCACCTTCAGG-ATGT CCGGAAGAGAGTGCAG-GATCTAGAACAGAAAAT-GAAAGTGGTAGAGAATCTCCAG GATGACTTTGAT-TTCAACTATAAAACCCTCAAGAGTCAAGGAGACA-TGCAAGATCTG AATG-GAAACAACCAGTCAGTGACCAGGCAGAA-GATGCAGCAGCTGGAACAGATGCT CACTGCGCTGGACCAGATGCGGAGAAGCATCGT-GAGTGAGCTGGCGGGGCTTTTGT CAGCGATG-GAGTACGTGCAGAAAACTCTCACGGACGAG-GAGCTGGCTGACTGGAAG AGGCGGCAACAGATTGCCTGCATTG-GAGGCCCGCCCAACATCTGCCTAGATCGGCT AGAAAACTGGATAACGTCATTAGCAGAATCT-CAACTTCAGACCCGTCAACAAATTA AGAAACTG-GAGGAGTTGCAGCAAAAAGTTTCCTA-CAAAGGGGACCCCATTGTACAG CACCGGCCGATGCTGGAGGAGAGAATCGTG-GAGCTGTTTAGAAACTTAATGAAAAG TGCCTTTGTGGTGGAGCGGCAGCCCTGCATGCC-CATGCATCCTGACCGGCCCCTCGT CATCAA-GACCGGCGTCCAGTTCAC-TACTAAAGTCAGGTTGCTGGTCAAATTCCCTGA GTTGAATTATCAGCTTAAAATTAAAGTGTGCAT-TGACAAAGACTCTGGGGACGTTGC AGCTCTCAGAGGATCCCGGAAATTTAACAT-TCTGGGCACAAACACAAAAGTGATGA ACATG- GAAGAATCCAACAACGGCAGCCTCTCTGCAGAATTCAAACACTTGACCCTG
AGGGAGCAGAGATGTGGGAATGGGGGCCGAGCCAATTGTGATGCTTCCCTGATTGT GACTGAGGAGCTGCACCTGATCACCTTTGAGACCGAGGTGTATCACCAAGGCCTCA AGATTGACCTAGAGACCCACTCCTTGCCAGTTGTGGTGATCTCCAACATCTGTCAGA TGCCAAATGCCTGGGCGTCCATCCTGTGGTACAACATGCTGACCAACAATCCCAAGA ATGTAAACTTTTTTACCAAGCCCCCAATTGGAACCTGGGATCAAGTGGCCGAGGTCCTGAGCTGGCAGTTCTCCTCCACCACCAAGCGAGGACTGAGCATCGAGCAGCTGACT ACACTGGCAGAGAAACTCTTGGGACCTGGTGTGAATTATTCAGGGTGTCAGATCACA TGGGCTAAATTTTGCAAAGAAAACATGGCTGGCAAGGGCTTCTCCTTCTGGGTCTGG CTGGACAATATCATTGACCTTGTGAAAAAGTACATCCTGGCCCTTTGGAACGAAGGG TACATCATGGGCTTTATCAGTAAGGAGCGGGAGCGGGCCATCTTGAGCACTAAGCCT CCAGGCACCTTCCTGCTAAGATTCAGTGAAAGCAGCAAAGAAGGAGGCGTCACTTT CACTTGGGTGGAGAAGGACATCAGCGGTAAGACCCAGATCCAGTCCGTGGAACCAT ACACAAAGCAGCAGCTGAACAACATGTCATTTGCTGAAATCATCATGGGCTATAAG ATCATGGATGCTACCAATATCCTGGTGTCTCCACTGGTCTATCTCTATCCTGACATTC CCAAGGAGGAGGCATTCGGAAAGTATTGTCGGCCAGAGAGCCAGGAGCATCCTGAA GCTGACCCAGGCGCTGCCCCATTCCTGAAGACCAAGTTTATCTGTGTGACACCAACG ACCTGCAGCAATACCATTGACCTGCCGATGTCCCCCCGCACTTTAGATTCATTGATG CAGTTTGGAAATAATGGTGAAGGTGCTGAACCCTCAGCAGGAGGGCAGTTTGAGTC CCTCACCTTTGACATGGAGTTGACCTCGGAGTGCGCTACCTCCCCCATGTGA (SEQ ID NO: 37) or a nucleic acid sequence at least about 95 percent or at least about 98 percent homologous thereto.

In certain embodiments, a dominant-negative mutant STAT3 protein can have one or more mutations at amino acids 434 and/or 435, e.g., E434A and E435A. For example, and not by way of limitation, a dominant-negative mutant human STAT3 protein comprises an amino acid sequence that has the sequence of SEQ ID NO: 38, set forth below:
MAQWNQLQQLDTRYLEQLHQLYSDSFPMELRQFLAPWIESQDWAYAASKESHATLVF HNLLGEIDQQYSRFLQESNVLYQHNLRRIKQFLQSRYLEKPMEIARIVARCLWEESRLLQ TAATAAQQGGQANHPTAAVVTEKQQMLEQHLQDVRKRVQDLEQKMKVVENLQDDFD FNYKTLKSQGDMQDLNGNNQSVTRQKMQQLEQMLTALDQMRRSIVSELAGLLSAMEY VQKTLTDEELADWKRRQQIACIGGPPNICLDRLENWITSLAESQLQTRQQIKKLEELQQK VSYKGDPIVQHRPMLEERIVELFRNLMKSAFVVERQPCMPMHPDRPLVIKTGVQFTTKV RLLVKFPELNYQLKIKVCIDKDSGDVAALRGSRKFNILGTNTKVMNMEESNNGSLSAEF KHLTLREQRCGNGGRANCDASLIVTAALHLITFETEVYHQGLKIDLETHSLPVVVISNIC QMPNAWASILWYNMLTNNPKNVNFFTKPPIGTWDQVAEVLSWQFSSTTKRGLSIEQLT TLAEKLLGPGVNYSGCQITWAKFCKENMAGKGFSFWVWLDNIIDLVKKYILALWNEGY IMGFISKERERAILSTKPPGTFLLRFSESSKEGGVTFTWVEKDISGKTQIQSVEPYTKQQLN NMSFAEIIMGYKIMDATNILVSPLVYLYPDIPKEEAFGKYCRPESQEHPEADPGAAPYLK TKFICVTPTTCSNTIDLPMSPRTLDSLMQFGNNGEGAEPSAGGQFESLTFDMELTSECATS PM (SEQ ID NO: 38) or an amino acid sequence at least about 95 percent or at least about 98 percent homologous thereto.

In certain embodiments, SEQ ID NO: 38 can be encoded by the nucleotide sequence of SEQ ID NO: 39, as set forth below: ATGGCCCAATGGAATCAGCTACAGCAGCTTGACACACGGTACCTGGAGCAGCTCCA TCAGCTCTACAGTGACAGCTTCCCAATGGAGCTGCGGCAGTTTCTGGCCCCTTGGAT TGAGAGTCAAGATTGGGCATATGCGGCCAGCAAAGAATCACATGCCACTTTGGTGTT TCATAATCTCCTGGGAGAGATTGACCAGCAGTATAGCCGCTTCCTGCAAGAGTCGAA TGTTCTCTATCAGCACAATCTACGAAGAATCAAGCAGTTTCTTCAGAGCAGGTATCT TGAGAAGCCAATGGAGATTGCCCGGATTGTGGCCCGGTGCCTGTGGGAAGAATCAC GCCTTCTACAGACTGCAGCCACTGCGGCCCAGCAAGGGGGCCAGGCCAACCACCCC ACAGCAGCCGTGGTGACGGAGAAGCAGCAGATGCTGGAGCAGCACCTTCAGGATGT CCGGAAGAGAGTGCAGGATCTAGAACAGAAAAT
GAAAGTGGTAGAGAATCTCCAG GATGACTTTGATTTCAACTATAAAACCCTCAAGAGTCAAGGAGACATGCAAGATCTG AATGGAAACAACCAGTCAGTGACCAGGCAGAAGATGCAGCAGCTGGAACAGATGCT CACTGCGCTGGACCAGATGCGGAGAAGCATCGTGAGTGAGCTGGCGGGGCTTTTGT CAGCGATGGAGTACGTGCAGAAAACTCTCACGGACGAGGAGCTGGCTGACTGGAAG AGGCGGCAACAGATTGCCTGCATTGGAGGCCCGCCCAACATCTGCCTAGATCGGCT AGAAAACTGGATAACGTCATTAGCAGAATCTCAACTTCAGACCCGTCAACAAATTA AGAAACTGGAGGAGTTGCAGCAAAAAGTTTCCTACAAAGGGGACCCCATTGTACAG CACCGGCCGATGCTGGAGGAGAGAATCGTGGAGCTGTTTAGAAACTTAATGAAAAG TGCCTTTGTGGTGGAGCGGCAGCCCTGCATGCCCATGCATCCTGACCGGCCCCTCGT CATCAAGACCGGCGTCCAGTTCACTACTAAAGTCAGGTTGCTGGTCAAATTCCCTGA GTTGAATTATCAGCTTAAAATTAAAGTGTGCATTGACAAAGACTCTGGGGACGTTGC AGCTCTCAGAGGATCCGGAAATTTAACATTCTGGGCACAAACACAAAAGTGATGA ACATGGAAGAATCCAACAACGGCAGCCTCTCTGCAGAATTCAAACACTTGACCCTG
AGGGAGCAGAGATGTGGGAATGGGGGCCGAGCCAATTGTGATGCTTCCCTGATTGT GACTGCGGCGCTGCACCTGATCACCTTTGAGACCGAGGTGTATCACCAAGGCCTCA AGATTGACCTAGAGACCCACTCCTTGCCAGTTGTGGTGATCTCCAACATCTGTCAGA TGCCAAATGCCTGGGCGTCCATCCTGTGGTACAACATGCTGACCAACAATCCAAGA ATGTAAACTTTTTTACCAAGCCCCCAATTGGAACCTGGGATCAAGTGGCCGAGGTCC TGAGCTGGCAGTTCTCCTCCACCAC- CAAGCGAGGACTGAGCATCGAGCAGCTGACTACACTGGCAGAGAAACTCTTGGGACCTGGTGTGAATTATTCAGGGTGTCAGATCACA TGGGCTAAATTTTGCAAAGAAAACATGGCTGGCAAGGGCTTCTCCTTCTGGGTCTGGCTGGACAATATCATTGACCTTGTGAAAAAGTACATCCTGGCCCTTTGGAACGAAGGG TACATCATGGGCTTTATCAGTAAGGAGCGGGAGCGGGCCATCTTGAGCACTAAGCCTCCAGGCACCTTCCTGCTAAGATTCAGTGAAAGCAGCAAAGAAGGAGGCGTCACTTTCACTTGGGTGGAGAAGGACATCAGCGGTAAGACCCAGATCCAGTCCGTGGAACCATACACAAAGCAGCAGCTGAACAACATGTCATTTGCTGAAATCATCATGGGCTATAAG ATCATGGATGCTACCAATATCCTGGTGTCTCCACTGGTCTATCTCTATCCTGACATTCCCAAGGAGGAGGCATTCGGAAAGTATTGTCGGCCAGAGAGCCAGGAGCATCCTGAAGCTGACCCAGGCGCTGCCCCATACCTGAAGACCAAGTTTATCTGTGTGACACCAACGACCTGCACAATACCATTGACCTGCCGATGTCCCCCCGCACTTTAGATTCATTGATGCAGTTTGGAAATAATGGTGAAGGTGCTGAACCCTCAGCAGGAGGGCAGTTTGAGTC CCTCACCTTTGACATGGAGTTGACCTCGGAGTGCGCTACCTCCCCCATGTGA (SEQ ID NO: 39) or a nucleotide sequence at least about 95 percent or at least about 98 percent homologous thereto.

In certain embodiments, a nucleic acid for use in this disclosure can encode a dominant-negative mutant STAT3 protein. For example, and not by way of limitation, a nucleic acid for use in this disclosure can encode a dominant-negative mutant STAT3 protein that comprises the amino acid sequence of SEQ ID NO: 36 or SEQ ID NO: 38 or an amino acid sequence that is at least about 95 percent or at least about 98 percent homologous thereto. In certain embodiments, a dominant-negative mutant STAT3 protein can have an amino acid sequence that is at least about 95 percent homologous to the sequence of SEQ ID NO: 36 or 38. In certain embodiments, a dominant-negative mutant STAT3 protein can have an amino acid sequence that is at least about 98 percent homologous to the sequence of 36 or 38. In certain embodiments, a nucleic acid for use in this disclosure can comprise the nucleotide sequence set forth in SEQ ID NOs: 37 and 39, or a nucleotide sequence at least about 95 percent homologous thereto. In certain embodiments, a nucleic acid for use in this disclosure can comprise the nucleotide sequence set forth in SEQ ID NOs: 37 and 39, or a nucleotide sequence at least about 98 percent homologous thereto.

In certain embodiments, an oncolytic virus can comprise an amino acid sequence that is 95% homologous to the amino acid sequence of any one of SEQ ID NOs: 1-7, 11, 14, 16, 18, 20, 22, 24-28, 30, 32, 34, 36 and 38. In certain embodiments, an oncolytic virus can comprise an amino acid sequence that is 98% homologous to the amino acid sequence of any one of SEQ ID NOs: 1-7, 11, 14, 16, 18, 20, 22, 24-28, 30, 32, 34, 36 and 38.

In certain embodiments, an oncolytic virus can comprise a nucleotide sequence that is 95% homologous to the nucleotide sequence of any one of SEQ ID NOs: 8-10, 12-13, 15, 17, 19, 21, 23, 29, 31, 33, 35, 37 and 39-43. In certain embodiments, an oncolytic virus can comprise a nucleotide sequence that is 98% homologous to the nucleotide sequence of any one of SEQ ID NOs: 8-10, 12-13, 15, 17, 19, 21, 23, 29, 31, 33, 35, 37 and 39-43.

In certain embodiments, changes to the amino acid sequence of the PIAS3, SOCS3, or TCPTP proteins set forth above can be made where the resulting protein maintains the ability to function as modulator of STAT3. In certain embodiments, such changes are referred to as conservative substitutions. As used herein, the terms "conservative substitutions" and "conservative modifications" refer to amino acid modifications that do not significantly affect or alter the binding characteristics of the presently disclosed STAT3 modulator proteins comprising the amino acid sequence. Such conservative modifications include amino acid substitutions, additions and deletions. Modifications can be introduced into the STAT3 modulator proteins of this disclosure by standard techniques known in the art, such as site-directed mutagenesis and PCR-mediated mutagenesis. Amino acids can be classified into groups according to their physicochemical properties such as charge and polarity.

Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within the disclosed STAT3 modulators can be replaced with other amino acid residues from the same group and the altered STAT3 modulator protein can be tested for retained function using the functional assays described herein. In certain embodiments, no more than one, no more than two, no more than three, no more than four, no more than five residues within a specified sequence are altered. Exemplary conservative amino acid substitutions are shown in Table 1.

TABLE 1

| Original Residue | Exemplary Conservative Amino Acid Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe |
| Leu (L) | Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala |

Cancer Targets

In certain embodiments of this disclosure, a method of treatment for a hyperproliferative disease, such as a cancer or a tumor, by the delivery of a modified virus, such as an oncolytic vaccinia virus as described herein, is contemplated. Cancers that can be treated by a modified virus, e.g., a modified vaccinia virus that can comprise an exogenous nucleic acid coding for a modulator of STAT3-mediated gene-activation of this disclosure can include, but are not limited to, melanoma, hepatocellular carcinoma, breast cancer, lung cancer, prostate cancer, bladder cancer, ovarian cancer, leukemia, lymphoma, renal carcinoma, pancreatic cancer, epithelial carcinoma, gastric cancer, colon carcinoma, duodenal cancer, pancreatic adenocarcinoma, mesothelioma, glioblastoma multiforme, astrocytoma, multiple myeloma, prostate carcinoma, hepatocellular carcinoma, cholangiosarcoma, pancreatic adenocarcinoma, head and neck squamous cell carcinoma, colorectal cancer, intestinal-type gastric adenocarcinoma, cervical squamous-cell carcinoma, osteosarcoma, epithelial ovarian carcinoma, acute lymphoblastic lymphoma, myeloproliferative neoplasms, and sarcoma.

Cancer cells that can be treated by the methods of this disclosure include cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In various examples, the modulator of STAT3-mediated gene-activation of, for use in a modified virus of this disclosure, such as an oncolytic vaccinia virus, that can be used to treat cancer targets disclosed herein, can be a PIAS3 protein or a fragment thereof, a SOCS3 protein or a fragment thereof, a TCPTP protein or a fragment thereof, a STAT3 protein or a fragment thereof, e.g., a STAT3 protein that can comprise a dominant-negative mutation.

This disclosure also contemplates methods for inhibiting or preventing local invasiveness or metastasis, or both, of any type of primary cancer. For example, the primary cancer can be melanoma, non-small cell lung, small-cell lung, lung, hepatocarcinoma, retinoblastoma, astrocytoma, glioblastoma, gum, tongue, leukemia, neuroblastoma, head, neck, breast, pancreatic, prostate, renal, bone, testicular, ovarian, mesothelioma, cervical, gastrointestinal, lymphoma, brain, colon, or bladder. In certain embodiments, the primary cancer can be lung cancer. For example, and not by way of limitation, the lung cancer can be non-small cell lung carcinoma. Moreover, this disclosure can be used to prevent cancer or to treat pre-cancers or premalignant cells, including metaplasias, dysplasias, and hyperplasias. It can also be used to inhibit undesirable but benign cells, such as squamous metaplasia, dysplasia, benign prostate hyperplasia cells, hyperplastic lesions, and the like. In certain embodiments, the progression to cancer or to a more severe form of cancer can be halted, disrupted, or delayed by methods of this disclosure involving STAT3 modulating agents that can be encoded by a modified virus, such as an oncolytic vaccinia virus, as discussed herein. In various examples, the modulator of STAT3-mediated gene-activation of, for use in a modified virus of this disclosure, such as an oncolytic vaccinia virus, that can be used for inhibiting or preventing local invasiveness or metastasis, or both, of any type of primary cancer, can be a PIAS3 protein or a fragment thereof, a SOCS3 protein or a fragment thereof, a TCPTP protein or a fragment thereof, a STAT3 protein or a fragment thereof, e.g., a STAT3 protein that can comprise a dominant-negative mutation.

Methods of Treatment and Assaying the Efficacy and Pharmacokinetics

The present disclosure provides methods for treating a subject by administration of one or more modified viruses, as disclosed herein. An "individual" or "subject," as used interchangeably herein, refers to a human or a non-human subject. Non-limiting examples of non-human subjects include non-human primates, dogs, cats, mice, rats, guinea pigs, rabbits, pigs, fowl, horses, cows, goats, sheep, cetaceans, etc. In certain embodiments, the subject is human.

The present disclosure provides methods of producing a toxic effect in a cancer cell comprising administering, to the cancer cell, a therapeutically effective amount of a modified virus, such as an oncolytic vaccinia virus, as described above, or a pharmaceutical composition containing the same. This disclosure further provides a method of inhibiting at inhibiting the growth and/or proliferation of a second cancer cell comprising administering, to a first cancer cell, a modified virus as described above such that the first cancer cell is infected with said virus. Thus, in certain embodiments of the methods disclosed here, it is contemplated that not every cancer or tumor cell is infected upon administering a therapeutically effective amount of an oncolytic vaccinia virus, as described herein, or a pharmaceutical composition containing the same, and growth of non-infected cells can be inhibited without direct infection.

In certain embodiments, to induce oncolysis, kill cells, inhibit growth, inhibit metastases, decrease tumor size and otherwise reverse or reduce the malignant phenotype of tumor cells, using the methods and compositions of the present disclosure, a cancer cell or a tumor can be contacted with a therapeutically effective dose of an exemplary oncolytic vaccinia virus as described herein or a pharmaceutical composition containing the same. In certain embodiments, an effective amount of a modified virus of the present disclosure, such as an oncolytic vaccinia virus as described herein or a pharmaceutical composition thereof, can include an amount sufficient to induce oncolysis, the disruption or lysis of a cancer cell or the inhibition or reduction in the growth or size of a cancer cell. Reducing the growth of a cancer cell may be manifested, for example, by cell death or a slower replication rate or reduced growth rate of a tumor comprising the cell or a prolonged survival of a subject containing the cancer cell.

The present disclosure further provides a method of at least partially re-sensitizing a cancer patient to a cancer therapy, comprising administering to a subject in need thereof a therapeutically effective amount of an oncolytic vaccinia virus disclosed herein or a pharmaceutical composition disclosed herein, in combination with a drug that enhances the replication of the vaccinia virus within tumor cells.

Provided, in certain embodiments, is a method of treating a subject having a cancer or a tumor, comprising administering, to the subject, an effective amount of a modified virus, as described above. An effective amount in such method can include an amount that reduces growth rate or spread of the cancer or that prolongs survival in the subject. This disclosure provides a method of reducing the growth of a tumor, which method can comprise administering, to the tumor, an effective amount of a modified virus as described above. In certain embodiments, an effective amount of a modified virus, or a pharmaceutical composition thereof, can include an amount sufficient to induce the slowing, inhibition or reduction in the growth or size of a tumor and can include the eradication of the tumor. Reducing the growth of a tumor may be manifested, for example, by reduced growth rate or a prolonged survival of a subject containing the tumor.

This disclosure also provides a method of determining the infectivity or anti-tumor activity of an oncolytic vaccinia virus as described herein, which method can comprise (i) collecting a first biological sample from a subject and determining the level of STAT3 in the first biological sample; (ii) administering to the subject a therapeutically effective amount of an oncolytic vaccinia virus or a pharmaceutical composition according to the present disclosure, alone or in combination with a further therapy; (iii) collecting a second biological sample from the subject after about 15 mins to about 72 hours following the administration in step (ii) and (iii) detecting the level of a STAT3 protein in the second biological sample, wherein the oncolytic vaccinia virus is determined to be infective or demonstrate anti-tumor activity if the level of STAT3 is lower in step (iii) than in step (i). In certain embodiments, the method disclosed above can further comprise, detecting in steps (i) and (iii), the level of one or more proteins regulated by STAT3, such Asp53 (Uniprot Accession No. P04637-1), Fas (Uniprot Accession No. P25445), Hsp70 (Uniprot Accession No. P0DMV8.), Cyclin-D1 (Uniprot Accession No. P24385), IL-10 (Uniprot Accession No. P22301.1), etc. See, e.g., Carpenter and Lo, Cancers 2014, 6, 897-925.

In certain embodiments, anti-tumor efficacy is determined by assaying cytokine levels, e.g., IL-2, IL-7, IL-8, IL-10, IFN-γ, GM-CSF, TNF-α, IL-6, IL-4, IL-5, and IL-13, in plasma samples collected from a subject after administering to said subject a therapeutically effective amount of a modified virus of the present disclosure, such as an oncolytic vaccinia virus as described herein or a pharmaceutical composition comprising the same.

Further provided herein is a method of monitoring the pharmacokinetics following administration of a therapeutically effective amount of modified viruses according to the present disclosure, such as oncolytic vaccinia virus or a pharmaceutical composition containing the vaccinia virus, as described herein. An exemplary method for monitoring the pharmacokinetics can comprise the following steps: (i) administering to the subject a therapeutically effective amount of an oncolytic vaccinia virus or a pharmaceutical composition comprising the same, alone or in combination with a further therapy; (ii) collecting biological samples from the subject at one or more time points selected from about 15 minutes, about 30 minutes, about 45 mins, about 60 mins, about 75 mins, about 90 mins, about 120 mins, about 180 mins, and about 240 mins following the administration in step (ii) and (iii) detecting the quantity of the viral genome in the biological samples collected at the above mentioned time points. In certain embodiments, viral genome copies/mL can be highest in the sample collected at the 15 mins time point and further the sample collected at the 240 mins time point may not contain a detectable quantity of the viral genome. Therefore, in certain embodiments, a viral peak can be observed at about 15 mins following administration and majority of the viruses can be cleared from the subject's system after about 240 mins (or 4 hours). In certain embodiments, a first viral peak can be observed after about 15 mins following administration and a second viral peak can be observed in the biological samples collected in the subsequent time points, e.g., at about 30 mins, about 45 mins, about 60 mins, or about 90 mins. The biological sample can be, in certain embodiments, blood, and the quantity of viral genome/mL can be determined by quantitative PCR or other appropriate techniques. In certain embodiments, a first viral peak can be observed after about 15 mins following administration and a second viral peak can be observed after about 3 hours to about 72 hours following administration of a modified virus of the present disclosure, such as an oncolytic vaccinia virus as described herein.

Delivery of Modified Viruses

In certain embodiments, amount of a modified virus of this disclosure, such as an oncolytic vaccinia virus, administered to a subject can be between about $10^3$ and $10^{12}$ infectious viral particles or plaque forming units (PFU), or between about $10^5$ and $10^{10}$ PFU, or between about $10^5$ and $10^8$ PFU, or between about $10^8$ and $10^{10}$ PFU. See also Thorne and Kim, 2009, Nat Rev Cancer 9: 64-71. In certain embodiments, the amount of a modified virus of this disclosure, such as an oncolytic vaccinia virus administered to a subject can be between about $10^3$ and $10^{12}$ viral particles or PFU, or between about $10^5$ and $10^{10}$ PFU, or between about $10^5$ and $10^8$ PFU, or between about $10^8$ and $10^{10}$ PFU. In certain embodiments, a modified virus of this disclosure, such as an oncolytic vaccinia virus, can be administered at a dose that can comprise about $10^3$ PFU/dose to about $10^4$ PFU/dose, about $10^4$ PFU/dose to about $10^5$ PFU/dose, about $10^5$ PFU/dose to about $10^6$ PFU/dose, about $10^7$ PFU/dose to about $10^8$ PFU/dose, about $10^9$ PFU/dose to about $10^{10}$ PFU/dose, about $10^{10}$ PFU/dose to about $10^{11}$ PFU/dose, about $10^{11}$ PFU/dose to about $10^{12}$ PFU/dose, about $10^{12}$ PFU/dose to about $10^{13}$ PFU/dose, about $10^{13}$ PFU/dose to about $10^{14}$ PFU/dose, or about $10^{14}$ PFU/dose to about $10^{15}$ PFU/dose. In certain embodiments, a modified virus of this disclosure, such as an oncolytic vaccinia virus, can be administered at a dose that can comprise about $10^3$ viral particles/dose to about $10^4$ viral particles/dose, about $10^4$ viral particles/dose to about $10^5$ viral particles/dose, about $10^5$ viral particles/dose to about $10^6$ viral particles/dose, about $10^7$ viral particles/dose to about $10^8$ viral particles/dose, about $10^9$ viral particles/dose to about $10^{10}$ viral particles/dose, about $10^{10}$ viral particles/dose to about $10^{11}$ viral particles/dose, about $10^{11}$ viral particles/dose to about $10^{12}$ viral particles/dose, about $10^{12}$ viral particles/dose to about $10^{13}$ viral particles/dose, about $10^{13}$ viral particles/dose to about $10^{14}$ viral particles/dose, or about $10^{14}$ viral particles/dose to about $10^{15}$ viral particles/dose.

In certain embodiments, a modified virus of this disclosure can be administered at a dose that can comprise about $10^3$ PFU/kg to about $10^4$ PFU/kg, about $10^4$ PFU/kg to about $10^5$ PFU/kg, about $10^5$ PFU/kg to about $10^6$ PFU/kg, about $10^7$ PFU/kg to about $10^8$ PFU/kg, about 9 PFU/kg to about $10^{10}$ PFU/kg, about $10^{10}$ PFU/kg to about $10^{11}$ PFU/kg, about $10^{11}$ PFU/kg to about $10^{12}$ PFU/kg, about $10^{12}$ PFU/kg to about $10^{13}$ PFU/kg, about $10^{13}$ PFU/kg to about $10^{14}$ PFU/kg, or about $10^{14}$ PFU/kg to about $10^{15}$ PFU/kg. In certain embodiments, a modified virus of this disclosure can be administered at a dose that can comprise about $10^3$ viral particles/kg to about $10^4$ viral particles/kg, about $10^4$ viral particles/kg to about $10^5$ viral particles/kg, about $10^5$ viral particles/kg to about $10^6$ viral particles/kg, about $10^7$ viral particles/kg to about $10^8$ viral particles/kg, about $10^9$ viral particles/kg to about $10^{10}$ viral particles/kg, about $10^{10}$ viral particles/kg to about $10^{11}$ viral particles/kg, about $10^{11}$ viral particles/kg to about $10^{12}$ viral particles/kg, about $10^{12}$ viral particles/kg to about $10^{13}$ viral particles/kg, about $10^{13}$ viral particles/kg to about $10^{14}$ viral particles/kg, or about $10^{14}$ viral particles/kg to about $10^{15}$ viral particles/kg.

A liquid dosage form of an oncolytic vaccinia virus as described herein can comprise, in certain embodiments, a viral dose of about $10^3$ PFU/mL to about $10^4$ PFU/mL, about $10^4$ PFU/mL to about $10^5$ PFU/mL, about $10^5$ PFU/mL to about $10^6$ PFU/mL, about $10^7$ PFU/mL to about $10^8$ PFU/mL, about $10^9$ PFU/mL to about $10^{10}$ PFU/mL, about $10^{10}$ PFU/mL to about $10^{11}$ PFU/mL, about $10^{11}$ PFU/mL to about $10^{12}$ PFU/mL, about $10^{12}$ PFU/mL to about $10^{13}$ PFU/mL, about $10^{13}$ PFU/mL to about $10^{14}$ PFU/mL, or about $10^{14}$ PFU/mL to about $10^{15}$ PFU/mL. In certain embodiments, where the modified virus is administered by an injection, the dosage can comprise about $10^3$ viral particles per injection, $10^4$ viral particles per injection, $10^5$ viral particles per injection, $10^6$ viral particles per injection, $10^7$ viral particles per injection, $10^8$ viral particles per injection, $10^9$ viral particles per injection, $10^{10}$ viral particles per injection, $10^{11}$ viral particles per injection, $10^{12}$ viral particles per injection, $2 \times 10^{12}$ viral particles per injection, $10^{13}$ viral particles per injection, $10^{14}$ viral particles per injection, or $10^{15}$ viral particles per injection. In further instances, where the modified virus is administered by an injection, the dosage can comprise about $10^3$ infectious viral particles per injection, $10^4$ infectious viral particles per injection, $10^5$ infectious viral particles per injection, $10^6$ infectious viral particles per injection, $10^7$ infectious viral particles per injection, $10^8$ infectious viral particles per injection, $10^9$ infectious viral particles per injection, $10^{10}$ infectious viral particles per injection, $10^{11}$ infectious viral particles per injection, $10^{12}$ infectious viral particles per injection, $2 \times 10^{12}$ infectious viral particles per injection, $10^{13}$ infectious viral particles per injection, $10^{14}$ infectious viral particles per injection, or $10^{15}$ infectious viral particles per injection. In additional embodiments, a modified virus of this disclosure can be administered at a dose that can be about $10^3$ Tissue Culture Inhibitor Dose 50% (TCID$_{50}$)/kg, $10^4$ TCID$_{50}$/kg, $10^4$ TCID$_{50}$/kg, $10^4$ TCID$_{50}$/kg, $10^4$ TCID$_{50}$/kg, $10^4$ TCID$_{50}$/kg, $10^4$ TCID$_{50}$/kg, $10^4$ TCID$_{50}$/kg, $10^4$ TCID$_{50}$/kg, $10^4$ TCID$_{50}$/kg, $10^4$ TCID$_{50}$/kg, $10^4$ TCID$_{50}$/kg, $10^4$ TCID$_{50}$/kg, $10^4$ TCID$_{50}$/kg, $3 \times 10^8$ TCID$_{50}$/kg, $4 \times 10^8$ TCID$_{50}$/kg, $5 \times 10^8$ TCID$_{50}$/kg, $3 \times 10^9$ TCID$_{50}$/kg, $4 \times 10^9$ TCID$_{50}$/kg, $5 \times 10^9$ TCID$_{50}$/kg, $3 \times 10^{10}$ TCID$_{50}$/kg, $4 \times 10^{10}$ TCID$_{50}$/kg, or $4 \times 10^{10}$ TCID$_{50}$/kg. Note that herein $10^x$ is alternatively expressed as 1 eX. In certain embodiments, the modified virus can be administered in one or more doses. In certain embodiments, the virus can be administered in an amount sufficient to induce oncolysis in at least about 20% of cells in a tumor, in at least about 30% of cells in a tumor, in at least about 40% of cells in a tumor, in at least about 50% of cells in a tumor, in at least about 60% of cells in a tumor, in at least about 70% of cells in a tumor, in at least about 80% of cells in a tumor, or in at least about 90% of cells in a tumor. In certain embodiments, a single dose of virus can refer to the amount administered to a subject or a tumor over a 1, 2, 5, 10, 15, 20 or 24 hour period. In certain embodiments, the dose can be spread over time or by separate injection. In certain embodiments, multiple doses (e.g., 2, 3, 4, 5, 6 or more doses) of the vaccinia virus can be administered to the subject, for example, where a second treatment can occur within 1, 2, 3, 4, 5, 6, 7 days or weeks of a first treatment. In certain embodiments, multiple doses of the modified virus can be administered to the subject over a period of 1, 2, 3, 4, 5, 6, 7 or more days or weeks. In certain embodiments, the oncolytic vaccinia virus or the pharmaceutical composition as described herein can be administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. The frequency of administration of the oncolytic vaccinia virus or the pharmaceutical composition as described herein can be, in certain instances, once daily, twice daily, once every week, once every three weeks, once every four weeks (or once a month), once every 8 weeks (or once every 2 months), once every 12 weeks (or once every 3 months), or once every 24 weeks (once every 6 months). In certain embodiments of the methods disclosed herein, the oncolytic vaccinia virus or the pharmaceutical composition can be administered, independently, in an initial dose for a first period of time, an intermediate dose for a second period of time, and a high dose for a third period of time. In certain embodiments, the initial dose is lower than the intermediate dose and the intermediate dose is lower than the high dose. In certain embodiments, the first, second, and third periods of time are, independently, about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer.

In certain embodiments, the subject can be put on a reduced carbohydrate diet, e.g., a ketogenic diet prior to, concurrent with, and following administration of the modified viruses, such as the oncolytic vaccinia viruses or the pharmaceutical composition comprising the same, as described herein, according to any of the methods of treatment described herein. In certain embodiments, the subject is put on a diet that can comprise consuming less than 500 grams of carbohydrates per day, less than 450 grams of carbohydrates per day, less than 450 grams of carbohydrates per day, less than 400 grams of carbohydrates per day, less than 350 grams of carbohydrates per day, less than 300 grams of carbohydrates per day, less than 250 grams of carbohydrates per day, less than 200 grams of carbohydrates per day, less than 150 grams of carbohydrates per day, less than 100 grams of carbohydrates per day, less than 90 grams of carbohydrates per day, less than 80 grams of carbohydrates per day, less than 70 grams of carbohydrates per day, less than 60 grams of carbohydrates per day, less than 50 grams of carbohydrates per day, less than 40 grams of carbohydrates per day, less than 30 grams of carbohydrates per day, less than 20 grams of carbohydrates per day, less or than 10 grams of carbohydrates per day.

An exemplary method for the delivery of a modified virus of the present disclosure, such as an oncolytic vaccinia virus as described herein or a pharmaceutical composition comprising the same, to cancer or tumor cells can be via intratumoral injection. However, alternate methods of administration can also be used, e.g., intravenous, via infusion, parenteral, intravenous, intradermal, intramuscular, transdermal, rectal, intraurethral, intravaginal, intranasal, intrathecal, or intraperitoneal. The routes of administration can vary with the location and nature of the tumor. In certain embodiments, the route of administration can be intradental, transdermal, parenteral, intravenous, intramuscular, intranasal, subcutaneous, regional (e.g., in the proximity of a tumor, particularly with the vasculature or adjacent vasculature of a tumor), percutaneous, intrathecal, intratracheal, intraperitoneal, intraarterial, intravesical, intratumoral, inhalation, perfusion, by lavage or orally. In certain embodiments, the modified virus can be administered to the patient from a source implanted in the patient. In certain embodiments, administration of the modified virus can occur by continuous infusion over a selected period of time. In certain embodiments, an oncolytic vaccinia virus as described herein, or a pharmaceutical composition containing the same can be administered at a therapeutically effective dose by infusion over a period of about 15 mins, about 30 mins, about 45 mins, about 50 mins, about 55 mins, about 60 minutes, about 75 mins, about 90 mins, about 100 mins, or about 120 mins or longer. The oncolytic vaccinia virus or the pharmaceutical composition of the present disclosure can be administered as a liquid dosage, wherein the total volume of administration is about 1 ml to about 5 ml, about 5 ml to 10 ml, about 15 ml to about 20 ml, about 25 ml to about 30 ml, about 30 ml to about 50 ml, about 50 ml to about 100 ml, about 100 ml to 150 ml, about 150 ml to about 200 ml, about 200 ml to about 250 ml, about 250 ml to about 300 ml, about 300 ml to about 350 ml, about 350 ml to about 400 ml, about 400 ml to about 450 ml, about 450 ml to 500 ml, about 500 ml to 750 ml or about 750 ml to 1000 ml.

Pharmaceutical Compositions

The present disclosure further provides pharmaceutical compositions comprising the modified viruses disclosed herein. In certain embodiments, the pharmaceutical compositions containing a modified virus, such as an oncolytic vaccinia virus, as described herein, can be prepared as solutions, dispersions in glycerol, liquid polyethylene glycols, and any combinations thereof in oils, in solid dosage forms, as inhalable dosage forms, as intranasal dosage forms, as liposomal formulations, dosage forms comprising nanoparticles, dosage forms comprising microparticles, polymeric dosage forms, or any combinations thereof. Pharmaceutical compositions are formulated relative to the particular administration route. For example, and not by way of limitation, pharmaceutical compositions that can be administered parenterally, intravenously, intradermally, intramuscularly, transdermally or intraperitoneally are described in U.S. Pat. Nos. 5,543,158, 5,641,515 and 5,399,363, the contents of which are incorporated by reference herein in their entireties.

In certain embodiments, a pharmaceutical composition as described herein can comprise an excipient. An excipient can be an excipient described in the Handbook of Pharmaceutical Excipients, American Pharmaceutical Association (1986). Non-limiting examples of suitable excipients can include a buffering agent, a preservative, a stabilizer, a binder, a compaction agent, a lubricant, a chelator, a dispersion enhancer, a disintegration agent, a flavoring agent, a sweetener, a coloring agent.

In certain embodiments, an excipient can be a buffering agent. Non-limiting examples of suitable buffering agents can include sodium citrate, magnesium carbonate, magnesium bicarbonate, calcium carbonate, and calcium bicarbonate. As a buffering agent, sodium bicarbonate, potassium bicarbonate, magnesium hydroxide, magnesium lactate, magnesium glucomate, aluminium hydroxide, sodium citrate, sodium tartrate, sodium acetate, sodium carbonate, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide and other calcium salts or combinations thereof can be used in a pharmaceutical formulation.

In certain embodiments, an excipient can comprise a preservative. Non-limiting examples of suitable preservatives can include antioxidants, such as alpha-tocopherol and ascorbate, and antimicrobials, such as parabens, chlorobutanol, and phenol. Antioxidants can further include but not limited to EDTA, citric acid, ascorbic acid, butylated hydroxytoluene (BHT), butylated hydroxy anisole (BHA), sodium sulfite, p-amino benzoic acid, glutathione, propyl gallate, cysteine, methionine, ethanol and N-acetyl cysteine. In certain embodiments a preservatives can include validamycin A, TL-3, sodium ortho vanadate, sodium fluoride, N-a-tosyl-Phe-chloromethylketone, N-a-tosyl-Lys-chloromethylketone, aprotinin, plaenylmethylsulfonyl fluoride, diisopropylfluorophosphate, kinase inhibitor, phosphatase inhibitor, caspase inhibitor, granzyme inhibitor, cell adhesion inhibitor, cell division inhibitor, cell cycle inhibitor, lipid signaling inhibitor, protease inhibitor, reducing agent, alkylating agent, antimicrobial agent, oxidase inhibitor, or other inhibitor.

In certain embodiments, a pharmaceutical composition as described herein can comprise a binder as an excipient. Non-limiting examples of suitable binders can include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof. The binders that can be used in a pharmaceutical formulation can be selected from starches such as potato starch, corn starch, wheat starch; sugars such as sucrose, glucose, dextrose, lactose, maltodextrin; natural and synthetic gums; gelatine; cellulose derivatives such as microcrystalline cellulose, hydroxypropyl cellulose, hydroxyethyl cellulose, hydroxypropyl methyl cellulose, carboxymethyl cellulose, methyl cellulose, ethyl cellulose; polyvinylpyrrolidone (povidone); polyethylene glycol (PEG); waxes; calcium carbonate; calcium phosphate; alcohols such as sorbitol, xylitol, mannitol and water or a combination thereof.

In certain embodiments, a pharmaceutical composition as described herein can comprise a lubricant as an excipient. Non-limiting examples of suitable lubricants can include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil. The lubricants that can be used in a pharmaceutical formulation can be selected from metallic stearates (such as magnesium stearate, calcium stearate, aluminium stearate), fatty acid esters (such as sodium stearyl fumarate), fatty acids (such as stearic acid), fatty alcohols, glyceryl behenate, mineral oil, paraffins, hydrogenated vegetable oils, leucine, polyethylene glycols (PEG), metallic lauryl sulphates (such as sodium lauryl sulphate, magnesium lauryl sulphate), sodium chloride, sodium benzoate, sodium acetate and talc or a combination thereof.

In certain embodiments, a pharmaceutical formulation can comprise a dispersion enhancer as an excipient. Non-limiting examples of suitable dispersants can include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In certain embodiments, a pharmaceutical composition as described herein can comprise a disintegrant as an excipient.

In certain embodiments a disintegrant can be a non-effervescent disintegrant. Non-limiting examples of suitable non-effervescent disintegrants can include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. In certain embodiments a disintegrant can be an effervescent disintegrant. Non-limiting examples of suitable effervescent disintegrants can include sodium bicarbonate in combination with citric acid, and sodium bicarbonate in combination with tartaric acid.

In certain embodiments an excipient can comprise a flavoring agent. Flavoring agents incorporated into an outer layer can be chosen from synthetic flavor oils and flavoring aromatics; natural oils; extracts from plants, leaves, flowers, and fruits; and combinations thereof. In certain embodiments a flavoring agent can be selected from the group consisting of cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In certain embodiments, an excipient can comprise a sweetener. Non-limiting examples of suitable sweeteners can include glucose (corn syrup), dextrose, invert sugar, fructose, and mixtures thereof (when not used as a carrier); saccharin and its various salts such as a sodium salt; dipeptide sweeteners such as aspartame; dihydrochalcone compounds, glycyrrhizin; *Stevia rebaudiana* (Stevioside); chloro derivatives of sucrose such as sucralose; and sugar alcohols such as sorbitol, mannitol, sylitol, and the like.

In certain embodiments, a pharmaceutical composition as described herein can comprise a coloring agent. Non-limiting examples of suitable color agents can include food, drug and cosmetic colors (FD&C), drug and cosmetic colors (D&C), and external drug and cosmetic colors (Ext. D&C). A coloring agents can be used as dyes or their corresponding lakes.

In certain embodiments, a pharmaceutical composition as described herein can comprise a chelator. In some cases, a chelator can be a fungicidal chelator. Examples can include, but are not limited to: ethylenediamine-N,N,N',N'-tetraacetic acid (EDTA); a disodium, trisodium, tetrasodium, dipotassium, tripotassium, dilithium and diammonium salt of EDTA; a barium, calcium, cobalt, copper, dysprosium, europium, iron, indium, lanthanum, magnesium, manganese, nickel, samarium, strontium, or zinc chelate of EDTA; trans-1,2-diaminocyclohexane-N,N,N',N'-tetraaceticacid monohydrate; N,N-bis(2-hydroxyethyl)glycine; 1,3-diamino-2-hydroxypropane-N,N,N',N'-tetraacetic acid; 1,3-diaminopropane-N,N,N',N'-tetraacetic acid; ethylenediamine-N,N'-diacetic acid; ethylenediamine-N,N'-dipropionic acid dihydrochloride; ethylenediamine-N,N'-bis (methylenephosphonic acid) hemihydrate; N-(2-hydroxyethyl)ethylenediamine-N,N',N'-triacetic acid; ethylenediamine-N,N,N',N'-tetrakis(methylenephosponic acid); O,O'-bis(2-aminoethyl)ethyleneglycol-N,N,N',N'-tetraacetic acid; N,N-bis(2-hydroxybenzyl)ethylenediamine-N,N-diacetic acid; 1,6-hexamethylenediamine-N,N,N',N'-tetraacetic acid; N-(2-hydroxyethyl)iminodiacetic acid; iminodiacetic acid; 1,2-diaminopropane-N,N,N',N'-tetraacetic acid; nitrilotriacetic acid; nitrilotripropionic acid; the trisodium salt of nitrilotris(methylenephosphoric acid); 7,19,30-trioxa-1,4,10,13,16,22,27,33-octaazabicyclo[11,11,11] pentatriacontane hexahydrobromide; or triethylenetetramine-N,N,N',N'',N''',N'''-hexaacetic acid.

Also contemplated are combination products that include one or more modified viruses disclosed herein and one or more other antimicrobial or antifungal agents, for example, polyenes such as amphotericin B, amphotericin B lipid complex (ABCD), liposomal amphotericin B (L-AMB), and liposomal nystatin, azoles and triazoles such as voriconazole, fluconazole, ketoconazole, itraconazole, pozaconazole and the like; glucan synthase inhibitors such as caspofungin, micafungin (FK463), and V-echinocandin (LY303366); griseofulvin; allylamines such as terbinafine; flucytosine or other antifungal agents, including those described herein. In addition, it is contemplated that a peptide can be combined with topical antifungal agents such as ciclopirox olamine, haloprogin, tolnaftate, undecylenate, topical nysatin, amorolfine, butenafine, naftifine, terbinafine, and other topical agents. In certain embodiments, a pharmaceutical composition can comprise an additional agent. In some cases, an additional agent can be present in a therapeutically effective amount in a pharmaceutical composition.

Under ordinary conditions of storage and use, the pharmaceutical compositions as described herein can comprise a preservative to prevent the growth of microorganisms. In certain examples, the pharmaceutical compositions as described herein may not comprise a preservative. The pharmaceutical forms suitable for injectable use can include sterile aqueous solutions or dispersions and sterile powders for the extemporaneous preparation of sterile injectable solutions or dispersions. The pharmaceutical compositions can comprise a carrier which is a solvent or a dispersion medium containing, for example, water, ethanol, polyol (e.g., glycerol, propylene glycol, and liquid polyethylene glycol, and the like), and/or vegetable oils, or any combinations thereof. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the liquid dosage form can be suitably buffered if necessary and the liquid diluent rendered isotonic with sufficient saline or glucose. The liquid dosage forms are especially suitable for intravenous, intramuscular, subcutaneous, intratumoral, and intraperitoneal administration. In this connection, sterile aqueous media that can be employed will be known to those of skill in the art in light of the present disclosure. For example, one dosage may be dissolved in 1 mL to 20 mL of isotonic NaCl solution and either added to 100 mL to 1000 mL of a fluid, e.g., sodium-bicarbonate buffered saline, or injected at the proposed site of infusion.

In certain embodiments, sterile injectable solutions can be prepared by incorporating a modified virus according to the present disclosure, such as oncolytic vaccinia viruses as described herein or a pharmaceutical composition containing the same, in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, the pharmaceutical compositions can be administered in a manner compatible with the dosage formulation and in such amount as is therapeutically effective.

In certain embodiments, a pharmaceutical composition of this disclosure can comprise an effective amount of a modified virus, disclosed herein, combined with a pharmaceutically acceptable carrier. "Pharmaceutically acceptable," as used herein, includes any carrier which does not interfere with the effectiveness of the biological activity of the active ingredients and/or that is not toxic to the patient to whom it is administered. Non-limiting examples of suitable pharmaceutical carriers include phosphate buffered saline solutions, water, emulsions, such as oil/water emulsions, various types of wetting agents and sterile solutions. Additional non-limiting examples of pharmaceutically compatible carriers can include gels, bioadsorbable matrix materials, implantation elements containing the modified virus or any other suitable vehicle, delivery or dispensing means or material. Such carriers can be formulated by conventional methods and can be administered to the subject at an effective amount.

Methods of Production

The modified viruses of this disclosure can be produced by methods known to one of skill in the art. In certain embodiments, the modified virus can be propagated in suitable host cells, isolated from host cells and stored in conditions that promote stability and integrity of the virus, such that loss of infectivity over time is minimized. Non-limiting examples of host cells include HeLa cells, HEK293 cells and Vero cells. In certain exemplary methods, the modified viruses are propagated in host cells using cell stacks, roller bottles, or perfusion bioreactors. In certain embodiments, downstream methods for purification of the modified viruses can comprise filtration (e.g., depth filtration, tangential flow filtration, or a combination thereof), ultracentrifugation, or chromatographic capture. The modified virus can be stored, e.g., by freezing or drying, such as by lyophilization. In certain embodiments, prior to administration, the stored modified virus can be reconstituted (if dried for storage) and diluted in a pharmaceutically acceptable carrier for administration.

Combination Therapies

In certain embodiments, the methods of this disclosure comprise administering a modified virus as disclosed herein or a pharmaceutical composition containing the same, followed by, and preceded by or in combination with one or more further therapy. Examples of the further therapy can include, but are not limited to, chemotherapy, radiation, oncolytic viral therapy with an additional virus, treatment with immunomodulatory proteins, a STAT3 inhibitor, an anti-cancer agent, or any combinations thereof. The further therapy can be administered concurrently or sequentially with respect to administration of the modified virus, such as oncolytic vaccinia virus. In certain embodiments, the methods of this disclosure can comprise administering a modified virus as disclosed herein, followed by, preceded by, or in combination with one or more anti-cancer agents or cancer therapies. Anti-cancer agents can include, but are not limited to, chemotherapeutic agents, radiotherapeutic agents, cytokines, immune checkpoint inhibitors, anti-angiogenic agents, apoptosis-inducing agents, anti-cancer antibodies and/or anti-cyclin-dependent kinase agents. In certain embodiments, the cancer therapies can include chemotherapy, biological therapy, radiotherapy, immunotherapy, hormone therapy, anti-vascular therapy, cryotherapy, toxin therapy and/or surgery or combinations thereof. In certain embodiments, the methods of this disclosure can include administering a modified virus, disclosed herein, followed by, preceded by or in combination with one or more STAT3 inhibitors. Non-limiting examples of STAT3 inhibitors include compounds, molecules, chemicals, polypeptides and proteins that inhibit and/or reduce the expression and/or activity of STAT3. In certain embodiments, the STAT3 inhibitor can include peptide aptamers designed to block STAT3 dimerization or DNA binding; the mammalian proteins SOCS3 and GRIM-19; small molecules such as, but not limited to, S3I-201, S31-2001, STA-21, 1S3-295, withacnistin, galiellalactone, niclosamide, stattic and cucurbitacins (e.g., cucurbitacin I); or combinations thereof. Additional non-limiting examples of STAT3 inhibitors are disclosed in Yue et al., Expert Opin. Investig. Drugs 18(1): 45-56 (2009), Siveen et al., Biochimica et Biophysica Acta 1845:136-154 (2014), Bu et al., Gene 512(2):198-205 (2013) and Furtek et al. ACS Chem. Biol. 11(2):308-318 (2016), the contents of which are incorporated by reference herein in their entireties. In certain embodiments, the STAT3 inhibitor can be an antibody or antibody fragment that can partially or completely block STAT3 signaling and/or activity. Further non-limiting examples of STAT3 inhibitors can include ribozyines, antisense oligonucleotides, decoy oligonucleotides blocking the STAT3 DNA-binding site by mimicking STAT3 response elements, shRNA molecules and siRNA molecules that specifically inhibit and/or reduce the expression or activity of STAT3. One non-limiting example of a STAT3 inhibitor can comprise an antisense, shRNA or siRNA nucleic acid sequence homologous to at least a portion of a STAT3 nucleic acid sequence, wherein the homology of the portion relative to the STAT3 sequence can at least be about 75 or at least be about 80 or at least be about 85 or at least be about 90 or at least be about 95 or at least be about 98 percent, where percent homology can be determined by, for example, BLAST or FASTA software. In certain embodiments, the complementary portion may constitute at least 10 nucleotides or at least 15 nucleotides or at least 20 nucleotides or at least 25 nucleotides or at least 30 nucleotides and the antisense nucleic acid, shRNA or siRNA molecules may be up to 15 or up to 20 or up to 25 or up to 30 or up to 35 or up to 40 or up to 45 or up to 50 or up to 75 or up to 100 nucleotides in length. Antisense, shRNA or siRNA molecules may comprise DNA or atypical or non-naturally occurring residues, for example, but not limited to, phosphorothioate residues. The RNA molecules can be expressed from a vector or produced chemically or synthetically. Methods for selecting an appropriate dsRNA or dsRNA-encoding vector are well known in the art for genes whose sequence is known (e.g., see Tuschl, T. et al. (1999); Elbashir, S. M. et al. (2001); Hannon, G. J. (2002); McManus, M T. et al. (2002); Brummelkamp, T R. et al. (2002); U.S. Pat. Nos. 6,573,099 and 6,506,559; and PCT Patent Application Nos. WO 2001/036646, WO 1999/032619 and WO 2001/068836).

In certain embodiments, treatment using a modified virus can be used alone or in combination with one or immunomodulatory agents. An immunomodulatory agent can include any compound, molecule or substance capable of suppressing antiviral immunity associated with a tumor or cancer. In certain embodiments, the immunomodulatory agent can be capable of suppressing innate immunity or adaptive immunity to the modified virus. Non-limiting examples of immunomodulatory agents include anti-CD33 antibody or variable region thereof, an anti-CD11b antibody or variable region thereof, a COX2 inhibitor, e.g., celecoxib, cytokines, such as IL-12, GM-CSF, IL-2, IFN3 and 1FNy, and chemokines, such as MIP-1, MCP-1 and IL-8. In certain embodiments, the immunomodulatory agent includes immune checkpoint inhibitors such as, but not limited to, anti-CTLA4, anti-PD-1, anti-PDL1 and TLR agonists (e.g., Poly 1:C).

In certain examples, where the further therapy is radiation exemplary doses can be 5,000 Rads (50 Gy) to 100,000 Rads (1000 Gy), or 50,000 Rads (500 Gy), or other appropriate doses within the recited ranges. Alternatively, the radiation dose can be about 30 to 60 Gy, about 40 to about 50 Gy, about 40 to 48 Gy, or about 44 Gy, or other appropriate doses within the recited ranges, with the dose determined, example, by means of a dosimetry study as described above. "Gy" as used herein can refer to a unit for a specific absorbed dose of radiation equal to 100 Rads. Gy is the abbreviation for "Gray."

In certain examples, where the further therapy is chemotherapy, exemplary chemotherapeutic agents can include without limitation alkylating agents (e.g., nitrogen mustard derivatives, ethylenimines, alkylsulfonates, hydrazines and triazines, nitrosureas, and metal salts), plant alkaloids (e.g., vinca alkaloids, taxanes, podophyllotoxins, and camptothecan analogs), antitumor antibiotics (e.g., anthracyclines, chromomycins, and the like), antimetabolites (e.g., folic acid antagonists, pyrimidine antagonists, purine antagonists, and adenosine deaminase inhibitors), topoisomerase I inhibitors, topoisomerase II inhibitors, and miscellaneous antineoplastics (e.g., ribonucleotide reductase inhibitors, adrenocortical steroid inhibitors, enzymes, antimicrotubule agents, and retinoids). Exemplary chemotherapeutic agents can include, without limitation, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNUO), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, gemcitabine (difluorodeoxycitidine), hydroxyurea (Hydrea®), idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxo10), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®), ibrutinib, idelalisib, and brentuximab vedotin.

Exemplary alkylating agents can include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), chlorambucil (Leukeran®), pipobroman (Amedel®, Vercyte®), triethylenemelamine Hemel®, Hexalen®, Hexastat®), triethylenethiophosphoramine, temozolomide (Temodar®), thiotepa (Thioplex®), busulfan (Busilvex®, Myleran®), carmustine (BiCNUO), lomustine (CeeNUO), streptozocin (Zanosar®), and dacarbazine (DTIC-Dome®). Additional exemplary alkylating agents include, without limitation, oxaliplatin (Eloxatin®); temozolomide (Temodar® and Temodal®); dactinomycin (also known as actinomycin-D, Cosmegen®); melphalan (also known as L-PAM, L-sarcolysin, and phenylalanine mustard, Alkeran®); altretamine (also known as hexamethylmelamine (HMM), Hexalen®); carmustine (BiCNUO); bendamustine (Treanda®); busulfan (Busulfex® and Myleran®); carboplatin (Paraplatin®); lomustine (also known as CCNU, CeeNUO); cisplatin (also known as CDDP, Platinol® and Platinol®-AQ); chlorambucil (Leukeran®); cyclophosphamide (Cytoxan® and Neosar®); dacarbazine (also known as DTIC, DIC and imidazole carboxamide, DTIC-Dome®); altretamine (also known as hexamethylmelamine (HMM), Hexalen®); ifosfamide (Ifex®); prednumustine; procarbazine (Matulane®); mechlorethamine (also known as nitrogen mustard, mustine and mechloroethamine hydrochloride, Mustargen®); streptozocin (Zanosar®); thiotepa (also known as thiophosphoamide, TESPA and TSPA, Thioplex®); cyclophosphamide (Endoxan®, Cytoxan®, Neosar®, Procytox®, Revimmune™); and bendamustine HCl (Treanda®).

Exemplary anthracyclines can include, without limitation, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids can include, but are not limited to, vinorelbine tartrate (Navelbine®), vincristine (Oncovin®), and vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors can, but are not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoac etamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-serinamide (ONX-0912).

"In combination with," as used herein, means that the modified virus, such as an oncolytic vaccinia virus as described herein or a pharmaceutical composition comprising the same, and the further therapy, such as a further therapy comprising one or more agents are administered to a subject as part of a treatment regimen or plan. In certain embodiments, being used in combination does not require that the modified virus and the one or more agents are physically combined prior to administration or that they be administered over the same time frame. For example, and not by way of limitation, the modified virus and the one or more agents can be administered concurrently to the subject being treated, or can be administered at the same time or sequentially in any order or at different points in time.

The further therapy can be administered, in various embodiments, in a liquid dosage form, a solid dosage form, a suppository, an inhalable dosage form, an intranasal dosage form, in a liposomal formulation, a dosage form comprising nanoparticles, a dosage form comprising microparticles, a polymeric dosage form, or any combinations thereof. In certain embodiments, the further therapy is administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. The frequency of administration of the further therapy can be, in certain instances, once daily, twice daily, once every week, once every three weeks, once every four weeks (or once a month), once every 8 weeks (or once every 2 months), once every 12 weeks (or once every 3 months), or once every 24 weeks (once every 6 months).

In certain embodiments, a method of treating a subject having a cancer includes administering, to the subject, an effective amount of a modified virus, e.g., vaccinia virus, comprising one or more exogenous nucleic acid(s) that encode a protein that modulates the activity of STAT3. For example, and not by way of limitation, a method of treating a subject having a cancer includes administering, to the subject, an effective amount of a modified virus, e.g., vaccinia virus, comprising one or more exogenous nucleic acid(s) that encode a protein that inhibits, reduces and/or minimizes STAT3 activity. In certain embodiments, the vaccinia virus for use in the discloses methods comprises a exogenous nucleic acid that encodes a PIAS3 protein or fragment thereof, a SOCS3 protein or fragment thereof, a TCPTP protein or fragment thereof and/or a dominant-negative mutant STAT3 protein. In certain embodiments, the methods of this disclosure can further include administering to the subject an effective amount of one or more agents. For example, and not by way of limitation, the agent can be an anti-cancer agent, a STAT3 inhibitor and/or an immunomodulatory agent, as described above.

In certain embodiments, a method of treating a subject having a cancer includes administering, to the subject, an effective amount of a modified virus, e.g., vaccinia virus, expressing one or more nucleic acid(s) that encode a PIAS3 protein comprising an amino acid sequence that is at least about 85%, at least about 90%, at least about 95%, at least about 96%, at least about 97%, at least about 98%, at least about 99% or 100% homologous to an amino acid sequence selected from the group consisting of SEQ ID NOs: 1-7 and 24-27 and conservative substitutions thereof, e.g., SEQ ID NO: 1 and conservative substitutions thereof. For example, and not by way of limitation, an modified virus of the present invention can comprise a nucleic acid that comprises a nucleotide sequence that is at least about 85%, at least about 90%, at least about 95%, at least about 96%, at least about 97%, at least about 98%, at least about 99% or 100% homologous to a nucleic acid sequence selected from the group consisting of SEQ ID NOs: 8-10 and 40-43. In certain embodiments, the PIAS3 protein can be further conjugated to a cell penetrating peptide, as disclosed herein, and the exogenous nucleic acid can further encode a cell penetrating peptide. In certain embodiments, the methods of this disclosure can further include administering to the subject an effective amount of one or more agents. For example, and not by way of limitation, the agent can be an anti-cancer agent, a STAT3 inhibitor and/or an immunomodulatory agent, as described above.

In certain embodiments, a method of treating a subject having a cancer includes administering, to the subject, an effective amount of a modified virus, e.g., vaccinia virus, expressing one or more nucleic acid(s) that encode a SOCS3 protein comprising an amino acid sequence that is at least about 85%, at least about 90%, at least about 95%, at least about 96%, at least about 97%, at least about 98%, at least about 99% or 100% homologous to an amino acid sequence selected from the group consisting of SEQ ID NOs: 28 and 30 and conservative substitutions thereof, e.g., SEQ ID NO: 28 and conservative substitutions thereof. For example, and not by way of limitation, an modified virus of the present invention can comprise a nucleic acid that comprises a nucleotide sequence that is at least about 85%, at least about 90%, at least about 95%, at least about 96%, at least about 97%, at least about 98%, at least about 99% or 100% homologous to a nucleic acid sequence selected from the group consisting of SEQ ID NOs: 29 and 31. In certain embodiments, the SOCS3 protein can be further conjugated to a cell penetrating peptide, as disclosed herein, and the exogenous nucleic acid can further encode a cell penetrating peptide. In certain embodiments, the methods of this disclosure can further include administering to the subject an effective amount of one or more agents. For example, and not by way of limitation, the agent can be an anti-cancer agent, a STAT3 inhibitor and/or an immunomodulatory agent, as described above.

In certain embodiments, a method of treating a subject having a cancer includes administering, to the subject, an effective amount of a modified virus, e.g., vaccinia virus, expressing one or more nucleic acid(s) that encode a TCPTP protein comprising an amino acid sequence that is at least about 85%, at least about 90%, at least about 95%, at least about 96%, at least about 97%, at least about 98%, at least about 99% or 100% homologous to an amino acid sequence selected from the group consisting of SEQ ID NOs: 32 and 34 and conservative substitutions thereof, e.g., SEQ ID NO: 32 and conservative substitutions thereof. For example, and not by way of limitation, an modified virus of the present invention can comprise a nucleic acid that comprises a nucleotide sequence that is at least about 85%, at least about 90%, at least about 95%, at least about 96%, at least about 97%, at least about 98%, at least about 99% or 100% homologous to a nucleic acid sequence selected from the group consisting of SEQ ID NOs: 33 and 35. In certain embodiments, the TCPTP protein can be further conjugated to a cell penetrating peptide, as disclosed herein, and the exogenous nucleic acid can further encode a cell penetrating peptide. In certain embodiments, the methods of this disclosure can further include administering to the subject an effective amount of one or more agents. For example, and not by way of limitation, the agent can be an anti-cancer agent, a STAT3 inhibitor and/or an immunomodulatory agent, as described above.

In certain embodiments, a method of treating a subject having a cancer includes administering, to the subject, an effective amount of a modified virus, e.g., vaccinia virus, expressing one or more nucleic acid(s) that encode a dominant-negative mutant STAT3 protein comprising an amino acid sequence that is at least about 85%, at least about 90%, at least about 95%, at least about 96%, at least about 97%, at least about 98%, at least about 99% or 100% homologous to an amino acid sequence selected from the group consisting of SEQ ID NOs: 36 and 38 and conservative substitutions thereof, e.g., SEQ ID NO: 36 and conservative substitutions thereof. For example, and not by way of limitation, an modified virus of the present invention can comprise a nucleic acid that comprises a nucleotide sequence that is at least about 85%, at least about 90%, at least about 95%, at least about 96%, at least about 97%, at least about 98%, at least about 99% or 100% homologous to a nucleic acid sequence selected from the group consisting of SEQ ID NOs: 37 and 39. In certain embodiments, the dominant-negative mutant STAT3 protein can be further conjugated to a cell penetrating peptide, as disclosed herein, and the exogenous nucleic acid can further encode a cell penetrating peptide.

Kits

The present disclosure further provides kits that comprise one or more of the disclosed oncolytic viruses described herein. In embodiments, this disclosure provides for a kit for administering a modified virus as described herein. In certain embodiments, a kit of this disclosure can include a modified virus or a pharmaceutical composition comprising a modified virus as described above. In certain embodiments, a kit of this disclosure can further include one or more components such as instructions for use, devices and additional reagents, and components, such as tubes, containers and syringes for performing the methods disclosed above. In certain embodiments, a kit of this disclosure can further include one or more agents, e.g., anti-cancer agents, STAT3 inhibitors and/or immunomodulatory agents, that can be administered in combination with a modified virus.

In certain embodiments, a kit of this disclosure can comprise one or more containers containing a modified virus, disclosed herein. For example, and not by way of limitation, a kit of this disclosure can comprise one or more containers that contain a modified vaccinia virus expressing one or more of a PIAS3 protein or a fragment thereof, a SOCS3 protein or a fragment thereof, a TCPTP protein or a fragment thereof, a dominant-negative mutant STAT3 protein or fragment thereof or any combinations thereof. In certain embodiments, the protein that modulates STAT3 activity can be conjugated to a cell penetrating peptide.

In certain embodiments, a kit of this disclosure can include an effective amount of a modified vaccinia virus comprising one or more nucleic acids that encode a PIAS3 protein that can comprise an amino acid sequence that can be at least about 85%, at least about 90%, at least about 95%, at least about 96%, at least about 97%, at least about 98%, at least about 99% or 100% homologous to an amino acid sequence selected from the group consisting of SEQ ID NOs: 1-7 and 24-27 and conservative substitutions thereof. In certain embodiments, a kit of this disclosure can include a modified vaccinia virus comprising one or more nucleic acids that encode a PIAS3 protein having the amino acid sequence of SEQ ID NO: 1 or a fragment thereof, e.g., amino acids of 133-316, 129-316, 126-176, 132-177 or 400-528 of SEQ ID NO: 1.

In certain embodiments, a kit of this disclosure can include an effective amount of a modified vaccinia virus comprising one or more nucleic acids that can encode a SOCS3 protein comprising an amino acid sequence that can be at least about 85%, at least about 90%, at least about 95%, at least about 96%, at least about 97%, at least about 98%, at least about 99% or 100% homologous to an amino acid sequence selected from the group consisting of SEQ ID NOs: 28 and 30 and conservative substitutions thereof. In certain embodiments, a kit of this disclosure can include a modified vaccinia virus comprising one or more nucleic acids that encode a SOCS3 protein having the amino acid sequence of SEQ ID NO: 28 or a fragment thereof.

In certain embodiments, a kit of this disclosure can include an effective amount of a modified vaccinia virus comprising one or more nucleic acids that encode a TCPTP protein, e.g., a TCPTP isoform 2 protein, comprising an amino acid sequence that can be at least about 85%, at least about 90%, at least about 95%, at least about 96%, at least about 97%, at least about 98%, at least about 99% or 100% homologous to an amino acid sequence selected from the group consisting of SEQ ID NOs: 32 and 34 and conservative substitutions thereof. In certain embodiments, a kit of this disclosure can include a modified vaccinia virus comprising one or more nucleic acids that can encode a TCPTP protein having the amino acid sequence of SEQ ID NO: 32 or a fragment thereof.

In certain embodiments, a kit of this disclosure can include an effective amount of a modified vaccinia virus comprising one or more nucleic acids that can encode a dominant-negative mutant STAT3 protein comprising an amino acid sequence that can be at least about 85%, at least about 90%, at least about 95%, at least about 96%, at least about 97%, at least about 98%, at least about 99% or 100% homologous to an amino acid sequence selected from the group consisting of SEQ ID NOs: 36 and 38 and conservative substitutions thereof. In certain embodiments, a kit of this disclosure can include a modified vaccinia virus comprising one or more nucleic acids that can encode a dominant-negative mutant STAT3 protein having the amino acid sequence of SEQ ID NO: 36 or a fragment thereof.

In certain embodiments, a kit of this disclosure can include instructions for use, a device for administering the modified virus to a subject, or a device for administering an additional agent or compound to a subject. For example, and not by way of limitation, the instructions can include a description of the modified virus and, optionally, other components included in the kit, and methods for administration, including methods for determining the proper state of the subject, the proper dosage amount and the proper administration method for administering the modified virus. Instructions can also include guidance for monitoring the subject over duration of the treatment time.

In certain embodiments, a kit of this disclosure can include a device for administering the modified virus to a subject. Any of a variety of devices known in the art for administering medications and pharmaceutical compositions can be included in the kits provided herein. For example, and not by way of limitation, such devices include, a hypodermic needle, an intravenous needle, a catheter, a needle-less injection device, an inhaler and a liquid dispenser, such as an eyedropper. In certain embodiments, a modified virus to be delivered systemically, for example, by intravenous injection, can be included in a kit with a hypodermic needle and syringe.

EXAMPLES

The examples below further illustrate the described embodiments without limiting the scope of this disclosure.

Example 1: PIAS3 Blocks STAT3 Function

As shown in FIG. 1, human PIAS3 is a 628 amino acid protein that includes a PINIT domain, which includes amino acids 133-316. The PINIT domain includes a PINIT fragment that includes amino acids 132-177.

An exemplary oncolytic virus expressing a PIAS3 protein or a fragment thereof was prepared as follows: human PIAS3 DNA was obtained by reverse transcription PCR on mRNA derived from a buccal cell swab. Full-length PIAS3, segment 133-316, or segment 132-177 was cloned into a vector containing a luciferase reporter and flanking regions with segments of the vaccinia virus TK gene. Vectors varied by the type of PIAS3 construct, the viral promoter, and the inclusion or exclusion of an HIV TAT-derived or other cell-penetrating peptide sequence linked to the PIAS3 sequence. The different PIAS3 constructs were as follows: full-length PIAS3 gene, $PIAS3_{133-316}$+TAT with P11 promoter (DCP), $PIAS3_{133-316}$+TAT with P7.5 promoter (DC7), $PIAS3_{133-316}$ with P11 promoter (DNP), $PIAS3_{133-316}$ with P7.5 promoter (DN7), $PIAS3_{132-177}$+TAT with P11 promoter (FCP), $PIAS3_{132-177}$+TAT with P7.5 promoter (FC7), $PIAS3_{132-177}$ with P11 promoter (FNP) and $PIAS3_{132-177}$ with P7.5 promoter (FN7). Vectors were then transfected into the green monkey kidney epithelial cell line CV-1, which were simultaneously infected with the Western Reserve strain of wildtype vaccinia virus. Transfection and infection of these cells resulted in non-homologous recombination between the TK sites in the vector which replaced the TK gene in the vaccinia genome with one of the PIAS3 constructs and luciferase reporter. PIAS3-expressing vaccinia virus was selected by six rounds of luciferase-positive viral plaque purification and verified by DNA sequencing.

Figure 2:
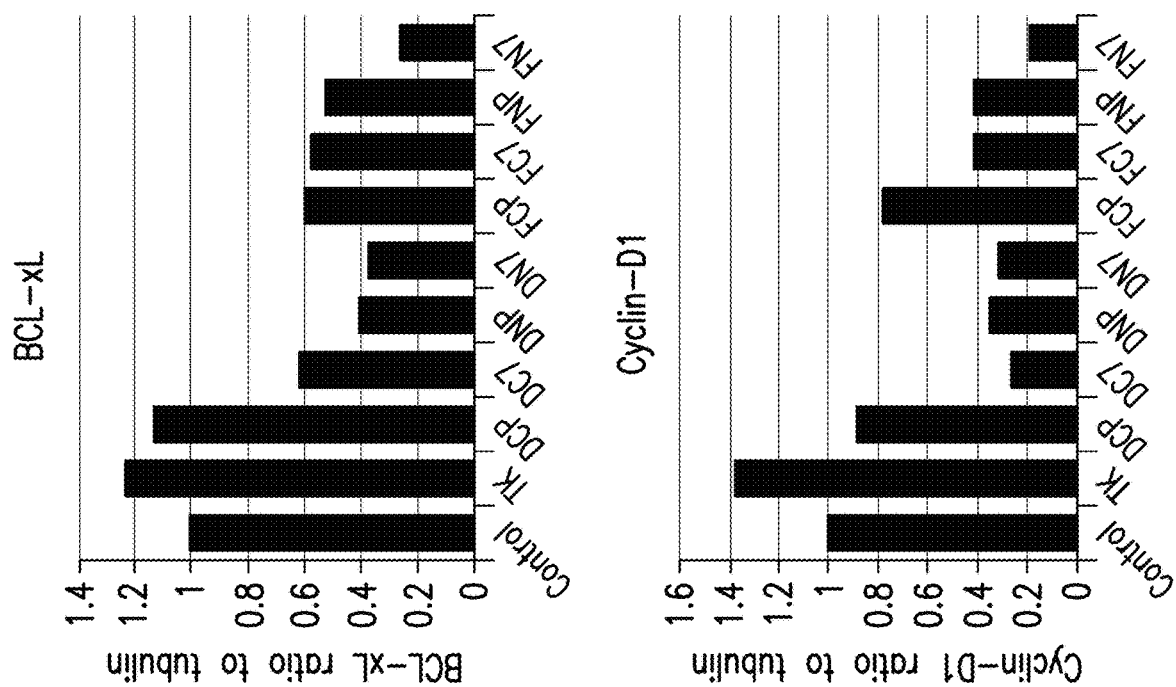
FIG. 2 shows that STAT3 blocking function of different vaccinia virus constructs expressing PIAS3.
Figure 2:
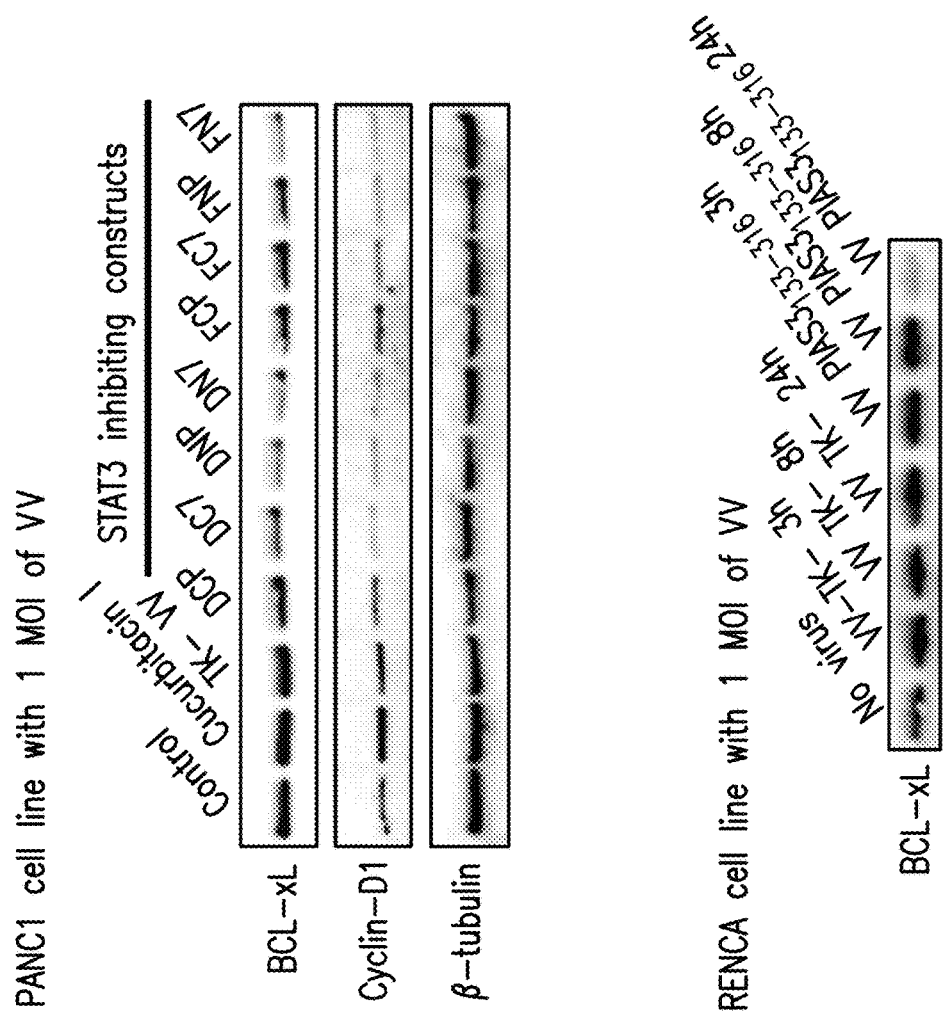

The ability of vaccinia viruses expressing PIAS3, the PINIT domain or the PINIT fragment to block STAT3 activity were analyzed in the human epithelioid carcinoma cell line, PANC1, and the mouse renal cortical adenocarcinoma cell line, RENCA, by determining the expression levels of STAT3 regulated proteins. The Western Reserve vaccinia strain was obtained from BEI Resources (Manassas, VA), and all recombinant vaccinia viruses used or constructed were based on this strain. The expression levels of STAT3 regulated proteins, BCL-xL and Cyclin-D1, were analyzed upon treatment with the STAT3 inhibiting constructs or vaccinia virus expressing amino acids 133-316 of human PIAS3. As shown in FIG. 2, the STAT3 inhibiting constructs and the vaccinia virus expressing amino acids 133-316 of human PIAS3 reduced the expression of BCL-xL and Cyclin-D1 as compared to the TK– vaccinia virus control, which did not express PIAS3 constructs.

Example 2: Expression of PIAS3 Enhances Cell Death of Cancer Cells

To test the effect the expression of PIAS3 has on human tumor cell lines, the renal cell carcinoma cell line, RCC4, the pancreatic adenocarcinoma epithelial cell line, PL45, the pancreatic epithelioid carcinoma cell line, PANC1, and the renal cortical adenocarcinoma cell line, RENCA, were infected with vaccinia virus expressing PIAS3 or PIAS3 domains and the viability of such cells were monitored over time. To measure cell viability, an MTS assay (CELLTITER 96® AQueous Non-Radioactive Cell Proliferation Assay, Promega) was performed on cells each day for 1 week post-infection.

Figure 3:
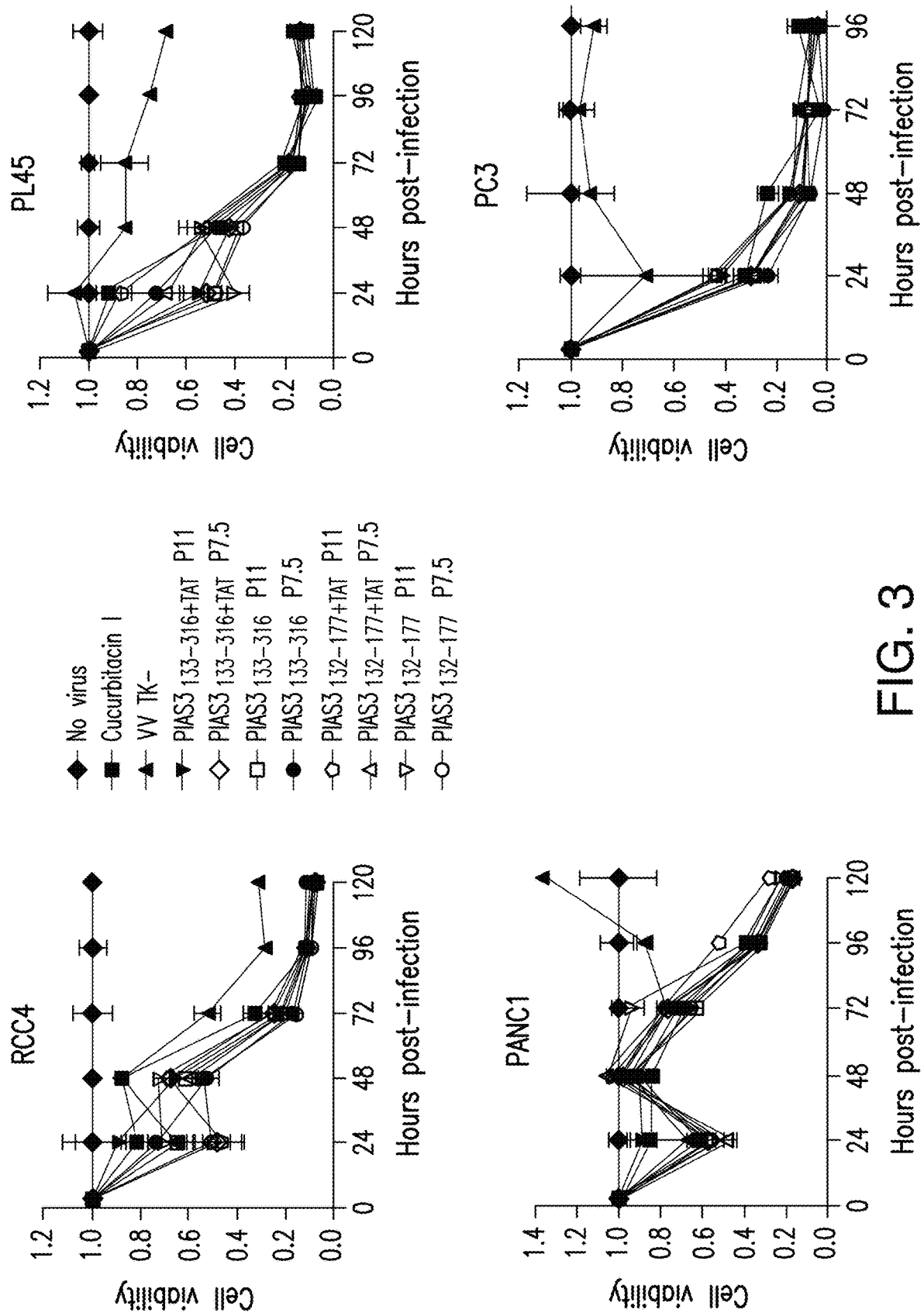
FIG. 3 shows that the expression of PIAS3 or domains of PIAS3 enhances vaccinia-mediated killing of human tumor cell lines.
Figure 4:
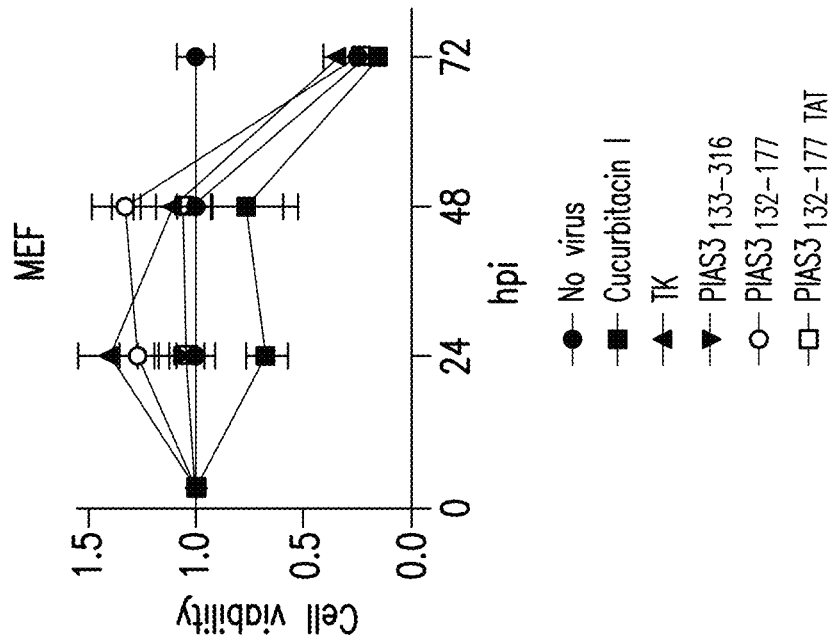
FIG. 4 shows that there is no additional killing was observed in normal cell lines using the vaccinia viruses expressing PIAS3.
Figure 4:
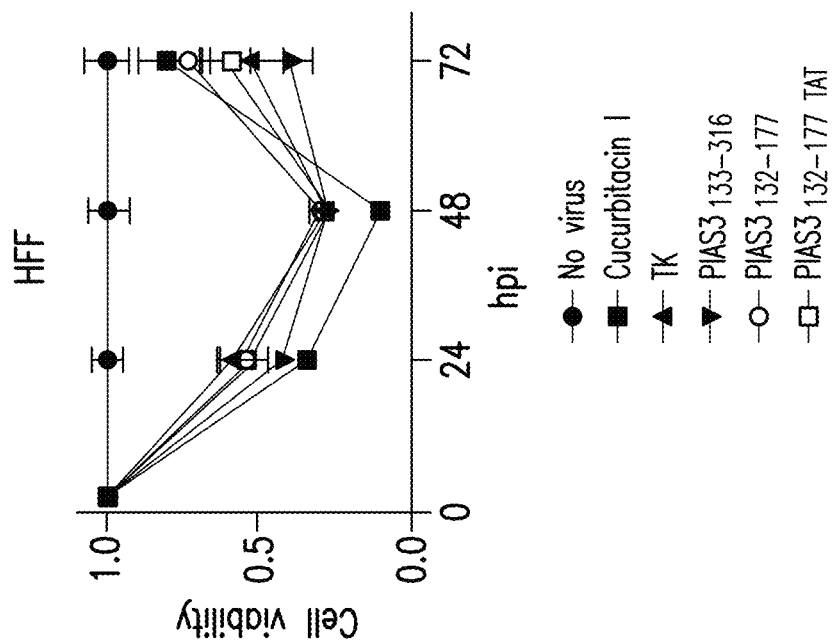

As shown in FIG. 3, the expression of PIAS3 enhanced vaccinia virus-mediated killing of the human tumor cell lines as compared to the control and the STAT3 inhibitor, cucurbitacin I. In addition, as shown in FIG. 4, no additional killing by the PIAS3-expressing vaccinia viruses was observed in normal cell lines, e.g., human foreskin fibroblasts (HFFs) and mouse embryonic fibroblasts (MEFs) as compared to the control. In particular, vaccinia viruses that express PIAS3 or a fragment thereof, e.g., $PIAS_{133-316}$, $PIAS_{132-177}$ or $PIAS_{132-177\ TAT}$, exhibited less toxicity than cucurbitacin I.

Figure 5:
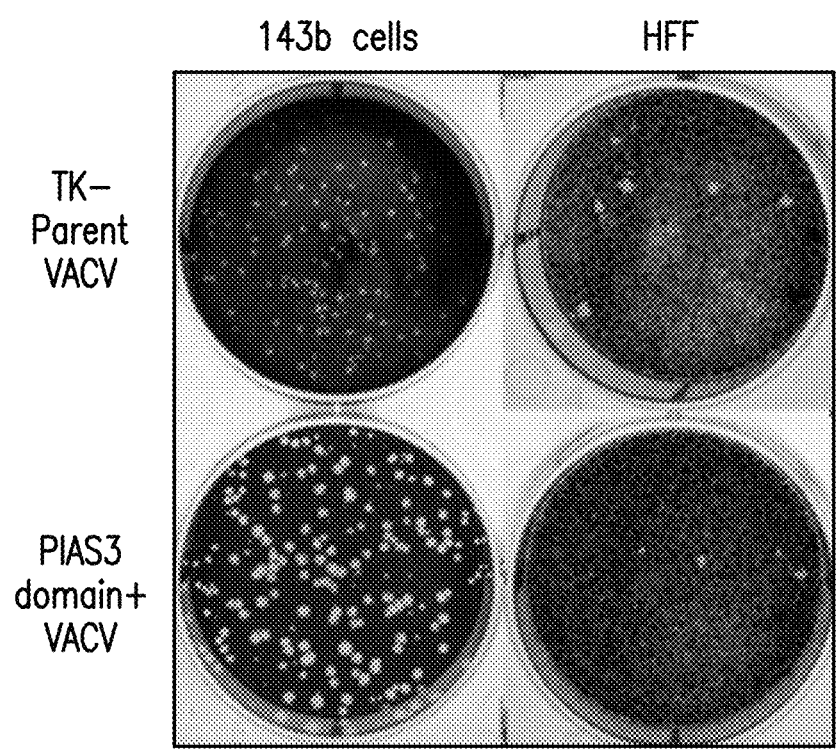
FIG. 5 shows that the expression of PIAS3 domains increases viral plaque size in tumor cells (143b) but not in normal cells (HFF).

In addition, as shown in FIG. 5, infection with the vaccinia virus expressing $PIAS_{133-316}$ resulted in increased plaque size in the osteosarcoma tumor cell line, 143b, as compared to the normal cell line, HFF. Larger plaque size can be interpreted as an enhancement of viral replication and/or enhancement of virus spreading.

These results show that the expression of the PINIT domain or the PINIT fragment of PIAS3 is sufficient to promote cancer cell death.

Example 3: Viral Replication is Increased by PIAS3 Expression

Figure 6:
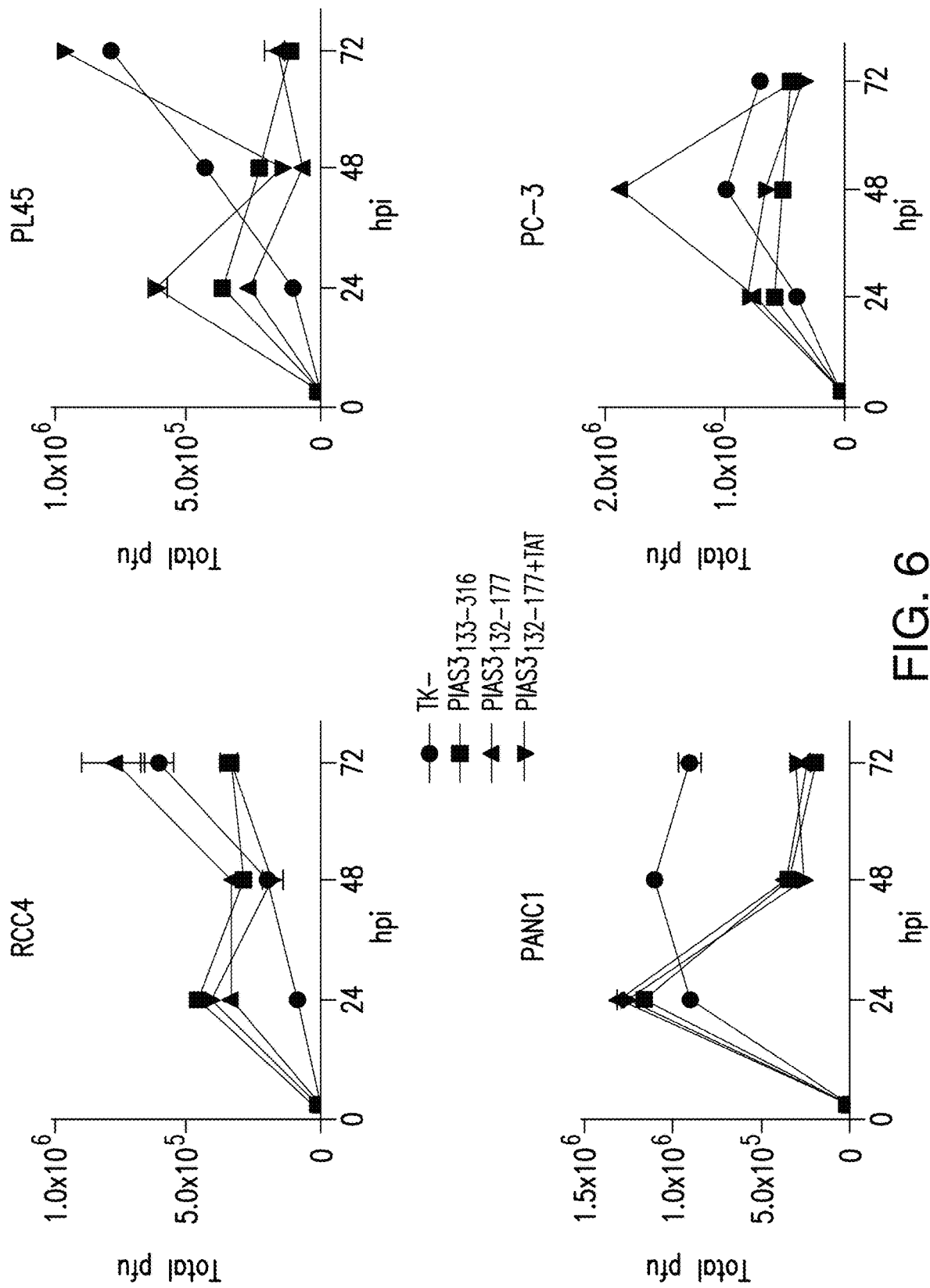
FIG. 6 shows that viral replication is increased in tumor cells when PIAS3 or domains of PIAS3 are expressed.

To determine if viral replication is affected by PIAS3 expression, the same panel of human tumor cell lines as in Example 2 were infected with vaccinia virus expressing the domains of PIAS3 and the luciferase gene. Viral replication was measured by virus plaque assay and is given as plaque forming units per mL (PFU/mL). As shown in FIG. 6, viral replication was increased in tumor cells by the expression of $PIAS_{133-316}$, $PIAS_{132-177}$ or $PIAS_{132-177\ TAT}$ as compared to viruses that are TK–.

Figure 7:
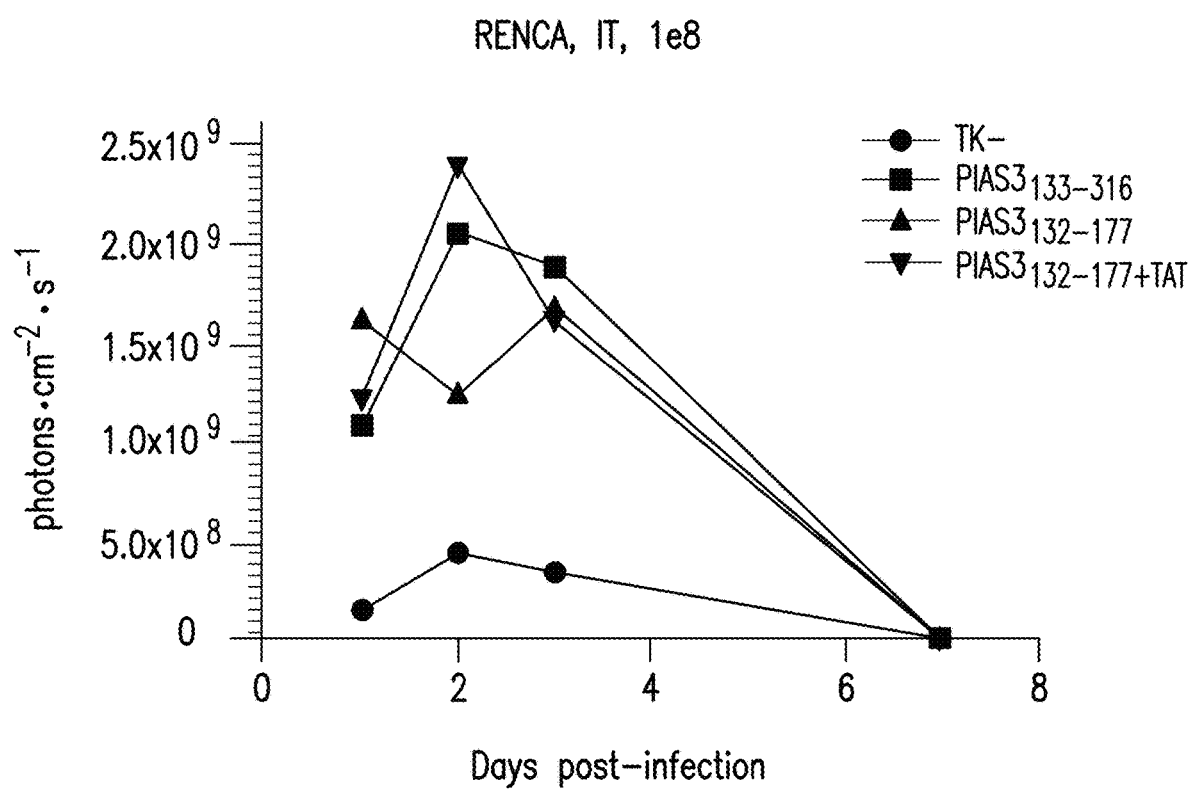
FIG. 7 shows that viral luciferase gene expression (replication) in a tumor is increased when PIAS3 domains are expressed.

Viral gene expression in the tumor was measured by bioluminescence imaging of luciferase expression in vivo. As shown in FIG. 7, in the RENCA tumor model (implanted subcutaneously in BALB/c mice) was injected with single intravenous dose of $1\times10^8$ PFU of the modified vaccinia viruses intratumorally. Viral luciferase expression in the tumor increased when PIAS3 domains were expressed, confirming that viral replication was increased in tumor cells by expression of the PIAS3 domains (FIG. 7). In particular, viral gene expression was increased about 5 to 10 fold by expression of the PIAS3 domains.

Example 4: Expression of PIAS3 Reduced Tumor Volume

Figure 8:
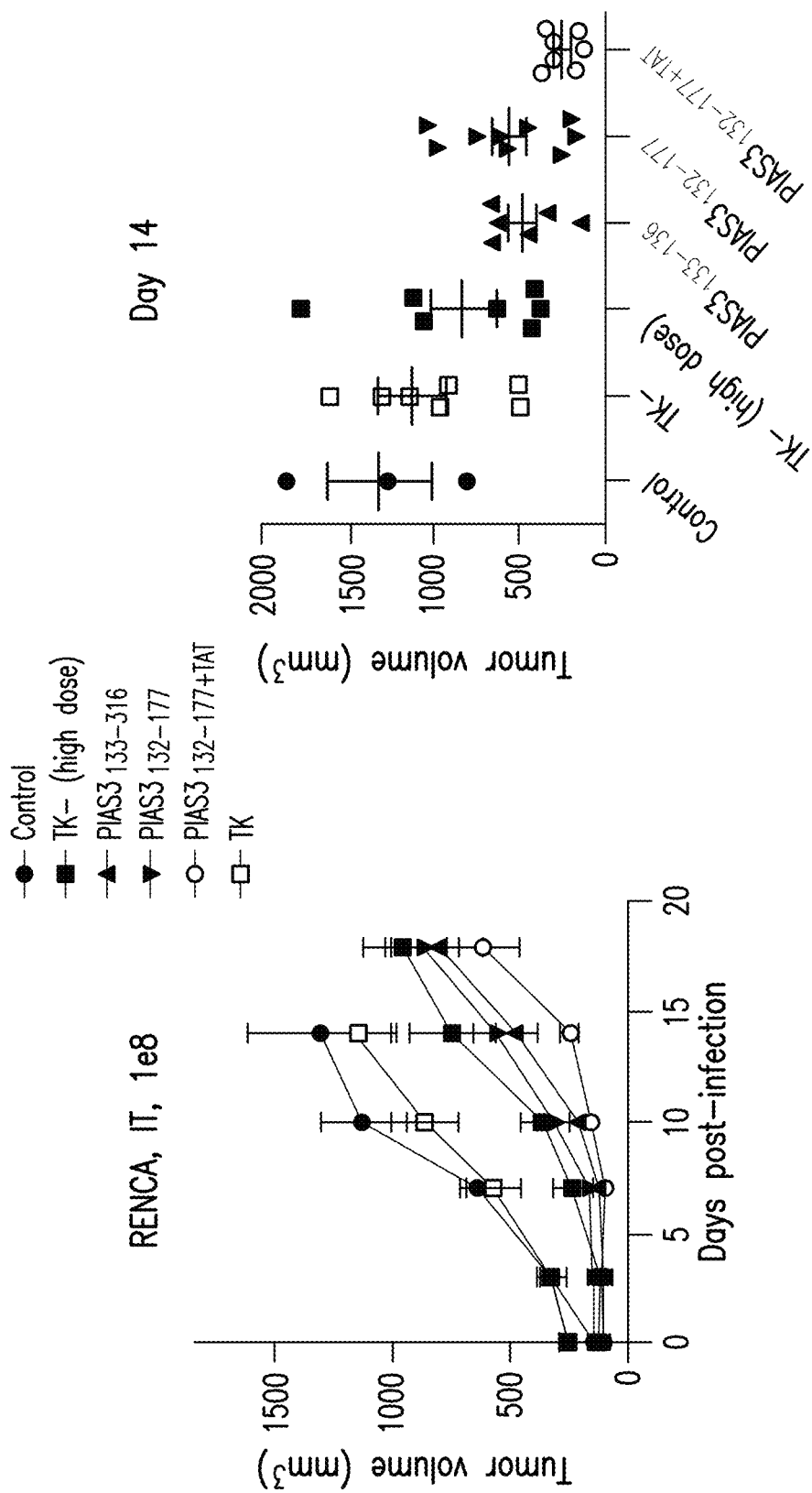
FIG. 8 shows the therapeutic effects of different vaccinia viruses expressing PIAS3 in mouse RENCA tumor models.

To determine if PIAS3 expression affected tumor volumes, tumors generated by the implantation of RENCA cells in BALB/c mice, were treated with vaccinia viruses that express PIAS3 or a fragment thereof, e.g., $PIAS_{133-316}$, $PIAS_{132-177}$ or $PIAS_{132-177\ TAT}$. A single intravenous dose of $1\times10^8$ PFU was administered intratumorally per mouse. For the high dose administration, a single intravenous dose of $5\times10^9$ PFU was administered intratumorally. As shown in FIG. 8, the tumor volume reduced by expression of $PIAS_{133-316}$, $PIAS_{132-177}$ or $PIAS_{132-177\ TAT}$, as compared to the control or the vaccinia virus with the TK deletion.

Figure 9:
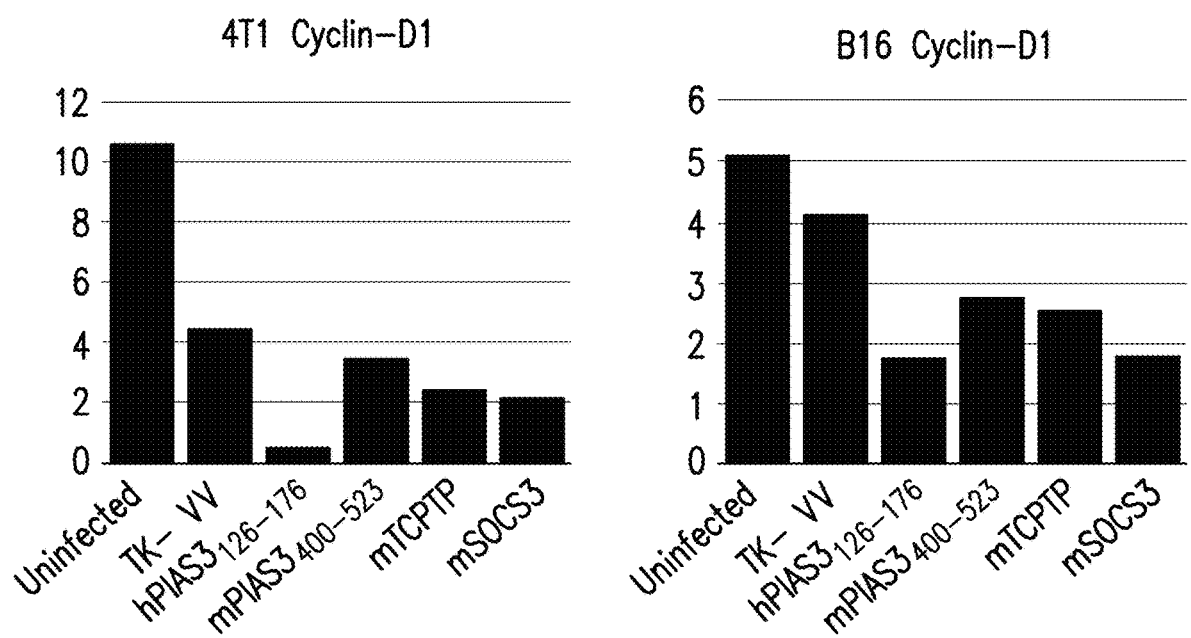
FIG. 9 shows that the expression of vaccinia viruses expressing hPIAS3$_{126-176}$, mPIAS3$_{400-523}$, mTCPTP or mSOCS3 resulted in decreased Cyclin D expression in tumor cell lines.

Example 5: Expression of the Acidic Domain of PIAS3 and Expression of TCPTP or SOCS3 Decreased STAT3 Activity To determine if the acidic domain of PIAS3 affected the expression of the downstream target of STAT3, Cyclin D1, 12-well plates of confluent mouse cell lines 4T1 or B16 were infected at 5 MOI with either TK– vaccinia virus or vaccinia viruses expressing $hPIAS3_{126-176}$ or $mPIAS3_{400-523}$. After 18 h, cells were lysed with 2× Laemmli buffer, boiled for 5 minutes, and run on SDS-PAGE for Western blotting. To detect changes in STAT3-regulated genes, membranes were stained with anti-Cyclin D1 or anti-BCL-xL antibodies and compared to control staining of β-tubulin. Results are displayed as the ratio of band intensity of STAT3-regulated genes versus β-tubulin expression. As shown in FIG. 9, the acidic domain of PIAS3 resulted in a decrease in Cyclin D1 expression.

To determine if additional regulators of STAT3 activity can affect expression of cyclin D1, 4T1 or B16 were infected at 5 MO with vaccinia viruses expressing mTCPTP or mSOCS3. As shown in FIG. 9, vaccinia virus expressing mTCPTP and vaccinia virus expressing mSOCS3 resulted in a decrease in Cyclin D1 expression.

Various NCBI accession numbers, publications, patents and patent applications are cited herein, the contents of which are hereby incorporated by reference in their entireties.

The invention claimed is:

1. A method of treating a cancer or a tumor, the method comprising administering to a subject in need thereof a therapeutically effective amount of an oncolytic vaccinia virus comprising an exogenous nucleic acid that encodes a protein or a fragment thereof that modulates STAT3-mediated gene-activation, or a pharmaceutical composition thereof, wherein the protein or the fragment thereof is a PIAS3 protein or a fragment thereof.

2. The method of claim 1, wherein the cancer is a solid tumor, a leukemia, or a lymphoma.

3. The method of claim 1, wherein a further therapy comprising chemotherapy, radiation, oncolytic viral therapy with an additional virus, treatment with immunomodulatory proteins, a STAT3 inhibitor, an anti-cancer agent, or any combinations thereof is administered to the subject.

4. The method of claim 3, wherein the further therapy is administered concurrently or sequentially.

5. The method of claim 3, comprising sequential administration of the further therapy, wherein the further therapy is administered prior to administering the oncolytic vaccinia virus, or after administering the oncolytic vaccinia virus.

6. The method of claim 1, comprising the administration of the oncolytic vaccinia virus, wherein the oncolytic vaccinia virus or the pharmaceutical composition is administered at a dosage that comprises about $10^6$ PFU/mL to about $10^8$ PFU/mL of the oncolytic vaccinia virus.

7. The method of claim 1, comprising the administration of the oncolytic vaccinia virus, wherein the oncolytic vaccinia virus or the pharmaceutical composition is administered, independently, in an initial dose for a first period of time, an intermediate dose for a second period of time, and a higher dose relative to the intermediate dose for a third period of time.

8. The method of claim 7, comprising administration of the initial, the intermediate, and the higher dose, independently, wherein the initial dose is lower than the intermediate dose and the intermediate dose is lower than the higher dose.

9. The method of claim 8, wherein the first, second, and third periods of time are each from about 1 week to about 3 weeks.

10. The method of claim 1, comprising administering the oncolytic vaccinia virus, wherein the oncolytic vaccinia virus and the pharmaceutical composition independently comprises a liquid dosage form that is administered at a volume of about 1 mL to about 5 mL, about 5 mL to 10 mL, about 15 mL to about 20 mL, about 25 mL to about 30 mL, about 30 mL to about 50 mL, about 50 mL to about 100 mL, about 100 mL to 150 mL, about 150 mL to about 200 mL, about 200 mL to about 250 mL, about 250 mL to about 300 mL, about 300 mL to about 350 mL, about 350 mL to about 400 mL, about 400 mL to about 450 mL, about 450 mL to 500 mL, about 500 mL to 750 mL, or about 750 mL to 1000 mL.

11. The method of claim 1, comprising administering the oncolytic vaccinia virus, wherein the oncolytic vaccinia virus or the pharmaceutical composition is administered in a liquid dosage form, a solid dosage form, an inhalable dosage form, an intranasal dosage form, in a liposomal formulation, a dosage form comprising nanoparticles, a dosage form comprising microparticles, a polymeric dosage form, or any combinations thereof.

12. The method of claim 1, comprising administering the oncolytic vaccinia virus, wherein the oncolytic vaccinia virus or the pharmaceutical composition is administered for a duration of about 1 week, about 2 weeks, about 3 weeks, about 4 weeks, about 6 weeks, about 7 weeks, about 8 weeks, about 9 weeks, about 10 weeks, or about 12 weeks.

13. The method of claim 1, comprising administering the oncolytic vaccinia virus, wherein the oncolytic vaccinia virus or the pharmaceutical composition is administered once daily, twice daily, once every week, once every two weeks, or once every three weeks.

14. The method of claim 1, comprising administering the oncolytic vaccinia virus, wherein the oncolytic vaccinia virus or the pharmaceutical composition is administered intravenously or by an intratumoral injection.

15. The method of claim 1, comprising administering the oncolytic vaccinia virus, wherein the administration of the oncolytic vaccinia virus or the pharmaceutical composition results in a first peak viral load after about 1 hour to about 3 days and a second peak viral load after about 3 days to about 7 days from administration of a first dose.

16. The method of claim 4, comprising administration of the further therapy, wherein the further therapy is administered for a duration of about 1 week, about 2 weeks, about 3 weeks, about 4 weeks, about 6 weeks, about 7 weeks, about 8 weeks, about 9 weeks, about 10 weeks, or about 12 weeks.

17. The method of claim 4, comprising administration of the further therapy, wherein the further therapy is administered once daily, once every week, once every two weeks, or once every three weeks.

18. The method of claim 3, comprising administration of the further therapy, wherein the further therapy is administered in a liquid dosage form, a solid dosage form, an inhalable dosage form, an intranasal dosage form, in a liposomal formulation, a dosage form comprising nanoparticles, a dosage form comprising microparticles, a polymeric dosage form, or any combinations thereof.

19. The method of claim 3, comprising administration of the further therapy, wherein the further therapy is administered orally, intravenously, by an intratumoral injection, or by radiation.

20. The method of claim 1, comprising the administration of the oncolytic vaccinia virus to a subject in need thereof, wherein the subject is human.

* * * * *